US010847255B2

(12) United States Patent
Hattori

(10) Patent No.: US 10,847,255 B2
(45) Date of Patent: Nov. 24, 2020

(54) INFORMATION PROCESSING SYSTEM, INFORMATION PROCESSING SERVER, STORAGE MEDIUM STORING INFORMATION PROCESSING PROGRAM, AND INFORMATION PROVISION METHOD

(71) Applicant: NINTENDO CO., LTD., Kyoto (JP)

(72) Inventor: Yurie Hattori, Kyoto (JP)

(73) Assignee: Nintendo Co., Ltd., Kyoto (JP)

( * ) Notice: Subject to any disclaimer, the term of this patent is extended or adjusted under 35 U.S.C. 154(b) by 294 days.

(21) Appl. No.: 15/421,724

(22) Filed: Feb. 1, 2017

(65) Prior Publication Data
US 2017/0135495 A1 May 18, 2017

Related U.S. Application Data

(63) Continuation of application No. PCT/JP2015/069653, filed on Jul. 8, 2015.

(51) Int. Cl.
*G16H 10/60* (2018.01)
*G16H 40/63* (2018.01)
(Continued)

(52) U.S. Cl.
CPC ............. *G16H 10/60* (2018.01); *A47C 31/00* (2013.01); *A61B 5/0022* (2013.01); *A61B 5/024* (2013.01);
(Continued)

(58) Field of Classification Search
CPC ........ G16H 10/60; G16H 50/30; G16H 40/63; G16H 10/20; G16H 50/20; G16H 50/70;
(Continued)

(56) References Cited

U.S. PATENT DOCUMENTS 6,809,653 B1  10/2004  Mann et al.
6,993,380 B1   1/2006  Modarres
(Continued)

FOREIGN PATENT DOCUMENTS

EP  2 570 976 A1  3/2013
JP  9-34424        2/1997
(Continued)

OTHER PUBLICATIONS

Extended European Search Report dated Mar. 9, 2018 issued in European Application No. 15830638.1 (11 pgs.).
(Continued)

*Primary Examiner* — Matthew Kremer
*Assistant Examiner* — Avery M Foley
(74) *Attorney, Agent, or Firm* — Nixon & Vanderhye, P.C.

(57) ABSTRACT

An example information processing system performs an analysis relating to health of a user based on biological information of the user so as to provide information to the user based on a result of the analysis. The information processing system updates, for each user, at least a part of a rule for deciding information to be provided based on the biological information. Thus, the information processing system can provide information that is useful for the user. Note that the update of the rule is performed based on the biological information of the user that is obtained after the provision of the information, for example.

25 Claims, 30 Drawing Sheets

US 10,847,255 B2
Page 2

(51) Int. Cl.

| | |
|---|---|
| G16H 50/30 | (2018.01) |
| G06F 16/22 | (2019.01) |
| G06Q 50/22 | (2018.01) |
| G06Q 30/02 | (2012.01) |
| G06F 19/00 | (2018.01) |
| G16H 20/30 | (2018.01) |
| G16H 40/67 | (2018.01) |
| A61B 5/00 | (2006.01) |
| H04N 9/31 | (2006.01) |
| A61B 5/11 | (2006.01) |
| A61B 5/16 | (2006.01) |
| A61B 5/024 | (2006.01) |
| G06Q 20/10 | (2012.01) |
| A63F 13/212 | (2014.01) |
| A47C 31/00 | (2006.01) |
| A61B 5/0205 | (2006.01) |
| G06Q 30/06 | (2012.01) |
| A61B 5/08 | (2006.01) |

(52) U.S. Cl.
CPC .............. *A61B 5/0205* (2013.01); *A61B 5/11* (2013.01); *A61B 5/1118* (2013.01); *A61B 5/16* (2013.01); *A61B 5/165* (2013.01); *A61B 5/4806* (2013.01); *A61B 5/486* (2013.01); *A61B 5/4809* (2013.01); *A61B 5/4812* (2013.01); *A61B 5/7271* (2013.01); *A61B 5/742* (2013.01); *A61B 5/7405* (2013.01); *A63F 13/212* (2014.09); *G06F 16/2228* (2019.01); *G06F 19/3418* (2013.01); *G06F 19/3481* (2013.01); *G06Q 20/10* (2013.01); *G06Q 30/02* (2013.01); *G06Q 30/0641* (2013.01); *G06Q 50/22* (2013.01); *G16H 20/30* (2018.01); *G16H 40/63* (2018.01); *G16H 40/67* (2018.01); *G16H 50/30* (2018.01); *H04N 9/3179* (2013.01); *H04N 9/3182* (2013.01); *H04N 9/3194* (2013.01); *A61B 5/08* (2013.01); *A61B 2560/0242* (2013.01)

(58) Field of Classification Search
CPC ... G16H 40/67; A63F 13/212; G06F 16/2228; G06F 19/3418; G06F 19/3481; G06F 19/08; A47C 31/00; A61B 5/0022; A61B 5/0205; A61B 5/024; A61B 5/11; A61B 5/1118; A61B 5/16; A61B 5/165; A61B 5/4806; A61B 5/4809; A61B 5/4812; A61B 5/486; A61B 5/7271; A61B 5/7405; A61B 5/742; A61B 2560/0242; G06Q 20/10; G06Q 30/02; G06Q 30/0641; G06Q 50/22; H04N 9/3179; H04N 9/3182; H04N 9/3194

See application file for complete search history.

(56) References Cited

U.S. PATENT DOCUMENTS

| | | | |
|---|---|---|---|
| 8,170,609 | B2 | 5/2012 | Hedtke et al. |
| 2001/0029535 | A1 | 10/2001 | Hirano et al. |
| 2001/0049471 | A1 | 12/2001 | Suzuki et al. |
| 2002/0024640 | A1 | 2/2002 | Ioka |
| 2002/0063855 | A1 | 5/2002 | Williams |
| 2002/0123908 | A1 | 9/2002 | Ando et al. |
| 2003/0003988 | A1 | 1/2003 | Walker |
| 2003/0013981 | A1 | 1/2003 | Gevins |
| 2003/0037124 | A1 | 2/2003 | Yamaura et al. |
| 2004/0039254 | A1 | 2/2004 | Stivoric |
| 2005/0061315 | A1 | 3/2005 | Lee et al. |
| 2005/0090372 | A1 | 4/2005 | Burrows |
| 2005/0258943 | A1 | 11/2005 | Mian et al. |
| 2005/0264425 | A1 | 12/2005 | Sato et al. |
| 2006/0071798 | A1 | 4/2006 | Kiff |
| 2007/0016443 | A1 | 1/2007 | Wachman |
| 2007/0100595 | A1 | 5/2007 | Earles et al. |
| 2007/0156060 | A1 | 7/2007 | Cervantes |
| 2007/0287501 | A1 | 12/2007 | Hoshina |
| 2008/0068158 | A1 | 3/2008 | Sumiyoshi et al. |
| 2008/0146866 | A1 | 6/2008 | Arai et al. |
| 2008/0162352 | A1* | 7/2008 | Gizewski ............ G06F 19/3456 705/50 |
| 2008/0311968 | A1 | 12/2008 | Hunter |
| 2008/0319855 | A1 | 12/2008 | Stivoric |
| 2009/0177327 | A1 | 7/2009 | Turner et al. |
| 2010/0112955 | A1 | 5/2010 | Krishnaswamy et al. |
| 2010/0216509 | A1 | 8/2010 | Riemer et al. |
| 2010/0268551 | A1 | 10/2010 | McNames |
| 2011/0015495 | A1 | 1/2011 | Dothie et al. |
| 2011/0119080 | A1 | 5/2011 | Hayter et al. |
| 2011/0137818 | A1 | 6/2011 | Goad et al. |
| 2011/0166875 | A1 | 7/2011 | Hayter et al. |
| 2011/0191158 | A1 | 8/2011 | Kaleraas et al. |
| 2011/0267196 | A1 | 11/2011 | Hu |
| 2012/0083705 | A1 | 4/2012 | Yuen et al. |
| 2012/0101889 | A1 | 4/2012 | Kurata et al. |
| 2012/0157209 | A1 | 6/2012 | Yamashita |
| 2012/0164946 | A1 | 6/2012 | Fujiwara et al. |
| 2012/0215328 | A1 | 8/2012 | Schmelzer |
| 2012/0253220 | A1 | 10/2012 | Rai et al. |
| 2012/0265546 | A1 | 10/2012 | Hwang et al. |
| 2012/0313791 | A1 | 12/2012 | Mehta |
| 2012/0330556 | A1 | 12/2012 | Shaanan et al. |
| 2013/0012234 | A1 | 1/2013 | Tufty et al. |
| 2013/0095459 | A1 | 4/2013 | Tran |
| 2013/0103416 | A1 | 4/2013 | Amigo et al. |
| 2013/0138450 | A1 | 5/2013 | Vigneux |
| 2013/0141235 | A1 | 6/2013 | Utter, II |
| 2013/0245465 | A1 | 9/2013 | Kasama |
| 2013/0280985 | A1 | 10/2013 | Klein |
| 2014/0111690 | A1 | 4/2014 | Kim |
| 2014/0121540 | A1 | 5/2014 | Raskin |
| 2014/0173586 | A1 | 6/2014 | Dugan |
| 2014/0198949 | A1 | 7/2014 | Garlington et al. |
| 2014/0222101 | A1 | 8/2014 | Miesel et al. |
| 2014/0247146 | A1 | 9/2014 | Proud |
| 2014/0269224 | A1 | 9/2014 | Huh |
| 2014/0274406 | A1 | 9/2014 | Walkingstick |
| 2014/0276245 | A1 | 9/2014 | Tsutsumi et al. |
| 2014/0316191 | A1 | 10/2014 | De Zambotti et al. |
| 2014/0347366 | A1 | 11/2014 | Emori et al. |
| 2014/0372133 | A1 | 12/2014 | Austrum et al. |
| 2014/0379374 | A1 | 12/2014 | Vinals |
| 2015/0018023 | A1 | 1/2015 | Tomii et al. |
| 2015/0094544 | A1 | 4/2015 | Spolin |
| 2015/0128353 | A1 | 5/2015 | Kildey |
| 2015/0258301 | A1* | 9/2015 | Trivedi ................ G06F 16/636 600/28 |
| 2016/0015315 | A1* | 1/2016 | Auphan ............... A61B 5/4815 600/301 |
| 2016/0151603 | A1* | 6/2016 | Shouldice ............ A61M 21/02 600/28 |
| 2016/0270718 | A1 | 9/2016 | Heneghan et al. |

FOREIGN PATENT DOCUMENTS

| | | |
|---|---|---|
| JP | 10-48363 | 2/1998 |
| JP | H11-070097 | 3/1999 |
| JP | 2001-273376 | 10/2001 |
| JP | 2001-344352 | 12/2001 |
| JP | 2002-034955 | 2/2002 |
| JP | 2002-41930 | 2/2002 |
| JP | 2002-072359 | 3/2002 |
| JP | 2002-149830 | 5/2002 |
| JP | 2002-222264 | 8/2002 |
| JP | 2002-245178 | 8/2002 |
| JP | 2002-315738 | 10/2002 |
| JP | 2003-015665 | 1/2003 |
| JP | 2003-264812 | 9/2003 |

(56) References Cited

FOREIGN PATENT DOCUMENTS

| | | |
|---|---|---|
| JP | 2003-299624 | 10/2003 |
| JP | 2003-319910 | 11/2003 |
| JP | 2004-157596 | 6/2004 |
| JP | 2004-530195 | 9/2004 |
| JP | 2005-050253 | 2/2005 |
| JP | 2005-074107 | 3/2005 |
| JP | 2005-237569 | 9/2005 |
| JP | 2005-237719 | 9/2005 |
| JP | 2006-263002 | 10/2006 |
| JP | 2007-004000 A | 1/2007 |
| JP | 2007-054596 | 3/2007 |
| JP | 2007-080219 | 3/2007 |
| JP | 2007-117365 | 5/2007 |
| JP | 2007-512086 | 5/2007 |
| JP | 2007-222276 | 9/2007 |
| JP | 2007-248052 | 9/2007 |
| JP | 2007-319238 | 12/2007 |
| JP | 2008-176741 | 7/2008 |
| JP | 2008-212391 | 9/2008 |
| JP | 2009-078070 | 4/2009 |
| JP | 2009-176130 | 8/2009 |
| JP | 2009-251452 | 10/2009 |
| JP | 2010-099173 | 5/2010 |
| JP | 2010-170534 | 8/2010 |
| JP | 2010-201113 | 9/2010 |
| JP | 2011-36649 | 2/2011 |
| JP | 2011-160327 | 8/2011 |
| JP | 2011-243041 | 12/2011 |
| JP | 2012-503804 | 2/2012 |
| JP | 2012-134737 | 7/2012 |
| JP | 2012-139362 | 7/2012 |
| JP | 2012-147879 | 8/2012 |
| JP | 2013-511780 | 4/2013 |
| JP | 2013-117941 | 6/2013 |
| JP | 2013-146463 | 8/2013 |
| JP | 2013-168026 | 8/2013 |
| JP | 2013-182422 | 9/2013 |
| JP | 2013-192620 | 9/2013 |
| JP | 2013-537435 | 10/2013 |
| JP | 2013-257837 | 12/2013 |
| JP | 2014-052834 | 3/2014 |
| WO | 02/073864 | 9/2002 |
| WO | 2005/055802 | 6/2005 |
| WO | WO 2005/055802 | 6/2005 |
| WO | WO 2005/094667 | 10/2005 |
| WO | WO 2007/023818 | 3/2007 |
| WO | 2008/096307 A1 | 8/2008 |
| WO | 2010/036700 | 4/2010 |
| WO | WO 2010/036700 | 4/2010 |
| WO | WO 2011/136253 | 11/2011 |
| WO | 2011/150362 | 12/2011 |
| WO | WO 2011/150362 | 12/2011 |
| WO | WO 2011/156272 | 12/2011 |
| WO | 2012/006549 | 1/2012 |
| WO | 2013/065246 | 5/2013 |
| WO | 2013/065504 A1 | 5/2013 |
| WO | WO 2013/080109 | 6/2013 |

OTHER PUBLICATIONS

Decision of Refusal dated Mar. 19, 2019 issued in JP Application No. 2015-557713 (2 pages).
Decision of Dismissal of Amendment dated Mar. 19, 2019 issued in JP Application No. 2015-557713 (6 pages).
Extended European Search Report dated Sep. 12, 2017 issued in European Patent Application No. 14878891.2 (9 pgs.).
Julie Guan "All-in Pedometer iPhone app review AppSafari", XP055403538, Jan. 25, 2011 (8 pgs.).
Final Office Action dated Jan. 25, 2019, issued in Kawai, et al., U.S. Appl. No. 15/211,300 (31 pages).
Office Action dated Nov. 29, 2018 issued in U.S. Appl. No. 15/211,122 (16 pgs.).
Office Action dated Jun. 21, 2018 issued in U.S. Appl. No. 15/211,497.
Office Action dated Jan. 12, 2018 issued in co-pending U.S. Appl. No. 15/211,497 (24 pgs.).
Office Action dated Oct. 4, 2018 issued in U.S. Appl. No. 15/211,387 (37 pgs.).
Office Action dated Aug. 31, 2018 issued in U.S. Appl. No. 15/211,265 (36 pages).
M. Sato et al., "Wireless Sensor Systems" $1^{st}$ Edition, Tokyo Denki University Press, Oct. 30, 2012, pp. 186 and 196.
Kawai et al., U.S. Appl. No. 15/211,122, filed Jul. 15, 2016 (149 pages).
Kawai et al., U.S. Appl. No. 15/211,146, filed Jul. 15, 2016 (130 pages).
Kawai et al., U.S. Appl. No. 15/211,182, filed Jul. 15, 2016 (214 pages).
Kawai et al., U.S. Appl. No. 15/211,265, filed Jul. 15, 2016 (219 pages).
Kawai et al., U.S. Appl. No. 15/211,300, filed Jul. 15, 2016 (209 pages).
Kawai et al., U.S. Appl. No. 15/211,387, filed Jul. 15, 2016 (218 pages).
Kawai et al., U.S. Appl. No. 15/211,497, filed Jul. 15, 2016 (210 pages).
Hattori., U.S. Appl. No. 15/421,708, filed Feb. 1, 2017 (132 pages).
English translation of International Preliminary Report on Patentability issued in PCT/JP2014/078824 dated Jul. 19, 2016 (14 pages).
English translation of International Preliminary Report on Patentability issued in PCT/JP2014/078825 dated Jul. 19, 2016 (14 pages).
Office Action dated Mar. 7, 2019 issued in U.S. Appl. No. 15/211,497 (40 pgs.).
Office Action dated Feb. 1, 2019 issued in U.S. Appl. No. 15/211,182 (13 pgs.).
Office Action dated Feb. 4, 2019 issued in U.S. Appl. No. 15/421,708 (13 pgs.).
Partial Supplementary European Search Report dated Sep. 5, 2017 issued in European Application No. 14878971.2 (7 pages).
European Search Report dated Aug. 7, 2017, issued in corresponding EP Application No. 14878426.7 (9 pages).
Office Action dated Aug. 16, 2018 issued in corresponding Japanese Application No. 2015-557699 (8 pages).
Office Action dated Oct. 24, 2018 issued in JP Application No. 2015-557716 (3 pgs.).
Office Action dated Jun. 8, 2017 issued in co-pending U.S. Appl. No. 15/211,497 (15 pgs.).
Office Action dated Aug. 27, 2018 issued in U.S. Appl. No. 15/211,300 (28 pgs.).
Notice of Reasons for Refusal dated Mar. 13, 2019 issued in JP Application No. 2015-557714 (2 pages).
Office Action—Notice of Reasons for Refusal dated Nov. 5, 2018 issued in JP Application No. 2015-557713 (4 pages).
Purewal, "Review: Runtastic's mobile apps make tracking a workout easier PCWorld", Nov. 29, 2012, XP055598914, Retrieved from the internet: https://pcworld.com/article/2017159/review-runtastics-mobile-apps-make-tracking-a-workout-easier.html, retrieved on Jun. 24, 2019.
Communication received in corresponding European Patent Application No. 14878891.2 dated Jun. 24, 2019 (5 pages).
Office Action dated Aug. 23, 2019 in corresponding U.S. Appl. No. 15/211,146.
U.S. Appl. No. 15/211,300, filed Jul. 15, 2016, Information Processing System, Server System, and Information Processing Program.
U.S. Appl. No. 15/211,497, filed Jul. 15, 2016, Display System and Display Device.
U.S. Appl. No. 15/211,387, filed Jul. 15, 2016, Information Processing System and Information Processing Apparatus.
U.S. Appl. No. 15/211,146, filed Jul. 15, 2016, Information Processing System, Information Processing Server, Information Processing Program, and Information Providing Method.
U.S. Appl. No. 15/211,122, filed Jul. 15, 2016, Information Processing System, Information Processing Server, Information Processing Program, and Fatigue Evaluation Method.

(56) References Cited

OTHER PUBLICATIONS

U.S. Appl. No. 15/211,182, filed Jul. 15, 2016, Information Processing System, Server System, Information Processing Apparatus, and Information Processing Method.
U.S. Appl. No. 15/211,265, filed Jul. 15, 2016, Information Processing System, Server System, Information Processing Program, and Information Processing Method.
U.S. Appl. No. 15/421,708, filed Feb. 1, 2017, Information Processing System, Information Processing Device, Storage Medium Storing Information Processing Program and Information Processing Method.
Office Action issued in U.S. Appl. No. 15/211,300 dated Dec. 20, 2019.
Office Action dated Oct. 21, 2019 in corresponding U.S. Appl. No. 15/211,387.
Notice of Reasons for Refusal in corresponding Japanese Patent Appln. No. 2019-007669 dated Oct. 29, 2019.
Notice of Allowance received in U.S. Appl. No. 15/211,182 dated Jun. 23, 2020.
Notice of Reasons for Refusal dated Feb. 3, 2020 in corresponding Japanese Patent Application No. 2018-196896.
Notice of Refusal dated Feb. 6, 2020 in corresponding Japanese Patent Application No. 2018-221951 with English Machine translation.
Ouchi et al., "Healthcare Services Using a Wearable Device", IPSJ SIG Technical Reports, Japan Information Processing Society of Japan, Feb. 23, 2007, vol. 2007, No. 14, pp. 29-36.
Office Action in corresponding U.S. Appl. No. 15/211,146 dated Feb. 7, 2020.
Office Action in U.S. Appl. No. 15/211,122 dated Apr. 30, 2020.
Office Action in related U.S. Appl. No. 15/211,265 dated Mar. 18, 2020.
Office Action in U.S. Appl. No. 15/211,300 dated Apr. 9, 2020.
Notice of Reasons for Refusal in Japanese Patent Appln. No. JP2019-172746 dated Sep. 28, 2020.

* cited by examiner

Fig. 9

| PROVISION CONDITION TABLE | | | |
|---|---|---|---|
| PROVISION CONDITION | | | PROVISION CONTENT |
| USER CONDITION | HEALTH CONDITION | | |
| | USE INFORMATION | | |
| MEN IN THEIR 40'S | AVERAGE FATIGUE LEVEL FOR PAST ONE WEEK | 4 OR LESS | INTRODUCE PRODUCT A |
| MEN IN THEIR 40'S | AVERAGE FATIGUE LEVEL FOR PAST ONE WEEK | 3 OR LESS | INTRODUCE PRODUCT B |
| MEN AND WOMEN IN THEIR 30'S | AVERAGE SLEEP TIME FOR PAST ONE WEEK | 5 HOURS OR LESS | INTRODUCE PRODUCT C |
| ⋮ | ⋮ | ⋮ | ⋮ |

Fig. 10

| REQUESTED INFORMATION | USER IDENTIFICATION INFORMATION | SERVICE IDENTIFICATION INFORMATION |
|---|---|---|
| AVERAGE FATIGUE LEVEL FOR DEC 13, 2013 TO DEC 20, 2013 | ○○○○ (USER A) | ×××× (PRODUCT A) |

Fig. 11

| USE MANAGEMENT TABLE | |
|---|---|
| SERVICE IDENTIFICATION INFORMATION | AVAILABLE INFORMATION |
| ○○○○ (PRODUCT A) | SLEEP INDICES AND FATIGUE INDEX |
| ×××× (PRODUCT B) | ALL INFORMATION |
| △△△△ (PRODUCT C) | SLEEP INDICES FOR PAST ONE MONTH |
| ⋮ | ⋮ |

| USER PROVISION HISTORY INFORMATION | | | |
|---|---|---|---|
| PROVISION CONTENT INFORMATION | PROVISION DATE INFORMATION | PURCHASE INFORMATION | TIME OF ADDITIONAL PROVISION INFORMATION |
| INTRODUCTION OF PRODUCT A | DEC 11, 2013 | NOT PURCHASED | NO ADDITIONAL PROVISION |
| INTRODUCTION OF PRODUCT B | DEC 13, 2013 | PURCHASED | DEC 27, 2013 |
| ⋮ | ⋮ | ⋮ | ⋮ |

Fig. 14

ADDITIONAL PROVISION CONDITION TABLE

| PREVIOUS PROVISION CONTENT | TIME OF ADDITIONAL PROVISION | ADDITIONAL PROVISION CONDITION | | ADDITIONAL PROVISION CONTENT |
|---|---|---|---|---|
| | | USE INFORMATION | | |
| INTRODUCTION OF PRODUCT A | TWO WEEKS FROM PURCHASE | AVERAGE FATIGUE LEVEL FOR PAST ONE WEEK, AND AVERAGE FATIGUE LEVEL FOR THE WEEK PRECEDING PURCHASE | FATIGUE LEVEL HAS IMPROVED | INTRODUCTION OF PRODUCT D |
| INTRODUCTION OF PRODUCT A | TWO WEEKS FROM PURCHASE | AVERAGE FATIGUE LEVEL FOR PAST ONE WEEK, AND AVERAGE FATIGUE LEVEL FOR THE WEEK PRECEDING PURCHASE | FATIGUE LEVEL HAS NOT IMPROVED | INTRODUCTION OF PRODUCT E |
| INTRODUCTION OF PRODUCT C | ONE MONTH FROM PURCHASE | AVERAGE SLEEP TIME FOR PAST ONE WEEK | 5 HOURS OR LESS | INTRODUCTION OF PRODUCT F |
| ... | ... | ... | ... | ... |

Fig. 18

CONDITION UPDATE TABLE

| PROVISION CONTENT | UPDATE CONDITION | | UPDATE CONTENT |
| --- | --- | --- | --- |
| | DATA COUNT CONDITION | CHANGE CONDITION | |
| INTRODUCTION OF PRODUCT A | EFFECTIVENESS INFORMATION FOR 100 PEOPLE | FOUND EFFECTIVE FOR A PREDETERMINED NUMBER OF PEOPLE OR MORE | RELAX PROVISION CONDITION FOR PRODUCT A (DECREASE THRESHOLD VALUE BY 0.1) |
| . . . | . . . | . . . | . . . |

Fig. 20

| PROVISION CONDITION TABLE | | | | | | |
|---|---|---|---|---|---|---|
| | PROVISION CONDITION | | | | PROVISION CONTENT | TIME OF NEXT PROVISION |
| AGE | AVERAGE TOTAL SLEEP TIME FOR PAST ONE WEEK | AVERAGE SLEEP EFFICIENCY FOR PAST ONE WEEK | AVERAGE NUMBER OF MID-SLEEP AWAKENINGS FOR PAST ONE WEEK | | | |
| 40'S | LESS THAN 6 HOURS | LESS THAN 80% | 3 OR MORE | | INTRODUCTION OF PRODUCT A | 2 WEEKS AFTER PURCHASE |
| 30'S | LESS THAN 5 HOURS | LESS THAN 60% | 3 OR MORE | | INTRODUCTION OF PRODUCT B | 1 MONTH AFTER PURCHASE |
| 40'S | LESS THAN 5 HOURS | LESS THAN 70% | NO CONDITION | | INTRODUCTION OF PRODUCT C | 2 WEEKS AFTER PURCHASE |
| ... | ... | ... | ... | | ... | ... |

Fig. 21

| CHANGE INFORMATION | | | | | | | |
|---|---|---|---|---|---|---|---|
| PURCHASE INFORMATION | USER INFORMATION | HEALTH INFORMATION BEFORE PURCHASE (1-WEEK AVERAGE) | | | HEALTH INFORMATION AFTER PURCHASE (1-WEEK AVERAGE) | | |
| | | TOTAL SLEEP TIME | SLEEP EFFICIENCY | ... | SLEEP LATENCY | TOTAL SLEEP TIME | SLEEP EFFICIENCY | ... | SLEEP LATENCY |
| PRODUCT A | MEN IN THEIR 40'S | 6[h] | 76[%] | ... | 20[min] | 7[h] | 84[%] | ... | 18[min] |
| PRODUCT A | WOMEN IN THEIR 20'S | 7[h] | 74[%] | ... | 9[min] | 6.5[h] | 69[%] | ... | 21[min] |
| ... | ... | ... | ... | ... | ... | ... | ... | ... | ... |
| PRODUCT B | MEN IN THEIR 40'S | 7[h] | 81[%] | ... | 33[min] | 7[h] | 82[%] | ... | 13[min] |
| ... | ... | ... | ... | ... | ... | ... | ... | ... | ... |

Fig. 28

| SLEEP CONDITION | SETTINGS |
|---|---|
| SLEEP LATENCY IS 15 MIN OR LESS | GENRE A : +0.5 |
| SLEEP LATENCY IS 15 MIN TO 1 HOUR | GENRE B : +0.5 |
| SLEEP LATENCY IS 1 HOUR OR MORE | GENRE C : +1 |
| NO MID-SLEEP AWAKENINGS | GENRE B : +1 |
| 1 TO 3 MID-SLEEP AWAKENINGS | GENRE D : +0.5 |
| 4 OR MORE MID-SLEEP AWAKENINGS | GENRE D : +1<br>GENRE B : −0.5 |
| ⋮ | ⋮ |

Fig. 29

| GENRE | TUNE | WEIGHT VALUE |
|---|---|---|
| GENRE A | TUNE A | 2.5 |
| GENRE A | TUNE B | 1.0 |
| GENRE B | TUNE C | 1.3 |
| ⋮ | ⋮ | ⋮ |

Fig. 30

| CONDITION | QUESTION |
|---|---|
| NUMBER OF MID-SLEEP AWAKENINGS IS GREATER THAN OR LESS THAN AVERAGE BY ONE OR MORE | DID YOU SLEEP WELL? |
| FATIGUE LEVEL IS GREATER THAN OR LESS THAN AVERAGE BY 15 POINTS OR MORE | DID YOU RECOVER FROM FATIGUE? |
| ⋮ | ⋮ |

Fig. 31

| CONDITION | UPDATE CONTENT |
|---|---|
| SLEEP TIME IS GREATER THAN OR EQUAL TO AVERAGE | WEIGHT : +0.1 |
| SLEEP LATENCY IS 15 MIN OR LESS | WEIGHT : +0.2 |
| SLEEP LATENCY IS 1 HOUR OR MORE | WEIGHT : -0.2 |
| NUMBER OF MID-SLEEP AWAKENINGS IS 1 OR LESS | WEIGHT : +0.1 |
| USER ANSWER IS "I SLEPT WELL" | WEIGHT : +0.1 |
| USER ANSWER IS "I RECOVERED FROM FATIGUE" | WEIGHT : +0.2 |
| ⋮ | ⋮ |

INFORMATION PROCESSING SYSTEM, INFORMATION PROCESSING SERVER, STORAGE MEDIUM STORING INFORMATION PROCESSING PROGRAM, AND INFORMATION PROVISION METHOD

CROSS REFERENCE TO RELATED APPLICATIONS

This application is a continuation application of International Application No. PCT/JP2015/069653, filed on Jul. 8, 2015, which designated the U.S. and claims priority to International Application Nos. PCT/JP2014/070931 filed on Aug. 7, 2014, PCT/JP2014/078824 filed on Oct. 29, 2014, PCT/JP2014/078825 filed on Oct. 29, 2014, PCT/JP2014/078826 filed on Oct. 29, 2014, PCT/JP2014/078827 filed on Oct. 29, 2014, PCT/JP2014/078828 filed on Oct. 29, 2014, PCT/JP2014/078829 filed on Oct. 29, 2014, PCT/JP2015/061273 filed on Apr. 10, 2015 and PCT/JP2015/061274 filed on Apr. 10, 2015, the entire contents of each of which are hereby incorporated by reference.

FIELD

The present technique relates to an information processing system, an information processing server, a storage medium storing an information processing program and an information provision method for providing information from the server side to the terminal side.

BACKGROUND AND SUMMARY

There are conventional systems in which information obtained on the terminal side is uploaded to the server side, and the result of an analysis of the uploaded information is provided from the server side to the terminal side. For example, there is a system in which sleep data of a user is obtained by an evaluation device on the terminal side and the sleep data is analyzed on the server side so as to display the analysis result on a display device on the terminal side.

In the prior art, it is possible that useful information is not provided, as the information to be provided from the server side to the terminal side.

In view of this, the present application discloses an information processing system, an information processing server, a storage medium storing an information processing program and an information provision method capable of providing useful information.

(1)
An example information processing system described herein includes analysis means and first update means. The analysis means is configured to perform an analysis relating to health of a user based on biological information of the user so as to provide information to the user based on a result of the analysis. The first update means is configured to update, for each user, based on the biological information of the user, at least a part of a rule for deciding information to be provided based on the biological information. The analysis means uses a rule that has been set for each user through updates to decide information to be provided to the user.

(2)
The rule may include a first part that is updated for each user and a second part that is common among a plurality of users including the user.

(3)
The information processing system may further include first obtaining means and second update means. The first obtaining means is configured to obtain biological information of each of a plurality of users. The second update means is configured to update the second part based on at least a plurality of biological information included in the biological information.

(4)
The information processing system may include one or more user terminal, and a server system that is capable of communicating with the user terminal via a network. The user terminal may at least include the analysis means and the first update means. The first update means may update the first part based on the biological information obtained by the user terminal thereof. The server system may obtain biological information of each of the plurality of users. The second update means may update the second part based on the plurality of biological information obtained by the server.

(5)
The first update means may update, for each user, at least a part of the rule based on the biological information of the user and an input by the user.

(6)
The information processing system may further include question presenting means configured to present a question to the user. The first update means may use an answer to the question as the input by the user.

(7)
The question presenting means may decide content of the question based on the biological information of the user that is obtained after the provision of the information so as to present the question to the user. The first update means may update, for each user, at least a part of the rule based on the biological information of the user that is obtained after the provision of the information and the answer to the question.

(8)
The information processing system may further include second obtaining means configured to obtain environment information relating to an environment around the user when sensing the biological information. The analysis means may decide the information to be provided based on the biological information of the user and the environment information relating to the user.

(9)
The information processing system may further include second obtaining means configured to obtain environment information relating to an environment around the user when sensing the biological information. The first update means may update at least a part of the rule based on the biological information of the user and the environment information relating to the user.

(10)
The first update means may provide, to the user, information relating to health of the user.

(11)
The first update means may provide, to the user, information for improving the health of the user.

(12)
The analysis means may repeatedly execute the analysis based on biological information that is obtained repeatedly. The information processing system may further include memory control means configured to store, in a predetermined storage section, at least a part of the biological information obtained repeatedly and information calculated in the repeatedly-executed analysis. The first update means may update, for each user, at least a part of the rule based on the biological information for a plurality of iterations and/or the information calculated over a plurality of iterations of the analysis, which are stored in the storage section.

(13)

The first update means may repeatedly update the rule.

(14)

The first update means may update the rule each time the analysis means performs the analysis.

(15)

The biological information may be obtained from a sensor configured to sense at least one of pulse, breathing and body movements of the user.

(16)

The analysis means may perform an analysis relating to sleep and/or fatigue of the user based on the biological information.

(17)

Another example information processing system described herein includes analysis means and information provision means. The analysis means is configured to perform an analysis relating to health of a user based on biological information of the user so as to decide information to be provided to the user based on a result of the analysis. The information provision means is configured to provide the decided information to the user. The analysis means decides the information to be provided to the user by using, as a rule for deciding the information to be provided, both a first rule that is common among a plurality of users and a second rule that is set individually for each of the plurality of users.

(18)

The analysis means may calculate first information for deciding the information to be provided to the user by using the biological information and the first rule so as to decide the information to be provided to the user by using the calculated first information and the second rule.

(19)

The analysis means may calculate second information by using the biological information and the second rule so as to decide the information to be provided to the user by correcting the first information with the second information.

Note that the present specification discloses an example information processing device (e.g., a hand-held terminal) and an example server included in the information processing system as set forth in (1) to (19) above. The present specification also discloses a storage medium storing an information processing program that causes the computer of the information processing device or the server to function as some of the various units set forth in (1) to (19) above. The present specification also discloses an example information processing method to be carried out in the information processing system, the information processing device or the server.

With the information processing system, the information processing device, the storage medium storing an information processing program and the information processing method set forth above, it is possible to provide information that is useful for the user.

These and other objects, features, aspects and advantages will become more apparent from the following detailed description when taken in conjunction with the accompanying drawings.

BRIEF DESCRIPTION OF THE DRAWINGS

FIG. 9 illustrates an example of a provision condition table.

FIG. 10 illustrates an example of a use request.

FIG. 11 illustrates an example of a use management table.

FIG. 14 illustrates an example of an additional provision condition table.

FIG. 18 illustrates an example of a condition update table.

FIG. 20 illustrates an example of a provision condition table according to a variation.

FIG. 21 illustrates an example of change information.

FIG. 28 illustrates an example genre decision rule.

FIG. 29 illustrates an example table included in a tune decision rule.

FIG. 30 illustrates an example table used for deciding a question to be presented to the user.

FIG. 31 illustrates an example rule update table used for deciding the update content.

DETAILED DESCRIPTION OF NON-LIMITING EXAMPLE EMBODIMENTS

First Embodiment

[1. Overall Configuration of Information Processing System]

Figure 1:
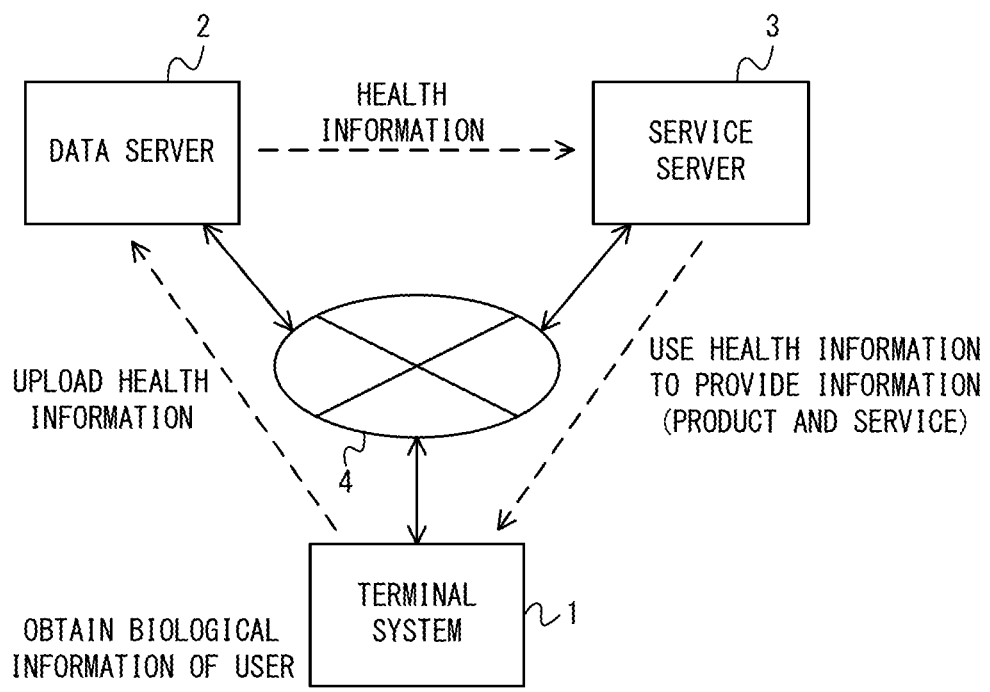
FIG. 1 is a block diagram illustrating an example of a configuration of an information processing system according to the first embodiment.

Hereinafter, an information processing system, an information processing server, an information processing program, and an information providing method according to the present embodiment will be described with reference to the drawings. Firstly, the overall configuration of the information processing system according to the present embodiment will be described. FIG. 1 is a block diagram illustrating an example of the configuration of the information processing system according to the present embodiment. As shown in FIG. 1, the information processing system includes a terminal system 1, a data server 2, and a service server 3. The system and servers 1 to 3 can communicate with each other through a network 4 such as the Internet and a mobile communication network.

The terminal system 1 is disposed near a user (for example, in the house of the user). In FIG. 1, the number of the terminal systems 1 is one. However, the information processing system includes a plurality of the terminal systems provided for users, respectively. In the present embodiment, the terminal system 1 obtains biological information of each user, and uploads the health information obtained from the biological information to the data server 2 (see FIG. 1). The biological information represents information sensed from a user's body. In the present embodiment, respiration, pulse, and body motion are obtained as the biological information. The health information represents information related to user's health and/or body. In the present embodiment, the health information includes a sleep index representing an index related to user's sleep, and a fatigue index representing an index related to fatigue of the user. Thus, the terminal system 1 senses the biological information of a user, calculates the sleep index and the fatigue index based on the result of sensing, and uploads the indexes to the data server 2. The terminal system 1 senses a health state of a user, and can be also called a QOL (Quality of Life) sensor.

The data server 2 stores (accumulates) the health information, of the user, which is transmitted from the terminal system 1. Further, the data server 2 calculates statistics (for example, an average value in a predetermined period) as secondary information obtained from the health information. In the following description, the health information received from the terminal system 1 and the secondary information (statistics) obtained from the health information may be generically referred to as health information.

The service server 3 uses the health information stored in the data server 2 to provide various information to the user of the terminal system 1. In the following description, information provided to the user by the service server is referred to as "provision information". The provision information is information for improving an index indicated by the health information of a user. The provision information is, for example, information for introducing a product or a service (for example, goods for improving sleep, a supplement for recovery from fatigue, or the like) for improving the index, and the details thereof will be described below. That is, in the present embodiment, the provision information may be also called recommendation information for a user. The service server 3 performs a service for providing the provision information by using the health information obtained from the data server 2. Further, in the present embodiment, the service server 3 also provides a service for selling, to a user, a product and/or a service (hereinafter, referred to as "product/service") which is introduced by the provision information.

Note that the data server 2 and the service server 3 each include one or more information processing devices (i.e., server devices) having a CPU and a memory. On each of the servers 2 and 3, the CPU executes an information processing program stored therein using the memory, thereby executing various information processes. In the present specification, the "server" not only means one information processing device (server device), but also means the entirety of a server device group (server system) when the server includes a plurality of server devices.

[2. Configuration of Terminal System]

Figure 2:
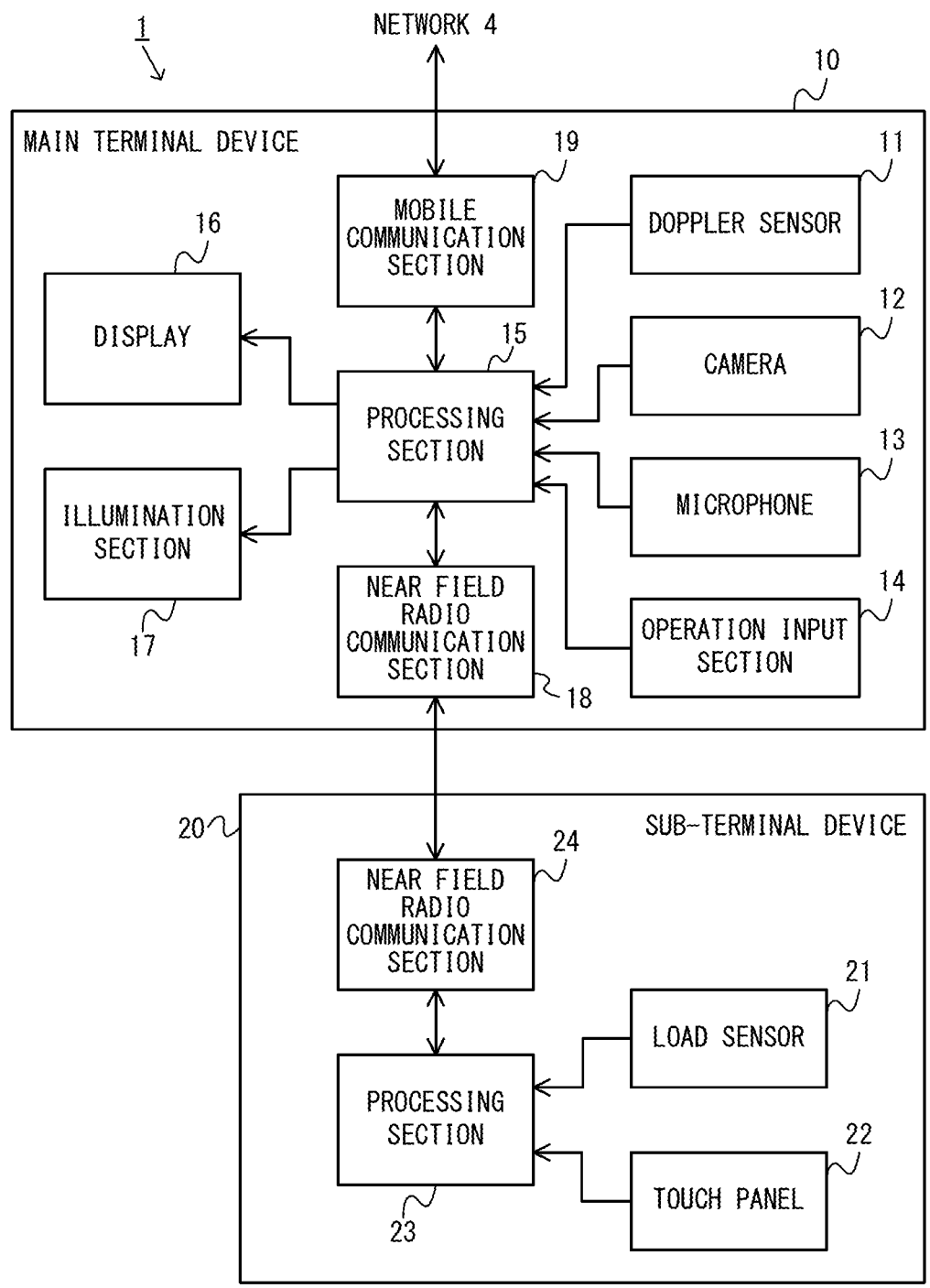
FIG. 2 illustrates an example of a configuration of a terminal system.
Figure 3:
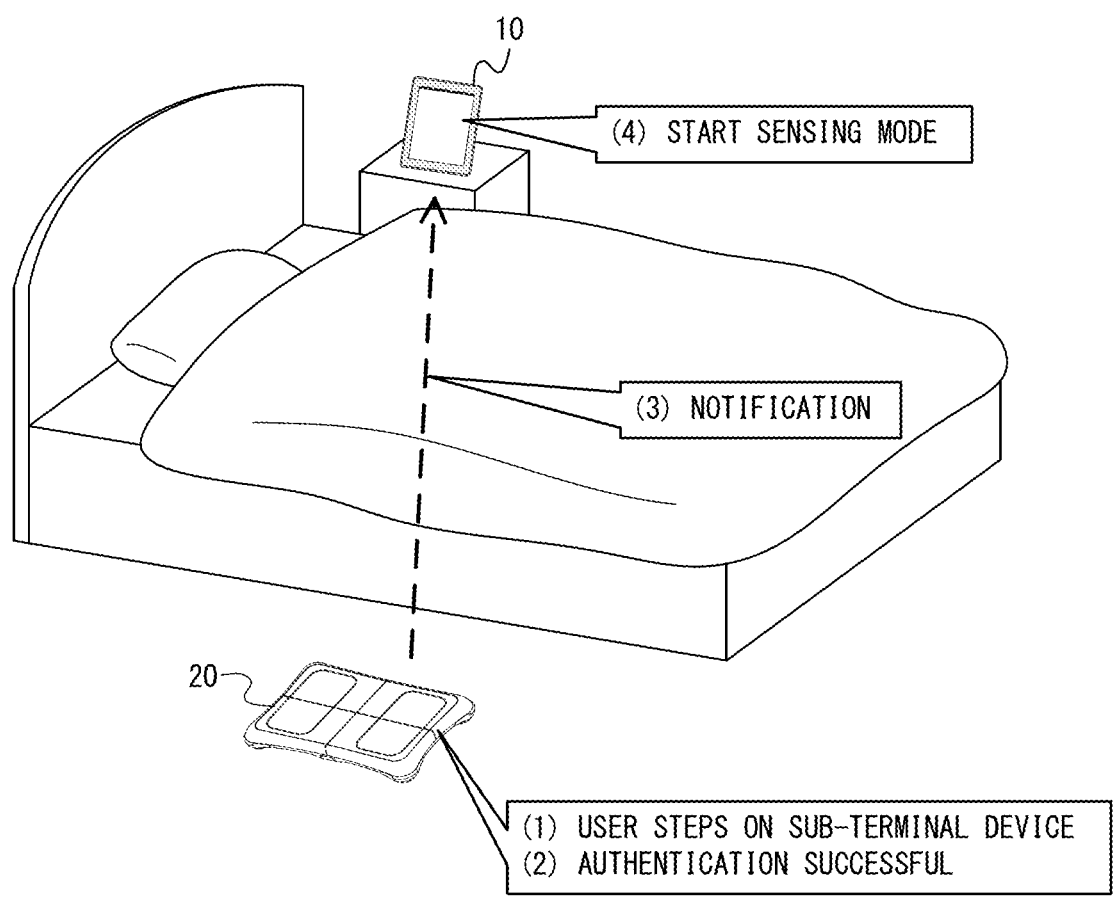
FIG. 3 illustrates an example of an arrangement of devices included in the terminal system.

Next, a configuration of the terminal system 1 according to the present embodiment will be described. FIG. 2 illustrates an example of the configuration of the terminal system 1. FIG. 3 illustrates an exemplary case where devices included in the terminal system 1 are disposed. As shown in FIG. 2 and FIG. 3, the terminal system 1 includes a main terminal device 10 and a sub-terminal device 20. In the present embodiment, the main terminal device 10 and the sub-terminal device 20 are disposed in, for example, a use's bedroom (see FIG. 3). The terminal system 1 mainly obtains the biological information while the user is in bed (sleeping), and calculates the sleep index and the fatigue index, and the details thereof will be described below.

The main terminal device 10 functions as a sensor for sensing the biological information. In the present embodiment, as shown in FIG. 3, the main terminal device 10 is disposed near a user such as at a user's bedside, and senses the biological information from the user who is in bed.

As shown in FIG. 2, the main terminal device 10 includes a Doppler sensor 11 which is an example of a sensor for sensing the biological information. The Doppler sensor 11 emits microwave and receives reflected wave of the emitted microwave, thereby sensing a moving body on the basis of a difference between a frequency of the emitted microwave and a frequency of the received microwave. An output waveform, from the Doppler sensor 11, which represents the biological information having been sensed, is analyzed (subjected to frequency analysis or the like), whereby the biological information such as respiration, pulse, or body motion can be further calculated. The detail thereof will be described below. In the present embodiment, a non-worn type sensor (Doppler sensor 11) capable of sensing the biological information in a state where the user does not wear the sensor is used, whereby the biological information can be sensed without hindering the user (without preventing the user from sleeping).

The main terminal device 10 includes a camera 12. The camera 12 is used to take an image of the user. Further, the main terminal device 10 includes a microphone 13. The microphone 13 is used to sense, for example, sound (snore or the like) from the user and/or ambient noise.

The main terminal device 10 includes a processing section 15 for executing various information processing to be executed by the main terminal device 10. The processing section 15 is connected to components 11 to 14 and 16 to 19 of the main terminal device 10. The processing section 15 has a CPU (Central Processing Unit) and a memory, and the CPU uses the memory to execute an information processing program stored in the main terminal device 10, whereby the various information processing described above is executed. In the present embodiment, the processing section 15 executes, as the information processing, a process of calculating the health information on the basis of the biological information sensed by the sensor, and the like. Further, when the main terminal device 10 has a function as the information processing device (information processing terminal), the processing section 15 executes various information processing for the function.

The main terminal device 10 includes an input/output interface, and functions as an information processing device (input/output terminal) for inputting and viewing of information. Specifically, the main terminal device 10 includes an operation input section 14 and a display 16. The operation input section 14 is any input device that receives operation input from a user. In the present embodiment, the main terminal device 10 has, as the operation input section 14, a button, and a touch panel provided on the display 16. The display 16 is capable of displaying the biological information and/or the health information of a user, and displaying the provision information described above. Further, the display 16 may function as a mirror.

The main terminal device 10 includes an illumination section 17 having a light source such as a LED. Light emission from the illumination section 17 is controlled by the processing section 15. For example, the illumination section 17 may be controlled so as to appropriately emit light according to a sleep state while the user is sleeping, or emit light so as to act as an alarm clock for causing the user to wake up.

The main terminal device 10 and the sub-terminal device 20 can communicate with each other. In an exemplary case, the main terminal device 10 has a short-range wireless communication section 18 as communication means for communicating with the sub-terminal device 20. In the present embodiment, the short-range wireless communication section 18 is a communication module having a function of performing communication using a wireless LAN. For example, the short-range wireless communication section 18 is a communication module certified by Wi-Fi.

Further, the main terminal device 10 is connected to the network 4, and has a function of communicating with the servers 2 and 3. Specifically, the main terminal device 10 includes a mobile communication section 19. In the present embodiment, the mobile communication section 19 is a communication module that has a function of connecting to a mobile communication network and performing communication. For example, the mobile communication section 19 performs communication in a communication mode that complies with the 3G communication standard or the 4G (including LTE (Long Term Evolution)) communication standard. The method in which the main terminal device 10 communicates with the servers 2 and 3 may be a method in which communication is performed via a wireless LAN by a communication module certified by Wi-Fi. Further, the main terminal device 10 may have both a function of communicating with the servers 2 and 3 via a mobile communication network, and a function of communicating with the servers 2 and 3 via a wireless LAN.

The sub-terminal device 20 functions as a sensor for obtaining biological information different from that obtained by the main terminal device 10. As shown in FIG. 3, the sub-terminal device 20 is disposed near the main terminal device 10. The sub-terminal device 20 is capable of sensing the biological information (body weight or the like) of a user who has stepped thereon.

As shown in FIG. 2, the sub-terminal device 20 includes a load sensor 21. The load sensor 21 senses a load applied to the top surface of the sub-terminal device 20. The sub-terminal device 20 may have a sensor for sensing the biological information, other than a body weight, for measuring body fat or the like.

Further, the sub-terminal device 20 includes a touch panel 22. The touch panel 22 is disposed on the top surface of the sub-terminal device 20. The touch panel 22 is capable of sensing the shape of a foot of a user who has stepped on the top surface of the sub-terminal device 20.

The sub-terminal device 20 includes a processing section 23 that executes various information processing to be executed by the sub-terminal device 20. The processing section 23 has a CPU (Central Processing Unit) and a memory, and the CPU uses the memory to execute an information processing program stored in the sub-terminal device 20, thereby executing various information processing.

The sub-terminal device 20 includes a short-range wireless communication section 24 as communication means for communicating with the main terminal device 10. Similarly to the short-range wireless communication section 18 of the main terminal device 10, the short-range wireless communication section 24 is a communication module that has a function of performing communication using a wireless LAN, and is, for example, a communication module certified by Wi-Fi. In the present embodiment, when it is sensed that a user has stepped on the sub-terminal device 20, the short-range wireless communication section 24 transmits a predetermined notification signal and the biological information sensed by the load sensor 21, from the sub-terminal device 20, to the main terminal device 10.

[3. Process Operation by Terminal System]

Next, a process operation executed by the terminal system 1 will be described. In the present embodiment, the main terminal device 10 operates in three kinds of modes, that is, in a normal mode, a sensing mode, and a sleep mode. In the normal mode, the main terminal device 10 is used as an input/output terminal, and receives an operation input from a user, executes processing according to the operation input, and displays an image of a result of the processing on the display 16. In the sensing mode, the biological information of a user who is in bed is sensed, and the health information is calculated. In the sleep mode, the above-described processes to be executed in the normal mode and the sensing mode are not executed, and power consumption is reduced. However, also in the sleep mode, the main terminal device 10 is allowed to receive a signal from the sub-terminal device 20.

The sub-terminal device 20 is capable of constantly performing sensing as to whether or not a user has stepped on the sub-terminal device 20. That is, in the sub-terminal device 20, at least one of the load sensor 21 and the touch panel 22 is constantly actuated, to sense that a user has stepped on the sub-terminal device 20. In other embodiments, the sub-terminal device 20 may be operable in a sleep mode and an ON mode (in which at least the processing section 23 operates). In the sleep mode, the processing section 23 does not operate, and at least one of the load sensor 21 and the touch panel 22 operates. In the ON mode, at least the processing section 23 operates. In this case, when the load sensor 21 and/or the touch panel 22 sense that a user has stepped on the sub-terminal device 20 in a state where the sub-terminal device 20 is in the sleep mode, the mode may be shifted to the ON mode.

(Process in Sensing Mode)

Hereinafter, processing performed when the terminal system 1 operates in the sensing mode while a user is in bed, will be described. It is assumed that, before the user goes to bed, the main terminal device 10 is in the sleep mode or the normal mode. At this time, when the user has stepped on the sub-terminal device 20 (see (1) shown in FIG. 3), the processing section 23 of the sub-terminal device 20 senses that the user has stepped on the sub-terminal device 20, and measures the body weight on the basis of a result of sensing from the load sensor 21. Further, the processing section 23 calculates the shape of a foot of the user on the basis of a result of sensing from the touch panel 22. In other embodiments, the sub-terminal device 20 may include a camera, and the processing section 23 may calculate the shape of the foot on the basis of an image taken by the camera.

In the present embodiment, the processing section 23 performs authentication of the user by using the calculated shape of the foot (see (2) shown in FIG. 3). That is, data indicating the shape of the foot of an authenticated user is previously registered (stored) in the sub-terminal device 20, and the processing section 23 determines whether or not the calculated shape of the foot and the registered shape of the foot coincide with each other, thereby performing authentication. When it is determined that the two shapes of the feet coincide with each other, the processing section 23 determines that the authentication has succeeded. In this case, the processing section 23 transmits a predetermined authentication notification to the main terminal device 10 (see (3) shown in FIG. 3). The processing section 23 may transmit, to the main terminal device 10, both the authentication notification and the biological information (information on a body weight or the like) sensed by the sub-terminal device 20. Meanwhile, when it is determined that the two shapes of the feet do not coincide with each other, the processing section 23 determines that authentication has failed. In this case, the processing section 23 does not transmit the authentication notification to the main terminal device 10.

When the main terminal device 10 receives the authentication notification, the main terminal device 10 shifts from the sleep mode or the normal mode to the sensing mode (see (4) shown in FIG. 3). Thereafter, the biological information of the user is obtained by the main terminal device 10.

When the sensing mode is started, the processing section 15 of the main terminal device 10 firstly actuates a sensor (Doppler sensor 11 in the present embodiment) for sensing the biological information, and starts obtaining a result of sensing from the sensor. When the camera 12 and/or the microphone 13 are used as the sensor for sensing, the processing section 15 may actuate the camera 12 and/or the microphone 13. In the sensing mode, the Doppler sensor 11 continuously performs the sensing, and continuously outputs an output waveform as the result of sensing. The processing section 15 calculates the health information (sleep index and fatigue index) based on the result of sensing (output waveform) from the Doppler sensor 11.

(Calculation of Health Information)

Figure 4:
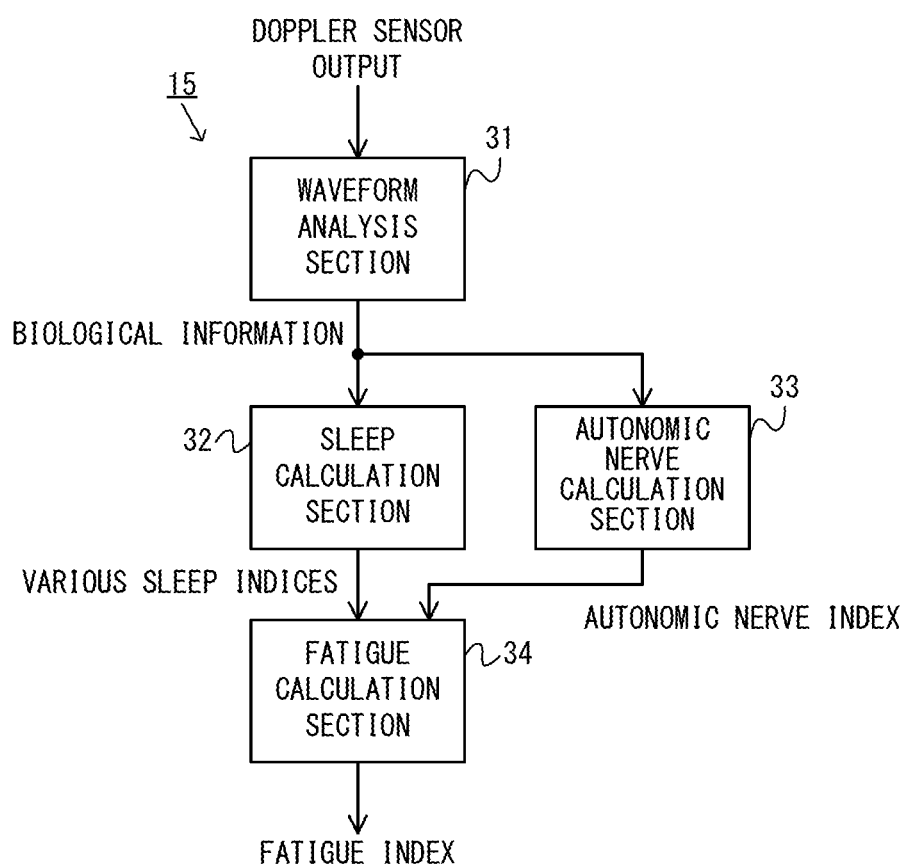
FIG. 4 is a functional block diagram illustrating an example of a functional configuration for calculating health information by a processing section of a main terminal device.

Hereinafter, the process of calculating the health information (sleep index and fatigue index) on the basis of the result of sensing from the Doppler sensor 11 will be described. FIG. 4 is a functional block diagram illustrating an example of a functional configuration for calculating the health information by the processing section 15. As shown in FIG. 4, the processing section 15 includes a waveform analysis section 31, a sleep calculation section 32, an autonomic nerve calculation section 33, and a fatigue calculation section 34.

The waveform analysis section 31 calculates respiration, pulse, and body motion as further biological information on the basis of the biological information (output waveform) sensed by the Doppler sensor 11. To date, it has been known that the output waveform from the Doppler sensor 11 is separated according to frequencies, whereby waveforms representing respiration, pulse, and body motion can be obtained. The waveform analysis section 31 separates the output waveform into a frequency band corresponding to the respiration, a frequency band corresponding to the pulse, and a frequency band corresponding to the body motion, by performing frequency analysis and the like, and outputs the data of each waveform obtained by the separation. As shown in FIG. 4, the output from the waveform analysis section 31 is inputted to each of the sleep calculation section 32 and autonomic nerve calculation section 33.

The sleep calculation section 32 calculates various sleep indexes on the basis of the biological information (respiration, pulse, and body motion). To date, a method for calculating sleep indexes on the basis of respiration, pulse, and body motion has been known. In the present embodiment, the sleep calculation section 32 calculates sleep indexes indicating the following information.

sleep latency (sleep onset latency)
WASO (Wake Time After Sleep Onset) (in other words, amount of time of mid-sleep awakenings)
number of mid-sleep awakenings
sleep efficiency
total sleep time
activity level during sleep
sleep stage
REM sleep time
non-REM sleep time
sleep quality In other embodiments, a portion of the sleep indexes described above may be calculated, or different kinds of sleep indexes other than the sleep indexes descried above may be calculated.

The autonomic nerve calculation section 33 calculates an index (autonomic nerve index) indicating an action level of autonomic nerves (sympathetic nerves and parasympathetic nerves) on the basis of the biological information. Specifically, a waveform of a pulse (RR-interval) included in the biological information is subjected to frequency analysis by using the maximum entropy method and Fourier transformation, and a high-frequency component (about 0.15 to 0.40 [Hz]) HF and a low-frequency component (about 0.04 to 0.15 [Hz]) LF of the waveform are calculated. It has been known that the high-frequency component HF represents an action level of parasympathetic nerves, and the low-frequency component LF represents an action level of sympathetic nerves. Further, it has been known that a fatigue level can be evaluated on the basis of a ratio between an action level of parasympathetic nerves and an action level of sympathetic nerves (see, for example, Japanese Laid-Open Patent Publication No. 2010-201113). Therefore, the autonomic nerve calculation section 33 calculates, as the autonomic nerve index, a ratio (LF/HF) of the low-frequency component LF to the high-frequency component HF. As shown in FIG. 4, the output from the autonomic nerve calculation section 33 is used as an input to the fatigue calculation section 34.

The fatigue calculation section 34 calculates a fatigue index on the basis of the sleep index and the autonomic nerve index. In the present embodiment, as the fatigue index, the degrees of fatigue represented as five stages from fatigue degree (level) 1 to fatigue degree 5 are calculated. There is no particular limitation on the method for calculating the fatigue index. For example, the following method can be used.

A first method is a method in which a fatigue index is calculated according to a sleep index. The sleep index is considered to have a correlation with a fatigue level. For example, an exemplary case in which the fatigue level is assumed to be high is as follows.

The sleep latency is long.

WASO is long.

The number of mid-sleep awakenings is high.

The sleep efficiency is poor.

The total sleep time is short.

The balance between the REM sleep hours and the non-REM sleep hours is poor (the ratio between REM sleep hours and non-REM sleep hours is outside a normal range).

Therefore, the fatigue calculation section 34 calculates the fatigue level so as to increase the fatigue level when the sleep index represents the above-described case, and reduce the fatigue level when the sleep index does not represent the above-described case. For example, the fatigue calculation section 34 may determine whether or not the above-described items are satisfied, calculate a point based on the number of satisfied items, and calculate the fatigue level on the basis of the total point. At this time, the fatigue calculation section 34 may perform weighting for each item to calculate the point. Alternatively, a reference value (for example, "six hours" for the total sleep hours) may be set for each item, and the point may be calculated such that the greater a difference between the calculated value of the sleep index and the reference value is, the greater the point is.

As described above, in the present embodiment, the sleep index for user's sleep is calculated on the basis of the biological information, and the fatigue index is calculated on the basis of the sleep index. As described above, since it is considered that there is a correlation between the sleep index and the fatigue degree, the fatigue index is calculated on the basis of the sleep index, whereby the fatigue index can be obtained with an enhanced accuracy.

A second method is a method in which a fatigue level is calculated on the basis of sleep hours in a predetermined time period (for example, one week). To date, there has been a method for calculating a fatigue level on the basis of sleep hours and a working time according to Fatigue Risk Management System (FRMS). In this method, for example, if the working time is assumed to be constant for simplicity, the fatigue level can be calculated (merely) on the basis of the sleep hours.

A third method is a method for calculating a fatigue level on the basis of the autonomic nerve index. As described above, it has been known that a fatigue level can be evaluated by using a balance between an action level of sympathetic nerves and an action level of parasympathetic nerves, that is, by using the autonomic nerve index described above. Therefore, the fatigue calculation section 34 calculates a fatigue level such that, for example, the greater a difference between the reference value and a value of the autonomic nerve index is, the higher the fatigue level is.

In the present embodiment, the fatigue calculation section 34 calculates a fatigue level by using the above three methods. Specifically, the fatigue calculation section 34 calculates the degrees of fatigue in the above three methods, and calculates a final fatigue level on the basis of the calculated degrees of fatigue. For example, the fatigue calculation section 34 may use an average of the three values of the fatigue level as the final fatigue level, or may calculate the final fatigue level by performing weighting of any one of the three values of the fatigue level.

In other embodiments, there is no particular limitation on the method for calculating the fatigue index, and the content of the fatigue index may be also optionally set. In other embodiments, a value indicating a fatigue degree for each fatigue type may be calculated as the fatigue index. For example, in another embodiment, the fatigue index may represent three kinds of values that are a value representing an acute-fatigue degree, a value representing a cumulative-fatigue degree, and a value representing mental-fatigue degree.

In other embodiments, the health information may be calculated by using a result of sensing from the camera 12 and/or the microphone 13. For example, the biological information such as pulse and/or body motion may be calculated on the basis of an image of a user which is taken by the camera 12. Therefore, the processing section 15 may calculate the sleep index (and the fatigue level) by using the biological information obtained from an image taken by the camera 12 in addition to (or instead of) the biological information obtained from a result of sensing from the Doppler sensor 11. Further, the processing section 15 may calculate the sleep index in consideration of snore sensed by the microphone 13.

Figure 5:
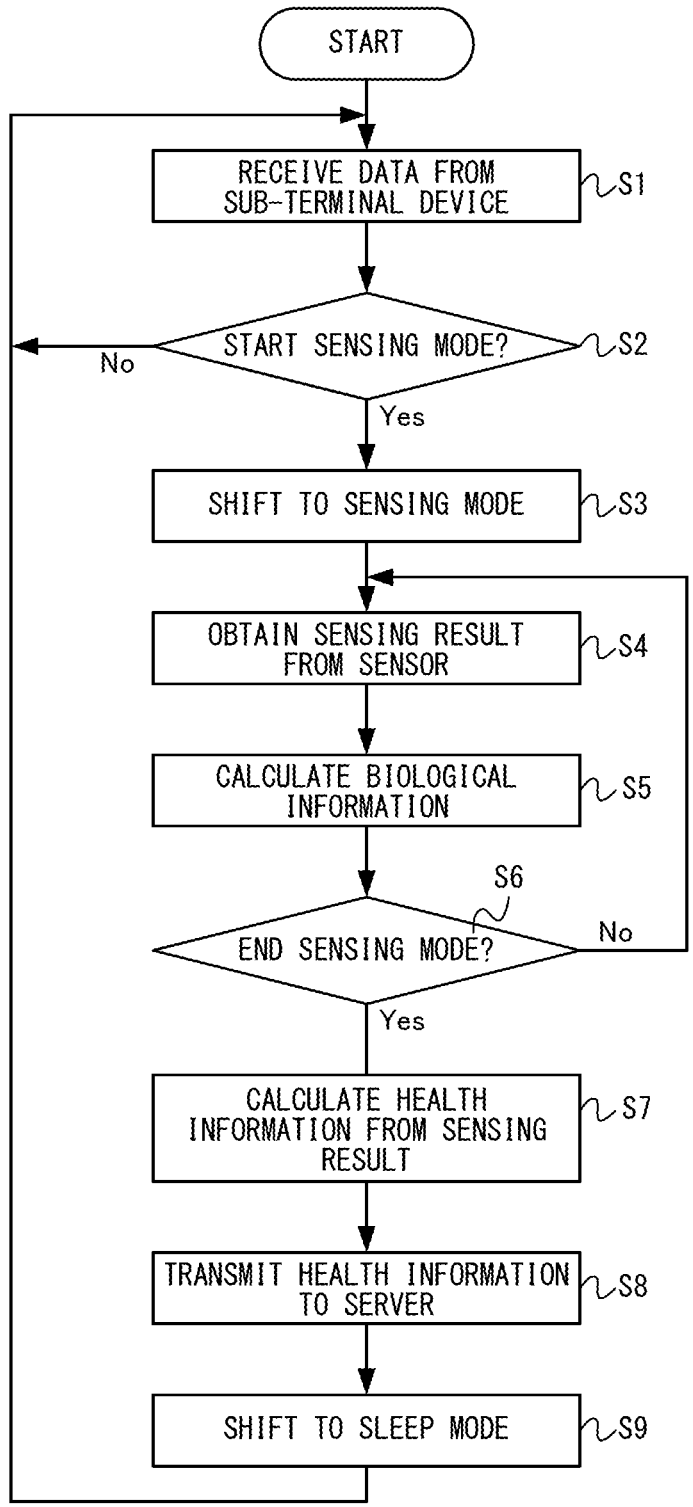
FIG. 5 is a flow chart showing an example of a flow of a process executed by the processing section of the main terminal device.

FIG. 5 is a flow chart showing an example of a flow of a process executed by the processing section 15 of the main terminal device 10. FIG. 5 mainly shows the process in the sensing mode, and the processes in the normal mode and the sleep mode are not shown.

In the present application, the processes of steps in the flow charts shown in the drawings (FIG. 5, FIG. 16, FIG. 17 and FIG. 32) are merely examples, and the order in which the steps are performed in the process may be changed or another process in addition to (or instead of) the process of the steps may be executed when the same result is obtained. In the description herein, the CPU of the processing section executes the process of the steps in the flow chart. A processor or a dedicated circuit other than the CPU may execute the process of a part of the steps in the flow chart.

In step S1 shown in FIG. 5, the processing section 15 confirms reception of data from the sub-terminal device 20. At a time when step S1 is executed, the main terminal device 10 is in the sleep mode or the normal mode. In the sleep mode or the normal mode, the processing section 15 repeatedly executes the process steps of step S1 (and S2) once in every predetermined time period.

In step S2, the processing section 15 determines whether or not the mode is to be shifted to the sensing mode. That is, the processing section 15 determines that mode is to be shifted to the sensing mode when the above-described authentication notification is received from the sub-terminal device 20 in step S1, and determines that the mode is not shifted to the sensing mode when the authentication notification is not received. When the result of the determination in step S2 is affirmative, the process step of step S3 is executed. Meanwhile, when the result of determination in step S2 is negative, the process step of step S1 is executed again.

In step S3, the processing section 15 shifts the operation mode of the main terminal device 10 to the sensing mode. That is, the processing section 15 actuates the Doppler sensor 11. In the following step S4, the processing section 15 obtains a result of sensing from the Doppler sensor 11. Further, in the following step S5, the processing section 15 calculates, as the further biological information, respiration, pulse, and body motion on the basis of the result of sensing.

In the sensing mode, a series of process steps from step S4 to S6 is repeatedly executed once in every predetermined time period. Therefore, in the sensing mode, the biological information is repeatedly obtained (calculated) and is successively stored in a memory of the processing section 15.

In step S6, the processing section 15 determines whether or not the sensing mode is to be ended. In the present embodiment, whether or not the sensing mode is to be ended is determined according to whether or not a user is in bed. Specifically, the processing section 15 determines whether or not the user is outside the range for sensing by the Doppler sensor 11, on the basis of the result of sensing from the Doppler sensor 11. When the user is outside the range, the processing section 15 determines that the user is not in bed, and the sensing mode is to be ended. Meanwhile, when the user is in the range for the sensing by the Doppler sensor 11, the processing section 15 determines that the user is in bed, and the sensing mode is not to be ended. When a result of the determination in step S6 is affirmative, the process step of step S7 is executed. Meanwhile, when a result of the determination in step S6 is negative, the process step of step S4 is executed again.

In step S7, the processing section 15 calculates the health information on the basis of the result of sensing from the Doppler sensor 11. That is, as described above in "(Calculation of health information)", the sleep index and the fatigue index are calculated on the basis of the biological information. In the following step S8, the processing section 15 transmits, to the data server 2, the health information calculated in step S7. Thus, in the present embodiment, the health information is automatically (does not request user's operation) generated and transmitted to the data server 2. In other embodiments, information to be transmitted from the terminal system 1 to the data server 2 may be transmitted according to a user performing an operation for transmission. Furthermore, the processing section 15 may transmit, to the data server 2, both the health information, and the information (biological information such as a body weight) received together with the authentication notification from the sub-terminal device 20.

In step S9, the processing section 15 shifts the operation mode of the main terminal device 10 to the sleep mode. That is, the processing section 15 halts the operation of the Doppler sensor 11. After the operation mode has been shifted to the sleep mode in step S9, the process step of step S1 described above is executed again.

As described above, in the present embodiment, the process of calculating the health information on the basis of the biological information that is a result of sensing from the sensor (the Doppler sensor 11) is executed on the terminal (terminal system 1) side. However, this process may be shared by the terminal side and the server side in any manner. For example, in another embodiment, the terminal system 1 may transmit the biological information to the data server 2, and the data server 2 may calculate the health information on the basis of the biological information. At this time, some health information (for example, sleep hours or sleep efficiency) may be calculated also by the terminal system 1, and may be displayed on the display 16 at an appropriate time. Thus, the terminal system 1 can provide the health information to the user without obtaining data from the data server 2. Further, the health information calculated by the data server 2 may be transmitted to the terminal system 1 and displayed by the terminal system 1.

In the present embodiment, the health information is transmitted from the terminal system 1 to the data server 2 when the sensing mode ends. In other embodiments, the transmission information (the biological information and/or the health information) to be transmitted from the terminal system 1 to the data server 2 may be successively transmitted during the sensing mode.

(Process in Normal Mode)

In the present embodiment, the main terminal device 10 shifts to the normal mode according to a user performing a predetermined operation (for example, an operation of pressing a predetermined power button) in the sleep mode. The main terminal device 10 accesses the service server 3 and displays the health information of the user on the display 16 or displays, on the display 16, the provision information provided by the service server 3 in the normal mode, and the detail thereof will be described below. Further, the main terminal device 10 shifts to the sleep mode according to a user performing a predetermined operation (for example, an operation of pressing the predetermined power button) in the normal mode.

(Function and Effect by Terminal System)

As described above, in the present embodiment, the terminal system includes: a first device (main terminal device 10) having a first sensor (Doppler sensor 11) for sensing first biological information for a user: and a second device (sub-terminal device 20) having a second sensor (load sensor 21) for sensing second biological information that is the biological information for the user and is different from the first biological information. Further, the terminal system is capable of communicating with a server (data server 2) for performing analysis based on the first biological information and the second biological information.

The terminal system transmits, to the server (data server 2), transmission information that includes at least one of: the first biological information and the second biological information; and the health information obtained from the biological information. The first biological information (and the health information based thereon) and the second biological information (the health information based thereon) may be transmitted individually from different devices, respectively. The server performs analysis based on the transmission information transmitted from the terminal system.

Thus, the terminal system is capable of obtaining a lot of the biological information from two devices, thereby improving the quality of analysis by the server. That is, the server is allowed to perform increased kinds of analyses or perform analysis with enhanced accuracy.

In the present embodiment, the first sensor (Doppler sensor 11) senses the biological information of a user who is in bed, and the second sensor (the load sensor 21) senses the biological information of a user who stays awake (for example, before going to bed and after wake-up). Thus, the biological information can be obtained both while the user is in bed and during the other period, thereby improving the quality of analysis by the server.

In the present embodiment, the first sensor is a non-contact type sensor capable of sensing the biological information in a state where a user is not in contact with the sensor, and the second sensor is a contact-type sensor capable of sensing the biological information in a state where a user is in contact with the sensor. Thus, the biological information can be sensed without making the user conscious of the sensing while the user is in bed, and the biological information can be assuredly sensed while the user stays awake.

In the present embodiment, the first device has the following means.

Reception means for receiving, from the second device, the second biological information sensed by the second sensor Transmission means for transmitting, to the server (data server 2), transmission information that includes at least one of: the first biological information sensed by the first sensor and the second biological information received from the second device; and the health information based on the above biological information.

In the above configuration, the biological information sensed by the two devices (and/or the health information) can be efficiently transmitted to the server. Further, the second device may not have a function of communicating with the server, thereby simplifying the configuration of the device.

In the present embodiment, the server (the service server 3) transmits, to the terminal system, the information (provision information described below) based on a result of analysis, and the detail thereof will be described below. The first device includes: reception means for receiving information transmitted from the server; and display means for displaying the received information. Thus, the user is allowed to easily view the above information by using the first device. Further, the above information is displayed by the first device that senses the biological information, thereby simplifying the configuration of the terminal system.

In other embodiments, the terminal system 1 may have a device (information terminal) for receiving and displaying the provision information, separately from the main terminal device 10. For example, the information terminal may be any information processing device, such as a mobile terminal, a personal computer, and a game apparatus, used by a user. For example, the information terminal of the user may access the service server 3, and receive and display the provision information. Further, purchasing of the product/service described below may be performed by using the information terminal.

In the present embodiment, the second device transmits a predetermined notification (authentication notification) to the first device according to the second biological information being sensed. The first device starts sensing the first biological information according to the predetermined notification being received. Thus, the first device can efficiently execute the operation of sensing the biological information, and information processing can be efficiently performed by the first device. Further, power consumption in the first device can be reduced.

In the present embodiment, the second device executes, according to the second biological information being sensed, the authentication process for the user by using the biological information (the shape of the foot sensed by the touch panel 22) of the user. When the authentication has succeeded (that is, one user among one or more users that are previously registered is authenticated in the authentication process), the second device transmits the predetermined notification to the first device. Thus, when the user is authenticated as one of the registered users, the first device starts sensing the biological information, whereby the sensing process can be efficiently executed. When the number of registered users is plural, a user for whom sensing is to be performed can be identified. The biological information used in the authentication process may be the second biological information or other biological information.

In the present embodiment, the main terminal device 10 starts measuring (sensing) the biological information if the authentication has succeeded in the sub-terminal device 20, and ends measurement of the biological information if the biological information is not sensed (the user is not sensed). In other embodiments, there is no particular limitation on the method for determining a period in which the biological information is measured, and the measurement period may be determined in another method.

For example, in another embodiment, in the main terminal device 10, sensing may be intermittently performed by the sensor (Doppler sensor 11) and the measurement period may be determined on the basis of the result of sensing. Specifically, the main terminal device 10 determines whether or not a user is sensed (whether or not a user is in a range for sensing), by the Doppler sensor 11 performing sensing at predetermined time intervals. When a user is not sensed, the main terminal device 10 halts sensing by the Doppler sensor 11. In this case, the measurement is not started. Meanwhile, when a user is sensed, the main terminal device 10 continues the sensing by the Doppler sensor 11, thereby starting the measurement. Further, when the measurement has been started, the main terminal device 10 continues the measurement while a user is sensed by the Doppler sensor 11. That is, similarly to the above embodiment, the main terminal device 10 ends the measurement by the Doppler sensor 11 according to the user being not sensed. Thus, the period for the measurement by the Doppler sensor 11 can be determined on the basis of a result of sensing (intermittently performed) by the Doppler sensor 11 itself. Thus, the measurement period can be determined without using a device such as another sensor, thereby simplifying the configuration of the device.

In other embodiments, the period for the measurement by the Doppler sensor 11 may be determined on the basis of a result of sensing from a sensor (for example, human sensor) different from the Doppler sensor 11. For example, the terminal system 1 may use an infrared sensor and/or a camera as the human sensor. Specifically, the terminal system 1 intermittently or continuously senses a user by the human sensor. In a period in which a user is sensed by the human sensor, the terminal system 1 performs the measurement by the Doppler sensor 11. Also in this manner, the period for the measurement can be automatically determined, similarly to the method of the present embodiment, and to a method for determining a period for the measurement on the basis of a result of sensing by the Doppler sensor 11. That is, since a user need not perform an operation for (start and end of) measurement, usability of the terminal system 1 can be improved. Furthermore, the biological information can be measured without causing a user to spend time and putting a burden on the user. Therefore, continuous obtaining of the biological information is facilitated.

In other embodiments, the period for the measurement by the Doppler sensor 11 may be previously determined. For example, the terminal system 1 may perform the measurement in a predetermined time slot (for example, a time slot from 8:00 p.m. to 10 a.m. of the immediately following morning), or the measurement may be constantly performed (as long as a user does not perform an operation for halting). Also in this manner, similarly to the above manner, the user need not perform an operation for starting and ending the measurement, whereby usability of the terminal system 1 can be improved.

In the above embodiment, the terminal system 1 automatically (in other words, even if a user does not perform a specific operation) calculates the health information (sleep index and fatigue index) on the basis of the biological information in addition to the biological information being automatically measured. Therefore, even if a user does not perform a specific operation, the health information is calculated by the terminal system 1, whereby usability of the terminal system 1 can be improved.

In the present embodiment, the first device that is a single device includes first communication means (mobile communication section 19) for communicating with the server via a mobile telephone communication network, and the second communication means (short-range wireless communication section 18) for performing short-range wireless communication with the second device. The first device is capable of easily communicating with the server and the second device.

As described above, in the present embodiment, the terminal system 1 uses a non-contact type sensor (Doppler sensor), whereby a user need not wear a sensor. Since the biological information is automatically measured while the user is in bed, the user need not wait for measurement of the biological information, and need not perform a bothersome operation for measurement. Further, when the sensor is disposed near the user who is in bed, a bothersome setting operation need not be performed for each measurement. Thus, the terminal system 1 can measure the biological information without causing the user to spend time and putting a burden on the user, whereby continuous obtaining of the biological information is facilitated.

The terminal system 1 may reproduce content (such as music) for inducing sleep onset or wake-up (awakening) of a user. For example, the main terminal device 10 may reproduce music for inducing sleep onset of the user according to start of sensing by the Doppler sensor 11. At this time, the main terminal device 10 may control reproduction of the content according to a sleep state of the user. Thus, the content can be reproduced in an appropriate method based on the sleep state of the user, and the content can be effectively reproduced. Reproduction of the content is halted in a state where the effect seem to be small (for example, in a state where the user is deep in sleep), thereby reducing power consumption. Hereinafter, a specific exemplary case will be described.

The main terminal device 10 determines a sleep state of a user on the basis of a result of sensing (biological information) from the Doppler sensor 11 while the user is sleeping. For example, the main terminal device 10 determines, in real time, whether or not the user is in a sleep state, and determines, in real time, the depth of sleep (for example, whether the user is in REM sleep or non-REM sleep). The "determines in real time" described above strictly means that determination is immediately performed and also means that the determination is performed with about several seconds delay.

The main terminal device 10 controls reproduction of the content according to the sleep state, of the user, which is determined while the user is sleeping. The main terminal device 10 may control reproduction of the content/halting of reproduction of the content according to the sleep state, or may control the reproduction method (for example, sound volume and/or reproduction speed) according to the sleep state. For example, the main terminal device 10 may start reproduction of the content for causing a user to sleep before the user sleeps, and halt the reproduction of the content according to the user having fell asleep. Alternatively, the main terminal device 10 gradually reduces a sound volume for reproduction of the content according to the user having fell asleep, and halts reproduction of the content according to the user having been deep in sleep (for example, the user is in a non-REM sleep state). Further, for example, the main terminal device 10 may start reproduction of content (for example, content for causing the user to awaken) according to a time when the user has awakened, or may start reproduction of content according to a time when the user is assumed to awaken soon.

In the terminal system 1, the content reproduced when the user sleeps may be stored in the terminal system 1 or may be obtained from an external device (for example, the service server 3). For example, the service server 3 may transmit the content to the terminal system 1 in a providing process for providing the product/service (step S22 described below).

[4. Process Operation by Information Processing System]

Figure 6:
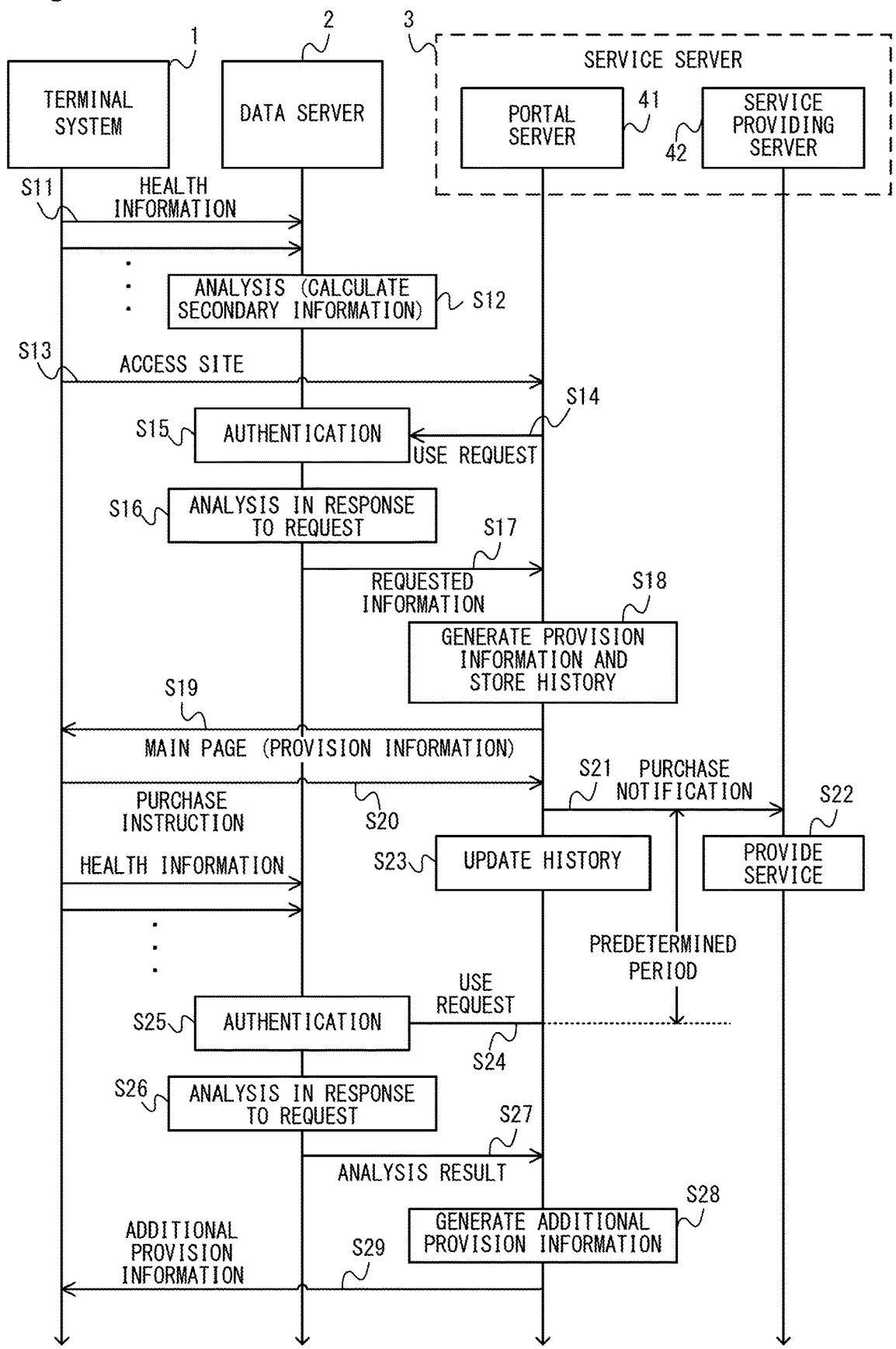
FIG. 6 is a timing chart showing an example of a flow of an operation performed by the information processing system.

Next, the process operation executed by the information processing system will be described. FIG. 6 is a timing chart showing an example of a flow of an operation performed by the information processing system. Hereinafter, a process operation performed when the information processing system generally performs the following operation will be described as an exemplary process operation.

<1> The health information obtained by the terminal system 1 is repeatedly transmitted to the data server 2, and stored and accumulated.

<2> The service server 3 generates provision information for introducing a product/service, by using the health information that is accumulated in the data server 2, and provides the provision information to the terminal system 1.

<3> A user who views the provision information in the terminal system 1, purchases the product/service introduced by the provision information (applies for use (enjoying) of the product/service when the product/service is available at no charge).

<4> After the product/service is purchased, the service server 3 generates additional provision information by using the health information accumulated in the data server 2, and provides the additional provision information to the terminal system 1.

In the present embodiment, the service server 3 includes a portal server 41 and a service providing server 42. The portal server 41 is a server that manages a portal site for providing, to the user, the health information accumulated in the data server 2, or the provision information described above. The portal server 41 has a function of accessing the data server 2, generating the provision information by using the health information accumulated in the data server 2, and providing the provision information to the user (the terminal system 1).

The service providing server 42 is a server that executes a process for providing the product/service to a user. In the present embodiment, purchasing of the product/service provided by the service providing server 42 is managed by the portal server 41. That is, the portal site functions as shopping site for selling the product/service provided by the service providing server 42. A user accesses the portal site by using the terminal system 1 and purchases the product/service on the portal site. The service providing server 42 is typically managed by a service provider that provides individual product/service, and the portal server 41 is managed by a management company that manages the data server 2. The service providing server 42 may include a plurality of servers for, for example, respective service providers.

<1> Process of Accumulating Health Information in Data Server

As described above in "[3. Process operation by terminal system]", the terminal system 1 transmits (uploads) the health information to the data server 2 (step S11 shown in FIG. 6). In the present embodiment, the terminal system 1 transmits both the health information and user identification information that is preset for each user. The terminal system 1 continuously transmits the health information periodically to the data server 2 (in the present embodiment, once a day), which is not shown in FIG. 6.

Figure 7:
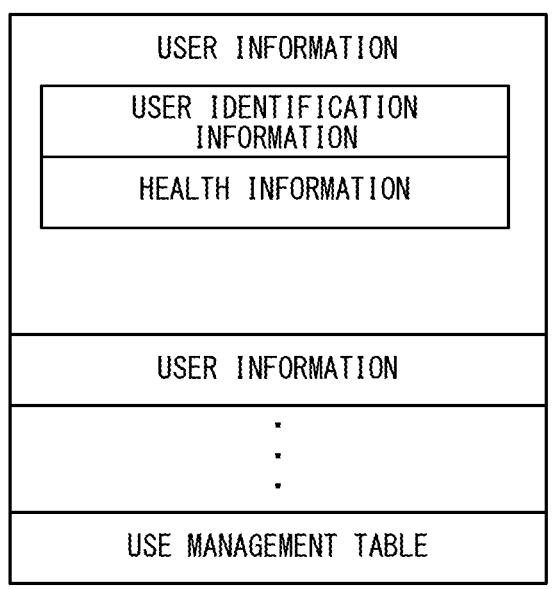
FIG. 7 illustrates an example of data stored in a data server.

The data server 2 stores, for each user, the health information received from the terminal system 1. FIG. 7 illustrates an example of data stored in the data server 2. As shown in FIG. 7, the data server 2 stores, for each user, user information including the user identification information and the health information. That is, when the health information is received from the terminal system 1 of a certain user, the data server 2 additionally stores the received health information in the health information in the user information for the certain user. Thus, the health information is accumulated in the data server 2.

The data server 2 calculates secondary information at an appropriate time on the basis of the received health information (step S12). That is, the data server 2 analyzes the health information to obtain the secondary information. As described above, in the present embodiment, the secondary information is information of a statistic calculated from the received health information. For example, when average sleep hours in one week are calculated as the secondary information, the data server 2 calculates the average sleep hours each time data of sleep hours in one week is accumulated. In the present embodiment, the secondary information is also accumulated as the health information in the data server 2.

As shown in FIG. 7, a use management table is stored in the data server 2. The use management table will be described below.

<2> Process of Providing Provision Information to Terminal System 1 by Service Server 3

The terminal system 1 accesses the portal site that is managed by the portal server 41 of the service server 3 according to an instruction from a user (step S13). That is, the user performs an operation of setting the main terminal device 10 so as to be in the normal mode and accessing the portal site. There is no particular limitation on the method for logging in the portal site, and may be similar to a conventional method. In the present embodiment, a login screen is displayed on the display 16, and the user inputs the user identification information and a password. The portal server 41 performs authentication by using the user identification information and the password. When the authentication has succeeded, (the user of) the terminal system 1 is allowed to log in the portal site.

In other embodiments, logging in the portal site may be performed by using personal authentication performed by the terminal system 1. For example, when the authentication has succeeded in the sub-terminal device 20, the main terminal device 10 is allowed to access and log in the portal site. At this time, the main terminal device 10 may not request a user to input the user identification information and the password.

When the user authentication has succeeded, the portal server 41 transmits a main page of the portal site to the terminal system 1, and the main page is displayed on the display 16. The main page includes the provision information to be provided to the user, and the detail thereof will be described below. Therefore, when the user authentication has succeeded, the portal server 41 executes a process of generating the provision information to be provided to the user (steps S14 to S18).

The content of the provision information is determined on the basis of the health information, of the user, stored in the data server 2. Therefore, the portal server 41 firstly makes a request (use request), to the data server 2, for use of the health information needed for determining the provision information (step S14). The health information requested in the use request is determined by using a provision condition table stored in the portal server 41.

Figure 8:
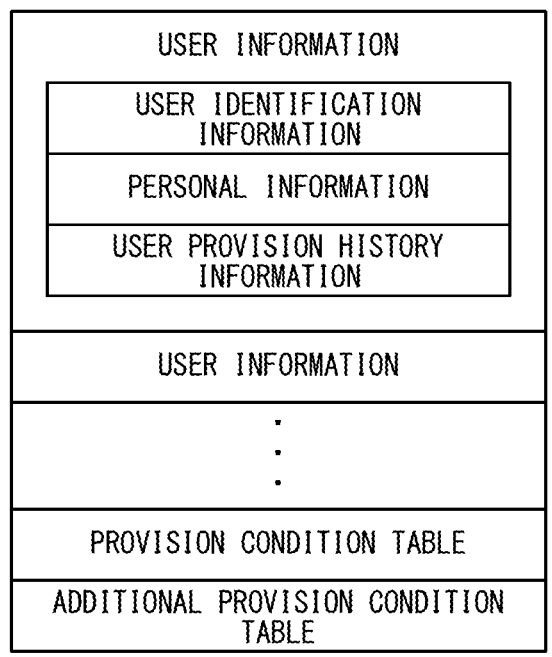
FIG. 8 illustrates an example of data stored in a portal server.

Data stored in the portal server 41 will be described. FIG. 8 illustrates an example of data stored in the portal server 41. As shown in FIG. 8, the portal server 41 stores, for each user, user information, a provision condition table, and an additional provision condition table. Firstly, the user information and the provision condition table associated with the process step of step S14 will be described, and the additional provision condition table will be described below in detail.

The user information stored in the portal server 41 includes the user identification information described above, personal information, and user provision history information. The personal information is, for example, information related to an individual user, such as the name of the user, the date of the user's birth, age, and gender (except for the biological information). The user provision history information represents the history of the provision information (having been provided) that has been already provided to the user. The user provision history information will be described below in detail.

The provision condition table is used to determine the health information needed for generating the provision information in step S14. The provision condition table is preset and stored in the portal server 41, and the content of the provision condition table may be updated at an appropriate time.

FIG. 9 illustrates an example of the provision condition table. As shown in FIG. 9, the provision condition table is a table in which provision conditions and provision contents are associated with each other. The provision condition represents a condition for providing the provision information. The provision content represents the content of the provision information to be provided when the provision condition associated therewith is satisfied. In FIG. 9, information indicating the content itself of the provision information such as "introduction of product A" is set as the provision content. However, when an identification number is assigned to each piece of the provision information prepared in the portal server 41, information indicating the identification number may be set as the provision content.

As shown in FIG. 9, in the present embodiment, the provision condition includes a user condition and a health condition. The user condition is a condition related to a user to whom the provision information is provided. A condition related to the personal information, such as "man in his 40s" and "men and women in their 30s", included in the user information is set as the user condition.

The health condition is a condition related to health (health information) of a user to whom the provision information is provided. As shown in FIG. 9, the health condition includes use information indicating the health information used for determining the health condition. The use information may indicate the secondary information, such as "the average fatigue level (in the latest one week)" shown in FIG. 9, obtained by processing the health information stored in the data server 2. Further, the use information may be information indicating (a kind of) the health information itself such as "the fatigue level (in the latest one week)". That is, the use request may be a request for the secondary information obtained by processing the health information, or a request for the health information itself.

For example, a condition related to the fatigue index or the sleep index, such as "(the average fatigue level in the latest one week) is higher than or equal to 4" or "(the average sleep hours in the latest one week) is less than or equal to five hours", is set as the health condition. The health condition may be a condition related to the health information itself (for example, the fatigue level), or a condition related to information (for example, the average fatigue level) obtained from the health information.

The health condition is not limited to one condition related to one kind of the health information. The health condition may include a plurality of conditions related to two or more kinds of the health information. For example, the health condition may include a condition related to the fatigue index, and a condition related to the sleep index. When the information (the biological information and/or the health information calculated from the biological information) obtained by the sub-terminal device 20 is transmitted via the main terminal device 10 to the data server, the health condition may include a condition related to the information.

In step S14 described above, the portal server 41 determines the health information to be requested from the data server 2, by using the provision condition table. That is, the portal server 41 specifies the health information used to determine the provision condition in the provision condition table, and requests the specified health information to the data server 2. Specifically, the portal server 41 specifies the provision condition that satisfies the user condition among the provision conditions included in the provision condition table, and specifies the use information included in the provision condition. For example, in a case where the provision condition table shown in FIG. 9 is used, when a user that logs in the portal site is a man in his 40s, the use information indicating "the average fatigue level in the latest one week" is specified. Therefore, the portal server 41 transmits, to the data server 2, the use request that requests "the average fatigue level in the latest one week". When a plurality of kinds of the provision conditions satisfy the user condition, the portal server 41 specifies a plurality of pieces of the use information associated with the plurality of the provision conditions, respectively, and transmits the use request which requests the health information indicated by the specified use information.

In other embodiments, sets each including the provision condition and the provision content in the provision condition table may be classified into a plurality of groups. For example, the sets may be classified into the plurality of groups according to, for example, a content of the provision information (introduced product/service), a genre of the product/service introduced by the provision information, a company that provides the product/service introduced by the provision information, and/or a price of the product/service introduced by the provision information. At this time, the portal server 41 may cause a user to previously select a group, and may execute a process of specifying the use information merely for the provision condition included in the sets of the selected group. For example, when the sets are classified into groups according to each genre of the product/service, a genre for goods (pillow, eye mask, and the like) for improving sleep and a genre of supplements for recovery from fatigue, may be set. At this time, when a user selects only the genre of supplements, the portal server 41 may execute a process of specifying the use information by using the provision conditions included in the genre as subjects to be processed, in the provision condition table. Thus, the provision information that belongs to the genre selected by the user is merely provided to the user, whereby the provision information in the genre in which the user is interested can be effectively provided. A process load, on the portal server 41, in the process of specifying the use information can be reduced.

The provision condition table indicates what product/service is to be introduced according to what health state the user is in. Therefore, the content of the provision condition table may be changed on the service providing side (the service providing server 42). That is, the portal server 41 may change the content of the provision condition table according to a request from the service providing server 42.

As described above, the use request transmitted from the portal server 41 to the data server 2 includes information indicating requested health information. FIG. 10 illustrates an example of the use request. As shown in FIG. 10, the use request includes requested information, the user identification information, and service identification information. The requested information is information indicating the health information that is requested to be obtained, and is determined on the basis of the specified use information. In the present embodiment, the requested information includes a kind of the health information that is requested to be obtained, and a time (period) when the health information has been obtained by the terminal system 1.

The user identification information indicates a user corresponding to the health information to be obtained. That is, the user identification information included in the use request indicates for what user the health information is to be obtained according to the use request.

The service identification information is identification information assigned to the product/service provided by the service providing server. The service identification information may be set for each service provider that provides the product/service, or may be set for each kind of the product/service. The service identification information included in the use request is determined on the basis of the provision information (the provision content associated with the use information indicating the health information in the provision condition table) corresponding to the health information requested by the use request. That is, it can be said that the service identification information corresponds to the provision information. In the present embodiment, the service identification information included in the use request is the service identification information assigned to the product/service introduced by the provision information corresponding to the health information requested in the use request, or the service identification information assigned to a service provider that provides the product/service.

The portal server 41 previously stores a table in which the provision content (service provider or the product/service specified by the provision content) included in the provision condition table is associated with the service identification information. The portal server 41 specifies the service identification information to be included in the use request with reference to the table.

When the use request is received, the data server 2 performs the authentication process for the use request (step S15). The authentication process is a process of determining whether or not the health information indicated by the requested information included in the use request can be used for a service indicated by the service identification information included in the use request (in other words, can be used for generating the provision information). In the present embodiment, the authentication process is performed by using the use management table (see FIG. 7) stored in the data server 2.

FIG. 11 illustrates an example of the use management table. As shown in FIG. 11, the use management table is a table in which the service identification information and use-allowed information are associated with each other. The use-allowed information indicates information, among the health information and the secondary information stored in the data server 2, which can be used (is allowed to be used) for the product/service indicated by the service identification information associated with the use-allowed information. The use-allowed information may indicate, for example, a kind of the health information such as "the sleep index/the fatigue index", "all the information", or "sleep index". Alternatively, the use-allowed information may indicate a period (in other words, a period in which the health information has been obtained) for the health information, such as "sleep index in the latest one month", which can be used among the health information chronologically stored. The use-allowed information may indicate, for example, a period in which the service server 3 can use the health information, such as "can be used from Dec. 1, 2013 to Dec. 1, 2014", which is not shown in FIG. 11. That is, the use-allowed information in the use management table may indicate a condition related to a kind of the health information, a condition related to a time when the health information is obtained, or a condition related to a period in which the health information is used (use-allowed period). In the example shown in FIG. 11, a group in which the service identification information corresponding to product A is associated with the use-allowed information indicating that the sleep index and the fatigue index can be used, is included. By this group, it is indicated that the sleep index and the fatigue index can be used for the provision information for introducing product A.

In the authentication process of step S15, the data server 2 determines whether or not the health information indicated by the requested information included in the received use request coincides with the health information indicated by the use-allowed information associated (in the use management table) with the service identification information included in the use request. When both the information coincide with each other, the data server 2 determines that the authentication has succeeded, and executes process steps of steps S16 and S17 described below (see FIG. 6). Meanwhile, when both the information do not coincide with each other, the data server 2 determines that authentication has failed, and does not execute the process steps of steps S16 and S17, which is not shown. In this case, the data server 2 transmits, to the portal server 41, a notification that authentication has failed. In this case, the portal server 41 does not generate the provision information, and the provision information is not provided to a user in S19 described below (the main page which does not include the provision information is provided).

When the authentication has succeeded, the data server 2 executes an analysis process corresponding to the use request (step S16). As described above, in some cases, the health information requested in the use request is information, such as "the average fatigue level in the latest one week", obtained by analyzing (processing) the health information stored in the data server 2. In such a case, the data server 2 calculates the health information requested in the use request in a process of analyzing the health information. For example, when the average fatigue level in the latest one week is requested, an average value is calculated by using the degrees of fatigue in the latest one week among the health information, of the user, which is indicated by the user identification information included in the use request. When the health information requested in the use request is the health information itself obtained by the terminal system 1, or is the secondary information having been already calculated in the analysis process of step S12 described above, the analysis process may not be executed in step S16.

Next, the data server 2 transmits, to the portal server 41, the health information requested in the use request (step S17). Thus, the portal server 41 can obtain the health information.

As described above, in the present embodiment, when the service server 3 generates the provision information, the service server 3 makes a request (use request), to the data server 2, for information used for generating the provision information. The data server 2 transmits, to the service server, stored information (the biological information and/or the health information) in response to the request from the service server 3. Thus, the information obtained from the user can be managed by the data server 2, and the information stored in the data server 2 can be used by the service server 3.

In the present embodiment, the use request includes the requested information indicating information used for generating the provision information, and identification information (service identification information) related to use of the information stored in the data server 2. The data server 2 determines, on the basis of the identification information included in the use request from the service server 3, whether or not the information indicated by the requested information included in the request is allowed to be used for generating the provision information. When it is determined that the use is allowed, the information indicated by the requested information is transmitted to the service server. Thus, the data server 2 can manage and control the use, by the service server 3, of the accumulated information, and can perform management and control such that the kinds of the information that can be used, can be made different according to the service identification information.

When the health information is received from the data server 2, the portal server 41 generates the provision information on the basis of the received health information (step S18). That is, the portal server 41 specifies the provision information that satisfies the provision condition (user condition and health condition) in the provision condition table by using the received health information. For example, when the provision condition table shown in FIG. 9 is used, the received value of the average fatigue level in the latest one week for a user who is a man in his 40s is higher than or equal to 4, the provision information for introducing product A is specified. When no provision content satisfies the provision condition, the provision information is not generated, and the provision information is not transmitted. The number of pieces of the provision information specified in the process step of step S18 may be plural.

In the process step of step S18, the portal server 41 stores a history of the provision information having been specified. That is, the portal server 41 updates the content of the user provision history information (see FIG. 8) included in the user information for the user who has performed log-in.

Figures 12, 13:
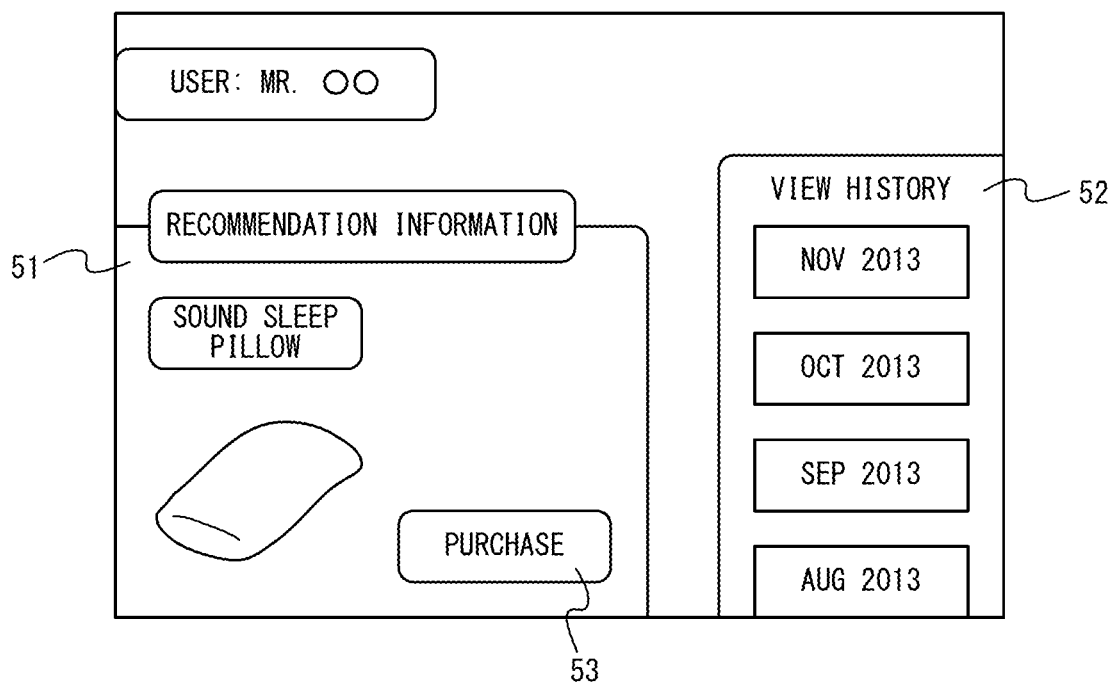
FIG. 12 illustrates an example of user provision history information.
FIG. 13 illustrates an example a main page displayed by the terminal system.

FIG. 12 illustrates an example of the user provision history information. In the present embodiment, the user provision history information includes information in which provided-content information, provision date information, purchase information, and additional provision time information are grouped. The provided-content information included in the user provision history information indicates the content of the provision information provided to a user, similarly to the provision content in the provision condition table described above. The provision date information indicates a time (in the description herein, year, month, and day)

when the provision information associated therewith is provided. In the present embodiment, the provision date information indicating year, month, and day is stored. However, information indicating a time in addition to year, month, and day may be stored.

The purchase information indicates whether or not the product/service introduced by the provision information associated therewith has been purchased. The additional provision time information indicates whether or not the provision information is additionally provided after the provision information associated therewith is provided, and indicates a time when the additional provision is performed in the case of the additional provision being performed. The additional provision time information will be described below.

In the process step of step S18 described above, the portal server 41 adds the information in the above-described group to the user provision history information for the specified provision information. Specifically, the portal server 41 adds, to the user provision history information, the provided-content information which indicates the provision information specified in the process step of step S18, the provision date information indicating year, month, and day when the provision information is provided, the purchase information indicating that purchasing is not performed, and additional provision time information indicating that additional provision is not performed. In the process step of step S18, the purchase information is stored so as to indicate that "purchasing is not performed" and the additional provision time information is stored so as to indicate that "additional providing is not performed". However, the purchase information and the additional provision time information are updated when a product or the like is purchased, as described below.

Next, the portal server 41 generates a web page including the specified provision information, and transmits the web page to the terminal system 1 (step S19). In the present embodiment, the web page is a main page (also referred to as a top page or a home page) which is firstly displayed when the terminal system 1 accesses (logs in) the portal site. However, in another embodiment, the page including the provision information may not be the main page. When the main page is received by the terminal system 1, the main page is displayed by the display 16 in the main terminal device 10. Thus, the provision information is provided to the user.

FIG. 13 illustrates an example of the main page displayed by the terminal system. As shown in FIG. 13, the main page includes a provision information section 51 and a history viewing section 52. In the provision information section 51, the provision information (information for introducing a pillow as a product in FIG. 13) is displayed. In the present embodiment, the content displayed in the provision information section 51 is defined by the provision information. In FIG. 13, the provision information section 51 contains one kind of the provision information. However, the provision information section 51 may contain a plurality of pieces of the provision information.

The provision information section 51 includes a purchase button 53 by which the product related to the provision information is purchased. That is, when a user performs an input for designating the purchase button 53, a product purchase page for purchasing of the product is newly displayed on the display 16, and the user is allowed to purchase the product. In the present embodiment, the product purchase page is a page (page in the portal site) provided by the portal server 41. However, in another embodiment, the product purchase page may be a page (page outside the portal site) provided by the service providing server. That is, the purchase button 53 may indicate a link to the product purchase page provided by the service providing server.

The history viewing section 52 is provided so as to allow the history of the health information stored in the data server 2 to be referred to. In the present embodiment, the history viewing section 52 includes a button indicating year and month, and, when a user performs an input for designating the button, a page on which the health information for the designated year and month is displayed, is displayed on the display 16.

As described above, in the present embodiment, the service server 3 generates the provision information including information related to a product or a service for improving an index indicated by the health information of the user. Thus, useful information related to the product/service can be provided to the user. The service server 3 generates the provision information including information of the web page for allowing a user to purchase the product/service, or link information for link to the web page. Thus, when the provision information for introducing the product/service is provided, the user can purchase the product/service provided therein, in a simple operation, thereby improving usability for the user.

<3> Process for Purchasing of Product

Next, a process performed when a user purchases a product indicated by the provision information displayed on the main page, will be described. When a user performs an input of an operation for purchasing a product on the product purchase page, the terminal system 1 transmits, to the portal server 41, a notification of instruction for purchase (step S20). The notification of instruction for purchase includes the user identification information and information for identifying a product to be purchased. When the notification of instruction for purchase is received, the portal server 41 transmits the notification of purchase to the service providing server 42 that provides the product to be purchased (step S21). The notification of purchase includes the user identification information and the information for identifying the product to be purchased, both of which are included in the notification of instruction for purchase.

When the notification of purchase is received from the portal server 41, the service providing server 42 executes a providing process related to providing of the product/service (step S22). For example, when data is provided as the product/service via a network, the providing process is, for example, a process of transmitting data related to the product or service. The "data related to the product or service" is, for example, music data, data of recipes for meals, application data, or the like. The "data related to the product or service" may be, for example, data (application) for illumination, by the illumination section 17 of the main terminal device 10, for inducing sleep onset or wake-up of the user. When the terminal system 1 has a loudspeaker, the "data related to the product or service" may be data (application) for outputting, from the loudspeaker, music for inducing sleep onset or wake-up of the user.

When a product (for example, sleep improving goods such as a pillow or an eye mask) which is an actual object is provided, the providing process is, for example, a process of transmitting, to the terminal system 1 of the user, a notification that purchase of a product has been received, or a process of transmitting, to the terminal system 1 of the user, a notification that the product is delivered. When a service (for example, massage or the like) is actually provided, the providing process is a process of transmitting, to the terminal system 1 of the user, a notification that purchase of the service has been received, or a process of transmitting, to the terminal system 1 of the user, a notification of a date and time when the service is provided. For example, the service server 3 may introduce a massage service by the provision information (for example, introduce a massage shop located near the user), and perform booking (purchase of a massage service) of a massage on the portal site.

As described above, the service server 3 may transmit, to the terminal system 1, the data related to the product or service, according to an instruction, from a user, for purchasing the product or service being received from the terminal system 1.

When the notification of instruction for purchase is received, the portal server 41 updates the user provision history information (FIG. 12) related to the user who has issued an instruction for purchase such that purchase of the product is reflected (step S23). Specifically, the portal server 41 updates the purchase information associated with the provision information for introducing the product for which the instruction for purchase has been issued such that the content of the purchase information indicates that "purchasing has been performed". The portal server 41 updates the additional provision time information associated with the provision information such that the content of the additional provision time information indicates a time when the additional provision information is to be provided.

In the present embodiment, when the product/service introduced by the provision information has been purchased, new provision information is provided after the purchase. Hereinafter, the provision information that is additionally provided anew is referred to as "additional provision information". The content of the additional provision information and the content of the provision information having been firstly provided may be different from each other, or may be the same. The content of the additional provision information is determined on the basis of the health information, of the user, which has been uploaded after the product/service has been purchased. The detail thereof will be described below.

In step S23 described above, a time when the additional provision information is provided is determined, and the additional provision time information in the user provision history information is updated such that the content of the additional provision time information indicate the determined time. The portal server 41 determines a time when the additional provision information is provided, according to the provision information having been provided. In the present embodiment, the time at which the additional provision information is provided is determined by using the additional provision condition table (see FIG. 8) stored in the portal server 41.

FIG. 14 illustrates an example of the additional provision condition table. The additional provision condition table is a table for determining the content of the additional provision information and a timing for the additional provision information. As shown in FIG. 14, the additional provision condition table is a table in which an immediately preceding provided-content, an additional provision time, an additional provision condition, and an additional provision content are associated with each other. Similarly to the provision condition table, the additional provision condition table is preset and stored in the portal server 41, and the content of the additional provision condition table may be updated at an appropriate time. Similarly to the provision condition table, the content of the additional provision condition table may be changed on the service providing side (the service providing server 42).

The immediately preceding provided-content represents content of the provision information which has been provided immediately preceding time. In other words, the immediately preceding provided-content represents the content of the provision information that causes providing of the additional provision information. The additional provision time represents a time when additional providing is performed, that is, a time when the additional provision information associated with the additional provision time is provided. In the present embodiment, the additional provision time represents, for example, a time that has elapsed from purchase of the product/service, such as "two weeks after purchase" or "one month after purchase". However, in another embodiment, the additional provision time may represent: a time that has elapsed from the time when the provision information has been provided immediately preceding time; or a time that has elapsed from the time when the product has been actually used or a time that has elapsed from the time when the service has been actually performed, in the case of the time when the product has been actually used or the time when the service has been actually performed being obtained by the portal server 41. The additional provision condition and the additional provision content will be described below in detail In step S23, the portal server 41 specifies the provision information for introducing a purchased product, and specifies the additional provision time associated (in the additional provision condition table) with the immediately preceding provided-content indicating the specified provision information. The portal server 41 calculates a time (in the description herein, year, month, and day) when additional providing is performed, on the basis of the specified additional provision time. The additional provision time information in the user provision history information is updated so as to represent the information of the calculated year, month, and day. For example, when the current time (time when purchase is performed) is Dec. 6, 2013, and the specified additional provision time is "two weeks after the purchase", information indicating Dec. 20, 2013 is stored as the additional provision time information.

<4> Process of Providing Additional Provision Information after Product/Service has been Purchased.

As described above, in the present embodiment, when the product/service has been purchased, a time when the additional provision information is provided is determined on the basis of the provision information for introducing the purchased product/service. The portal server 41 periodically determines whether or not the additional provision time has come, by periodically referring to the user provision history information for each user. When it is determined that the additional provision time has come, the portal server 41 executes a process (S24 to S29 shown in FIG. 6) of providing the user with the additional provision information for which the additional provision time has come. That is, when a predetermined time (period specified by the additional provision time in the additional provision condition table) has elapsed from purchasing of the product, the above-described process is executed (see FIG. 6).

Specifically, when there is the additional provision information for which provision time has come, the portal server 41 transmits, to the data server 2, the use request for requesting use of the health information needed for determining the additional provision information (step S24). The health information needed for determining the additional provision information is the health information used for determining the additional provision condition (see FIG. 14) for the additional provision information. In the process step of step S24, the health information needed for determining the additional provision information is determined by using the additional provision condition table stored in the portal server 41.

As shown in FIG. 14, in the additional provision condition table, the immediately preceding provided-content, (the additional provision time), the additional provision condition, and the additional provision content are associated with each other. The additional provision condition indicates a condition (additional provision condition) for providing the additional provision information, for the provision information indicated by the immediately preceding provided-content associated therewith.

The additional provision condition includes use information indicating the health information used for determining the additional provision condition. The use information is similar to the use information included in the provision condition. However, the use information included in the additional provision condition may be set, for example, so as to designate both the health information before purchase of the product/service and the health information after purchase of the product/service, such as "the average fatigue level in the latest one week and the average fatigue level in one week immediately before the purchase".

The additional provision condition represents a condition related to the health information of a user. Specifically, the additional provision condition may represent a condition related to change (change of a user's state indicated by the health information) of the health information such as "the fatigue level has improved" or "the fatigue level has not improved". The additional provision condition may be similar to the health condition (see FIG. 9) described above, and, for example, the condition related to a user's state indicated by the health information, such as "the average sleep hours in the latest one week are less than or equal to five hours", may be set as the additional provision condition.

The additional provision content represents the content of the additional provision information provided when the additional provision condition associated therewith is satisfied. Similarly to the provision content in the provision condition table described above, as additional provision content included in the additional provision condition table, information indicating the content itself of the provision information may be set, or information indicating the identification number assigned to the provision information may be set.

In step S24 described above, the portal server 41 firstly specifies the provision information corresponding to the additional provision information for which the provision time has come, with reference to the user provision history information. That is, the portal server 41 specifies the provision information indicated by the provided-content information associated with the additional provision time information for which the provision time has come, in the user provision history information.

Next, the portal server 41 specifies the additional provision condition for the additional provision information corresponding to the provision information having been specified as described above. That is, the portal server 41 specifies the additional provision condition associated with the immediately preceding provided-content indicating the provision information having been specified, with reference to the additional provision condition table. The portal server 41 specifies the use information included in the additional provision condition having been specified, and transmits, to the data server 2, the use request for obtaining the health information indicated by the use information having been specified. That is, the use request including the requested information indicating the health information is transmitted to the data server 2. For example, a case where, when the additional provision condition table shown in FIG. 14 is used, the provision information indicating "introduction of product A" is specified, will be described. In this case, the use information indicating "the average fatigue level in the latest one week, the average fatigue level in one week immediately before purchase", is specified and the use request for obtaining the health information indicated by the use information is transmitted to the data server 2.

The use request which is transmitted in step S24 includes the requested information, the user identification information, and the service identification information, similarly to the use request which is transmitted in step S14. The contents of the three kinds of information are determined in a method similar to the method in the process step of step S14. For example, as in a case where the use information indicating "the average fatigue level in the latest one week, the average fatigue level in one week immediately before purchase" is specified, the requested information sometimes indicates the health information in a predetermined period based on the time of purchase. In this case, the portal server 41 may use, as the purchase date, a date indicated by the provision date information of the user provision history information, or may use, when a date on which the product has been purchased is previously stored, the stored date as the purchase date, in order to calculate the predetermined period.

The data server 2 executes the process similar to the process steps of step S15 to S17 according to the use request from the portal server 41. That is, the data server 2 performs the authentication process for the use request (S25). When the authentication has succeeded, an analysis process according to the use request is executed as appropriate (step S26). The health information requested in the use request is transmitted to the portal server 41 (step S27).

When the health information is received from the data server 2, the portal server 41 generates the additional provision information on the basis of the received health information (step S28). That is, the portal server 41 determines, by using the received health information, whether or not the additional provision condition specified in step S24 described above is satisfied. The portal server 41 generates the additional provision information having additional provision content that satisfies the additional provision condition. When no additional provision content satisfies the additional provision condition, the additional provision information is not generated. The number of pieces of the additional provision information specified in the process step of step S28 may be plural.

Figure 15:
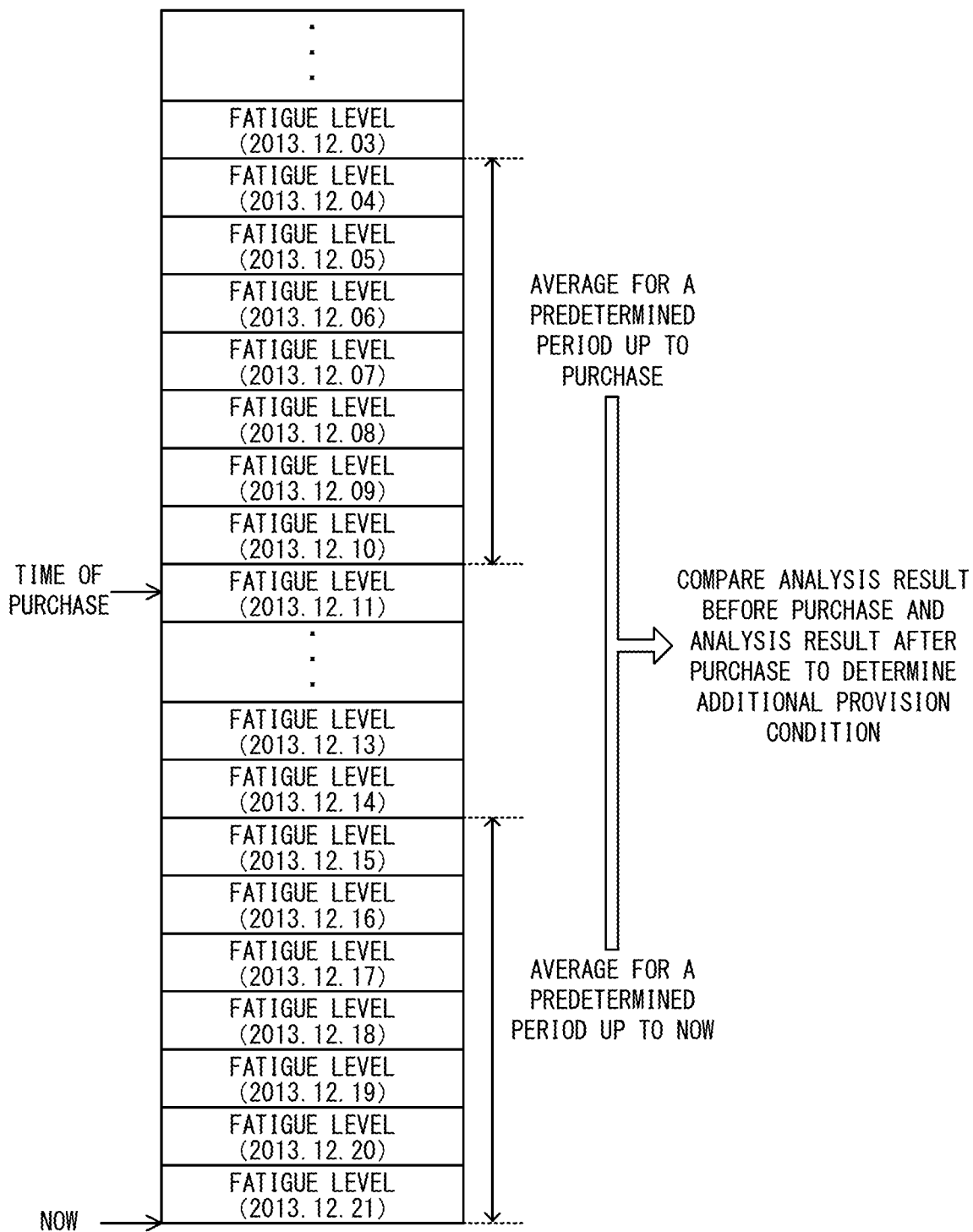
FIG. 15 illustrates an example of a method for determining an additional provision condition.

FIG. 15 illustrates an example of a method for determining the additional provision condition. As shown in FIG. 15, in the present embodiment, the health information (the fatigue level in the drawings) obtained every day is stored in the data server 2. As described above, in the present embodiment, whether or not the additional provision condition is satisfied is determined, in some cases, by comparison between the health information before purchase of the product/service and the health information after purchase of the product/service. In these cases, the health information in a predetermined period from the current time to a previous time is firstly analyzed as the health information of the user after the purchase, and the health information in a predetermined period from the time of the purchase to a previous time is analyzed as the health information of the user before the purchase. For example, as shown in FIG. 15, the data server 2 calculates an average fatigue level in the latest one week and an average fatigue level in one week immediately before the purchase, as analysis results, according to the use request from the portal server 41. The portal server 41 performs comparison between the result of the analysis (the average fatigue level in one week immediately before the purchase) of the health information before the purchase, and the result of the analysis (the average fatigue level in the latest one week) of the health information after the purchase, whereby whether or not the health state of the user has improved is determined. For example, when the average fatigue level is reduced by a predetermined value or more, the portal server 41 determines that the health state (the fatigue level) of the user has improved, whereas when the average fatigue level is not reduced by the predetermined value or more, the portal server 41 determines that the health state (the fatigue level) of the user has not improved. The portal server 41 generates the additional provision information such that the content thereof is different according to the determination results. For example, in the example of the additional provision condition table shown in FIG. 14, when it is determined that the fatigue level has improved, on the basis of: the average fatigue level in one week immediately before the purchase; and the average fatigue level in the latest one week, the additional provision information for introducing product D is generated. Meanwhile, when it is determined that the fatigue level has not improved, the additional provision information for introducing product E is generated.

As described above, in the present embodiment, the analysis (time-series analysis in consideration of time at which the health information is obtained) is performed on the basis of a plurality of pieces of the health information that are time-series data accumulated for a user for which the health state is analyzed. Thus, change of the health state of the user can be known. Therefore, the provision information based on such an analysis is provided, thereby providing useful information.

In the present embodiment, the additional provision information according to an effect of improvement (of the health state) by the product or service is generated on the basis of the health information obtained by the terminal system after the product or service indicated in the provision information has been purchased. Thus, the effect of the product/service can be determined, and appropriate provision information can be provided according to the determination result.

As described above, in the present embodiment, the data server 2 performs analysis by comparison between: the health state based on the information obtained by the terminal system 1 before a predetermined reference time (time of purchase); and the health state based on the information obtained by the terminal system 1 after the reference time. Thus, change of the health state by the provision information (or the product/service provided by the provision information) can be accurately analyzed, and the provision information based on the analysis is generated, whereby the provision content can be made useful.

The predetermined reference time represents, for example, a time when the product/service introduced by the provision information is purchased. However, the predetermined reference time may be any time based on the provision information having been provided to a user. For example, the reference time may be a time when the provision information is provided. For example, when a time when a user starts using the product, and/or a time when a user receives the provided service can be obtained on the server side, such a time may be used as the reference time.

When the additional provision information has been generated, the portal server 41 transmits the additional provision information to the terminal system 1 (step S29). There is no particular limitation on the method for transmitting the additional provision information. In the present embodiment, a message indicating that there is the additional provision information is transmitted by push notification to the terminal system 1. That is, when the additional provision information has been generated, the portal server 41 transmits the message in a method in which notification of the message is made even when a user does not perform an operation (does not access the portal site). That is, the terminal system 1 that receives the message, performs display of the message on the display 16 independently of the operation by the user. The user accesses the portal site by using the terminal system 1 according to the message. When the user logs in the portal site, the portal server 41 generates the main page that includes the additional provision information, and transmits the main page to the terminal system 1. Thus, the additional provision information is provided to the user.

As described above, the service server 3 transmits, to the terminal (terminal device (the main terminal device 10) in the terminal system 1) of the user, the notification (the above-described message) of the additional provision information, at a time independent of a time when the user performs the operation on the terminal device, according to the additional provision information having been generated. In other embodiments, the additional provision information itself may be transmitted to the terminal system 1 by push notification. That is, the additional provision information may be transmitted from the portal server 41 to the terminal system 1, independently of the operation performed by the user. In other words, the additional provision information may be displayed by the terminal system 1 without access to the portal site. Thus, the notification that the additional provision information has been generated can be made to the user, at an appropriate time, by notification of the additional provision information, or by the additional provision information being transmitted to the terminal system 1 by push notification.

In other embodiments, the above-described message may not be transmitted. In this case, at a time when the portal server 41 has generated the additional provision information, the user is not notified thereof, and, when the user accesses the portal site the subsequent time, the additional provision information is provided.

In other embodiments, similarly to the additional provision information, the push notification may be used for the provision information (which is not the additional provision information). That is, the service server 3 may transmit notification of the provision information (which is not the additional provision information) or the provision information itself, at a time independent of a time when the user performs the operation on the terminal device. More specifically, the portal server 41 may execute the process steps of steps S14 and S18, according to a predetermined condition having been satisfied (according to, for example, a predetermined time having come).

As described above, in the present embodiment, after the provision information is provided, the additional provision information is provided. After the provision information is provided, the process of analyzing the information (the health information) from the terminal system 1, and the process of generating the additional provision information based on the result of the analysis may be repeatedly executed. For example, the portal server 41 may set a time (for example, after purchase of the product, every two weeks) that repeatedly comes, as the additional provision time in the additional provision condition table (see FIG. 14). Thus, the analysis process and the generation process are repeatedly executed each time the time comes. For example, the portal server 41 may set a group (group including the immediately preceding provided-content, the additional provision time, the additional provision condition, and additional provision content) in which the provision information indicated by additional provision content is included as the immediately preceding provided-content in the additional provision condition table. For example, a group in which the provision information for introducing product D is set as the immediately preceding provided-content in the additional provision condition table shown in FIG. 14, may be set. Thus, when a user purchases product D according to the additional provision information being provided, the additional provision information is further provided after the purchase. As described above, the analysis process and the generation process are repeated, whereby useful information can be continuously provided to a user.

(Process by Data Server 2)

Figure 16:
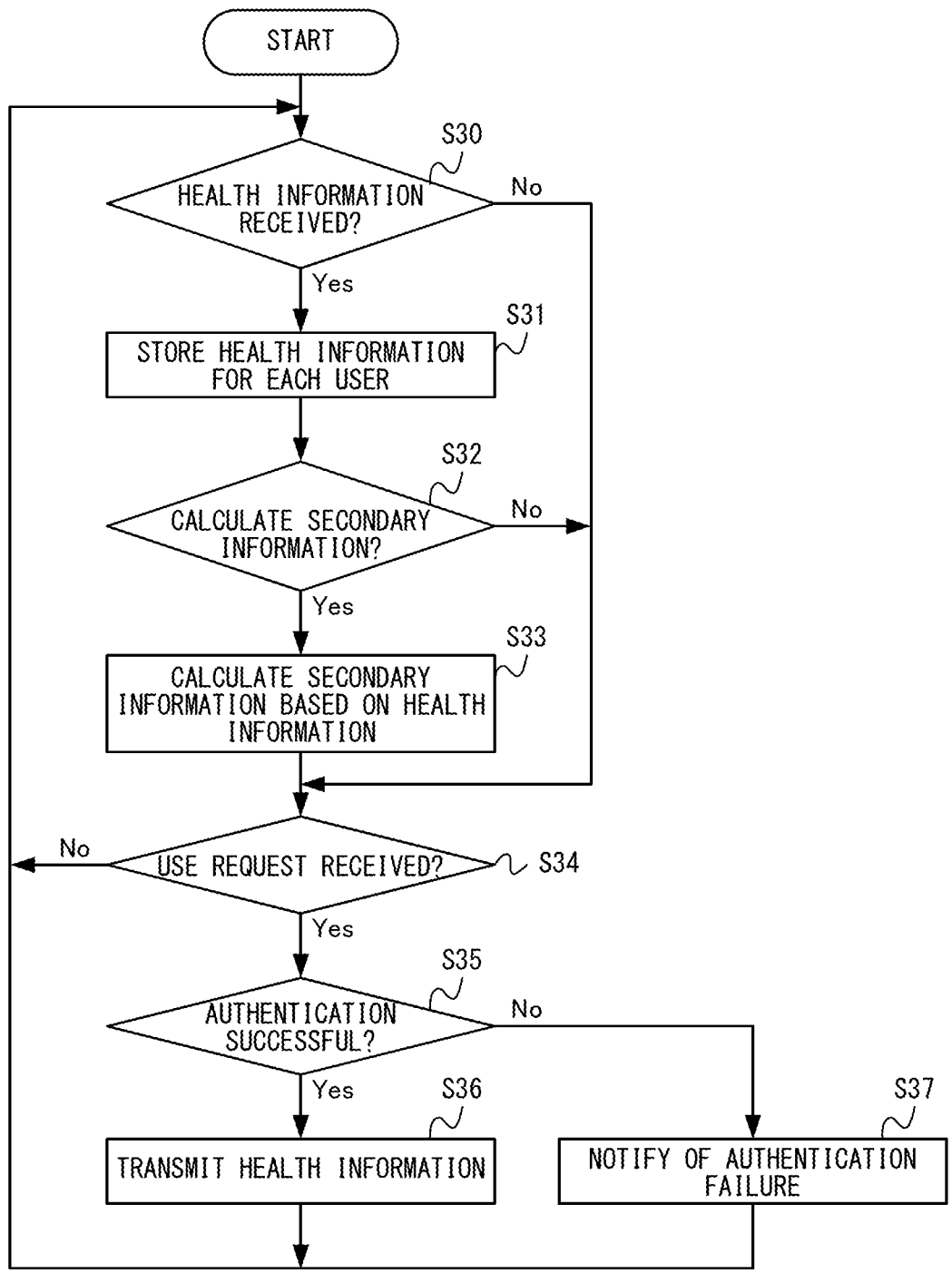
FIG. 16 is a flow chart showing an example of a flow of a process executed by the data server.

FIG. 16 is a flow chart showing an example of a flow of a process executed by the data server 2. In the present embodiment, the data server 2 repeatedly executes a series of process from step S30 to step S37 shown in FIG. 16. The series of process is performed by the CPU that is a processing section of the data server 2 executing a predetermined information processing program stored in a program storage section of the data server 2. When the data server 2 includes a plurality of information processing devices, the CPUs of the respective information processing devices may share the execution of the series of process.

Firstly, in step S30, the processing section of the data server 2 determines whether or not the health information is received from the terminal system 1 (see S11 shown in FIG. 6). When the result of the determination in step S30 is affirmative, the process step of step S31 is executed. When the result of the determination in step S30 is negative, the process step of step S34 describe below is executed.

In step S31, the processing section stores the health information received from the terminal system 1, in a storage section of the data server 2, for each user (see FIG. 7). In step S32, the processing section determines whether or not the secondary information is to be calculated, on the basis of the received health information. This determination is performed according to, for example, whether or not a time when the secondary information is to be calculated has come, or whether or not the health information for calculating the secondary information has been accumulated. When the result of the determination in step S32 is affirmative, the process step of step S33 is performed. When the result of the determination in step S32 is negative, the process step of step S34 described below is executed.

In step S33, the processing section calculates the secondary information on the basis of the received health information, and stores the calculated secondary information in the storage section of the data server 2 (see S12 shown in FIG. 6). As described above, the data server 2 stores the health information (step S31) each time the health information is received from any one of the plurality of users, and calculates and stores the secondary information as appropriate.

In step S34, the processing section determines whether or not the use request is received from the portal server 41 (see S14, S24 shown in FIG. 6). When the result of the determination in step S34 is affirmative, the process step of step S35 is executed. When the result of the determination in step S34 is negative, the process step of step S30 is executed again.

In step S35, the processing section executes the authentication process for the use request having been received in step S34 (see S15, S25 shown in FIG. 6), and determines whether or not the authentication has succeeded. When the result of the determination in step S35 is affirmative, the process step of step S36 is executed. When the result of the determination in step S35 is negative, the process step of step S37 is executed.

In step S36, the processing section transmits, to the portal server 41, the health information requested in the use request. That is, the processing section analyzes, as appropriate, the health information stored in the storage section, and transmits, to the portal server 41, the health information, and/or the health information that is the result of the analysis (see S16, S17, S26, S27 shown in FIG. 6).

Meanwhile, in step S37, the processing section transmits, to the portal server 41, notification that the authentication has failed. When the process step of step S36 or S37 is completed, the process step of step S30 is executed again. In the process steps of S30 to S37 described above, the operation performed by the data server 2 as shown in FIG. 6 is implemented.

(Process by Portal Server 41)

Figure 17:
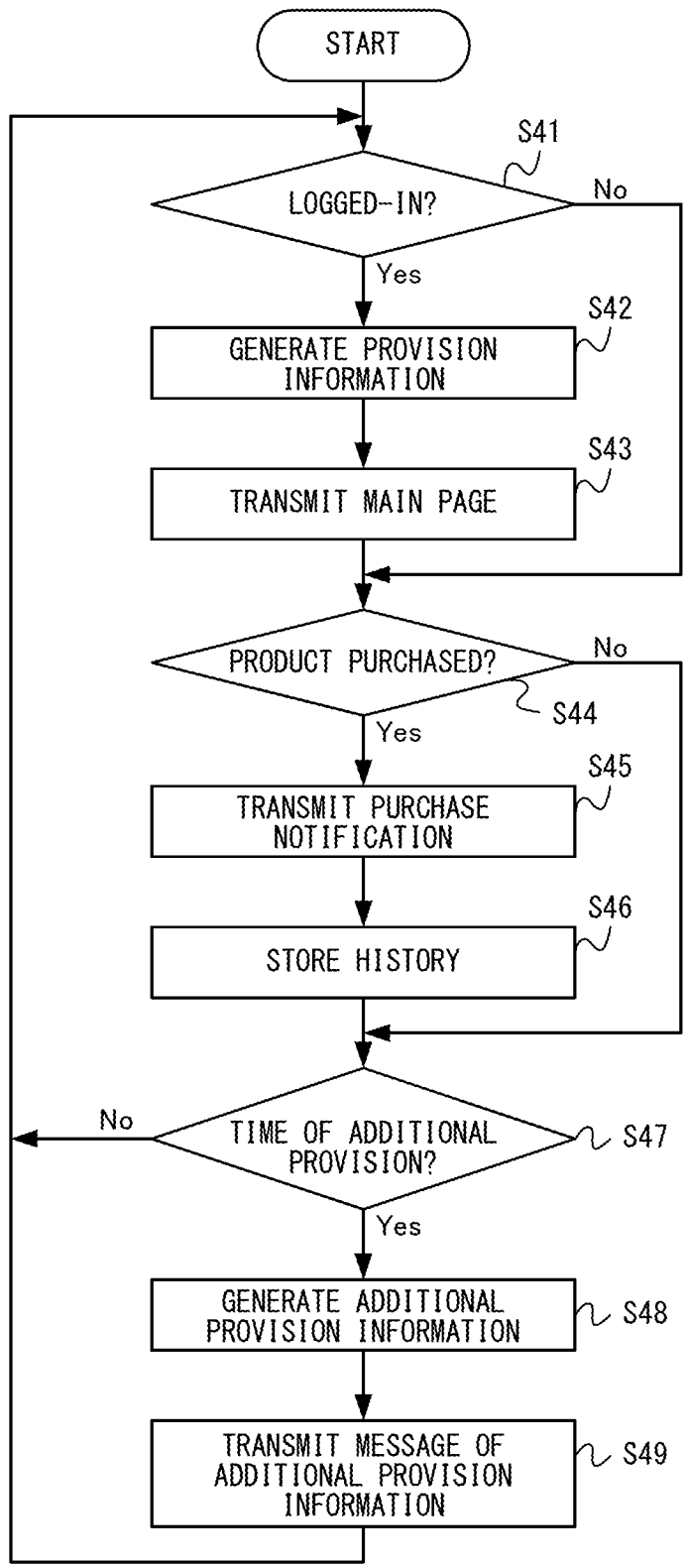
FIG. 17 is a flow chart showing an example of a flow of a process executed by a portal server.

FIG. 17 is a flow chart showing an example of a flow of a process executed by the portal server 41. The portal server 41 repeatedly executes a series of process from step S41 to step S49 shown in FIG. 17. The series of process is performed by the CPU that is a processing section of the portal server 41 executing a predetermined information processing program stored in a program storage section of the portal server 41. When the portal server 41 includes a plurality of information processing devices, the CPUs of the respective information processing devices may share the execution of the series of process.

Firstly, in step S41, the processing section of the portal server 41 determines whether or not access from the terminal system 1 is performed and log-in is performed by a user of the terminal system 1 (S13 shown in FIG. 6). When the result of the determination in step S41 is affirmative, the process step of step S42 is executed. When the result of the determination in step S41 is negative, the process step of step S44 described below is executed.

In step S42, the processing section generates the provision information (see S14, S18 shown in FIG. 6). In step S43, the processing section generates the main page that includes the provision information and transmits the main page to the terminal system 1 (see S19 shown in FIG. 6). At this time, when the additional provision information having been already generated has not been provided yet, the processing section generates the main page including the additional provision information, in addition to the provision information. The provision information and the additional provision information are provided so as to be distinguished from each other (for example, such that display positions on the page and/or display manners are different). In the terminal system 1, in a period from display of the main page to the log-out from the portal site by the user, the process of displaying, on the terminal system 1, the web page (for example, page indicated by the history of the health information) is executed as appropriate according to an input from the user, which is not shown.

In step S44, the processing section determines whether or not a product introduced by the provision information in the portal site is purchased. This determination is performed according to whether or not the notification of instruction for purchase has been received from the terminal system 1. When the result of the determination in step S44 is affirmative, the process step of step S45 is executed. When the result of the determination in step S44 is negative, the process step of step S47 described below is executed.

In step S45, the processing section transmits the notification of purchase to the service providing server 42 (see S21 shown in FIG. 6). In step S46, the processing section updates the user provision history information so as to reflect the purchasing of the product (see S23 shown in FIG. 6). As described above, at this time, a time when the additional provision information is to be provided is determined.

In step S47, the processing section determines whether or not the time when the additional provision information is to be provided has come (see S24 shown in FIG. 6). When the result of the determination in step S47 is affirmative, the process step of step S48 is executed. When the result of the determination in step S47 is negative, the process step of step S41 is executed again.

In step S48, the processing section generates the additional provision information for which the provision time has come (see S28 shown in FIG. 6). In step S49, the processing section transmits, to the terminal system 1, the message that notifies the user of presence of the additional provision information (see S29 shown in FIG. 6). When the user logs in the portal site according to the message having been displayed on the terminal system 1, the main page including the additional provision information is transmitted from the portal server 41 to the terminal system 1 by the process step of step S43, and the main page is displayed on the terminal system 1. When the process step of step S49 has been completed, the process step of step S41 is executed again. In the process from S41 to S49 described above, the operation performed by the portal server 41 as shown in FIG. 6 is implemented.

[5. Function and Effect of the Present Embodiment]

As described above, in the present embodiment, the terminal system 1 transmits the health information to the server system (system on the server side, the data server 2 and the service server 3 in the above embodiment). The server system receives transmission information (health information) from the terminal system 1, and stores the received transmission information such that the transmission information is associated with a user.

The server system generates the provision information to be provided to the user for improving an index obtained from the transmission information or an index included in the transmission information (index indicated by the health information related to the user, specifically, the sleep index, the fatigue index), on the basis of the result of the analysis of the transmission information, and transmits the provision information to the terminal system 1 (S18, S19). The server system generates additional provision information that is different from the provision information having been provided, on the basis of the result of the analysis of the transmission information that is obtained by the terminal system 1 after the provision information has been provided to the user, and transmits the additional provision information to the terminal system 1 (S28, S29).

Thus, the first provision information is provided, and a user state is analyzed on the basis of the health information having been thereafter obtained, and new provision information is generated on the basis of the result of the analysis. Thus, the second provision information can be provided in consideration of an effect (including a result of determination as to whether or not the effect is found) exerted by the first provision information, whereby useful information can be provided to the user. For example, when the product/service introduced by the first provision information has been purchased, the effect of the product/service is determined on the basis of the health information obtained after the purchase, and the second provision information can be provided according to the effect, whereby useful information can be provided to the user.

In the present embodiment, the server system (data server 2) stores (accumulates in the present embodiment), as the storage information, the transmission information received from the terminal system and information (health information) obtained from the transmission information such that the transmission information and the information obtained from the transmission information are associated with the user. The data server 2 receives, from the service server 3 that provides the provision information to the user of the terminal system by using the storage information, the use request that includes: the requested information indicating the information used for generating the provision information; and the service identification information for identifying a service related to the provision information, as a request (use request) for use of the storage information for generating the provision information (S14, S24, FIG. 10). The data server 2 determines whether or not the information indicated by the use information included in the use request is allowed to be used for generating the provision information, on the basis of the service identification information included in the use request which is received from the service server 3 (S15, S25). When the use is determined to be allowed, the information that is based on the storage information and indicated by the requested information is transmitted to the service server 3.

Thus, the server system can manage and control use of the storage information by the service server. For example, the server system can also manage and control use of the storage information for each kind of use-allowed information according to the service identification information. Thus, by use of the storage information being managed and controlled, the server system can provide a service for allowing the service server to use the storage information by charging the fee according to the use. For example, in the above embodiment, a managing company that manages the data server 2 and the portal server 41 can provide a service that allows a service provider that manages the service providing server 42 to use the storage information.

The server system stores association information (use management table) in which the service identification information, and use-allowance information (use-allowed information) that indicates the information which is based on the storage information, and which is allowed to be used for the service indicated by the service identification information, are associated with each other. The above determination is performed on the basis of the association information. Thus, the determination is facilitated.

In the present embodiment, the server system determines whether or not information that is indicated by the requested information included in the use request which is received from the service server can be used, on the basis of a condition related to the kind of the storage information, a time when the storage information is obtained, and/or a period in which the storage information is used (S15). Thus, use of the storage information can be managed according to the kind of the storage information and/or the time when the storage information is obtained. Further, a period of use can be set for the storage information. When the above-described managing company provides a service of allowing a service provider to use the storage information as described above, the managing company can set, for example, a use fee of the storage information according to the storage information that can be used.

In the present embodiment, the server system (portal server 41) generates the provision information for introducing the product/service on the basis of the transmission information (S19), and receives, from a user to which the provision information has been provided, a purchase instruction for purchasing of the product/service indicated by the provision information (S20). Thus, the server system can perform not only a service of providing the provision information related to the product/service, but also a service of providing the product/service introduced by the provision information. A user is allowed to purchase the product/service indicated by the server system by making an instruction to the server system, thereby improving convenience in the purchase.

In the present embodiment, the portal server 41 in the service server 3 transmits, to the service providing server 42, a predetermined notification of purchase according to the purchase instruction having been received. The service providing server 42 executes a service providing process (S22) according to the notification of purchase having been received. Thus, the service providing process is performed by the service providing server 42 on the service provider side for providing the product/service, and purchasing of the product/service can be managed by the portal server 41 on the managing company side.

In the present embodiment, the information processing system calculates an index indicating fatigue of a user. That is, the information processing system automatically obtains the biological information from a non-worn type sensor (Doppler sensor 11), and stores the obtained biological information (S5). The information processing system calculates a fatigue index of the user on the basis of the stored biological information (S7). Thus, a fatigue degree of the user can be measured without making the user conscious of the measurement.

The terminal system 1 repeatedly obtains the biological information from the sensor. The biological information having been repeatedly obtained is stored and accumulated, and the fatigue index of a user is calculated on the basis of the biological information which is stored and accumulated. Thus, the fatigue degree of the user can be continuously measured.

[6. Variations]

(Variation in which Provision Condition is Automatically Updated)

In the variation of the above embodiment, the provision condition may be automatically updated on the basis of the health information obtained from each user. In the health information obtained after the product/service introduced by the provision information has been purchased, the health state after the use of the product/service by the user is reflected. Therefore, an effect obtained by the product/service being used by the user can be inferred from the health information. In the present variation, the portal server 41 updates the provision condition on the basis of such an effect. Thus, the provision information that is more effective for the user can be provided. Hereinafter, the present variation will be described in detail.

In the present variation, the portal server 41 stores a condition update table for updating of the provision condition. FIG. 18 illustrates an example of the condition update table. As shown in FIG. 18, the condition update table is a table in which the provision content, an update condition, and an update content are associated with each other for each provision information. Similarly to the provision content in the provision condition table, the provision content represents a content of the provision information.

The update condition represents a condition for updating the provision condition (provision condition associated with the provision information in the provision condition table) related to the provision information. In the present variation, the update condition includes a number-of-pieces-of-data condition, and a change condition. The number-of-pieces-of-data condition represents a condition related to the number of pieces of data for effect information indicating the effect of the product/service introduced by the provision information. The effect information represents a result of an analysis of the health information obtained after the product/service has been purchased, and represents, for example, the health information used for determining the additional provision condition. When the additional provision condition is determined, according to the product/service in a certain piece of provision information having been purchased, after the purchase thereof, the portal server 41 stores, as the effect information, the health information used for the determination. Therefore, when a plurality of users purchase the product/service, the number of pieces of effect information corresponding to the number of the users that has purchased the product/service are obtained (stored) by the portal server 41.

The number-of-pieces-of-data condition represents a condition related to the number (the number of pieces of data) of pieces of the effect information stored as described above. As the number-of-pieces-of-data condition, for example, a condition that "the effect information for 100 persons has been obtained" is set.

The change condition represents a condition related to the effect information for the number-of-pieces-of-data condition. As the change condition, for example, a condition that "the number of pieces of the effect information indicating that the effect is found is greater than or equal to a predetermined number", is set.

In the present variation, the portal server 41 determines, according to the effect information having been stored for a certain piece of provision information, whether or not the provision condition for the certain piece of provision information is to be updated. Specifically, the portal server 41 specifies the number-of-pieces-of-data condition, which is associated with the provision content of the provision information in the condition update table, and determines whether or not the number of pieces of data of the stored effect information satisfies the specified number-of-pieces-of-data condition. For example, when the condition update table shown in FIG. 18 is used, the portal server 41 determines whether or not the stored number of pieces of data for the effect information reaches 100 (whether or not the effect information for 100 users has been obtained). The result of the above determination indicates that the number-of-pieces-of-data condition is not satisfied, the portal server 41 determines that the provision condition is not updated.

Meanwhile, when it is determined that the number-of-pieces-of-data condition is satisfied, the portal server 41 determines whether or not the change condition is satisfied, on the basis of the stored effect information. For example, when the condition update table shown in FIG. 18 is used, the portal server 41 determines whether or not the number of pieces of the effect information indicating that an effect is found, among the stored (100 pieces of) effect information, is greater than or equal to a predetermined number (for example, 70). The "effect information indicating that an effect is found" is the health information for which, for example, the result of the determination as to the additional provision condition that "the fatigue level has improved" shown in FIG. 14 is affirmative. That is, in the present variation, whether or not the effect information indicates that the effect is found can be determined on the basis of the result of the determination of the additional provision condition.

When it is determined that the change condition is satisfied, the portal server 41 updates the provision condition table according to the update content associated with the change condition. The update content indicates the content, to be updated, of the provision condition corresponding to the provision information, for example, indicates that "the threshold value is decreased by 0.1". For example, when the provision condition that "(the average fatigue level in the latest one week) is higher than or equal to 4" at the first line from the top in the provision condition table shown in FIG. 9 is updated according to the update content, shown in FIG. 18, that "the threshold value is decreased by 0.1", the updated provision condition is a condition that "(the average fatigue level in the latest one week) is greater than or equal to 3.9". The update content may make the provision condition more lax or may make the provision condition more strict.

In the above variation, an exemplary case where the provision condition table is updated is described. However, the service server 3 may update the additional provision condition table.

In the above variation, the provision condition table is updated according to the change condition having been satisfied. Therefore, when the change condition is repeatedly satisfied, the updating is repeatedly (in other words, continuously) performed.

As described above, the server system stores, as the storage information, the transmission information received from each terminal system and/or information (health information) obtained from the received transmission information such that the transmission information and the information obtained from the transmission information are associated with a user. The server system stores a condition (condition for determining the content of the provision information to be generated, specifically, the provision condition or the additional provision condition) related to generation of the provision information to be provided to the user for improving an index obtained from the storage information or an index included in the storage information. The server system generates the provision information on the basis of the storage information and the condition. The server system analyzes the transmission information that is related to a plurality of users to which the provision information has been provided and obtained after the provision information has been provided, and (automatically) updates the condition on the basis of the result of the analysis (the effect information). The condition is thus updated, whereby more effective provision information can be provided.

In the above variation, information obtained after the product/service introduced by the provision information has been purchased is used as "information obtained after the provision information has been provided" which is used for updating the provision condition. That is, information obtained after a time when a predetermined action due to the provision information being provided is performed, may be used as "information obtained after the provision information has been provided". The time when the predetermined action is performed may be, for example, "a time when the product/service (introduced by the provision information has been purchased" or "a time when the product/service (introduced by the provision information has been used", in the above variation.

The condition (provision condition) includes at least one health condition related to the health information. Thus, the provision information according to the health information for a user can be provided. The server system updates the health condition on the basis of a result of analysis of information obtained after the provision information has been provided. Thus, the health state of the user obtained after the provision information has been provided is analyzed, and the health condition can be updated according to the result of the analysis.

Figure 19:
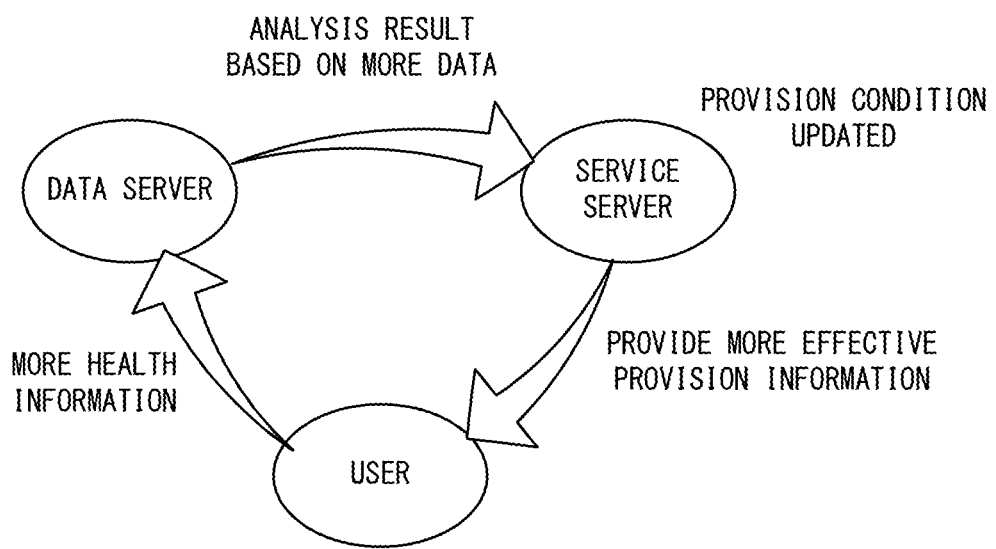
FIG. 19 illustrates an effect according to a variation.

In the above variation, the terminal system 1 repeatedly obtains the biological information of a user, and repeatedly transmits the transmission information to the server system. The server system repeatedly receives the transmission information from each of the terminal systems 1 of a plurality of users, stores and accumulates the transmission information, and continuously (repeatedly) updates the provision condition on the basis of the storage information that is stored and accumulated. The provision information is generated on the basis of the updated condition. FIG. 19 illustrates an effect according to the variation. The provision condition is updated as in the present variation, whereby the service server 3 can provide more effective provision information to the user. Effective provision information can be provided, whereby the number of users that use the service for providing the provision information are expected to be increased. Therefore, the data server 2 can obtain the health information for the increased number of users. When the increased number of pieces of the health information can be obtained, the provision condition can be updated so as to be more effective. Thus, the provision condition is automatically updated, whereby the cycle become advantageous, and more effective provision information can be provided.

The server system determines whether or not the condition is to be updated, according to calculation of a predetermined number of the analysis results having been enabled (according to the analysis results for a predetermined number of persons having been obtained). Thus, whether or not the condition is to be updated is determined when a predetermined number of the analysis results are obtained, whereby the condition can be accurately improved by the updating.

The content of each of the provision condition table and the update condition table is not limited to the above-described content. For example, the provision condition may include a priority (priority level) assigned to the provision information (provision content). When a plurality of the provision conditions are satisfied at the same time, the provision information having a higher priority (highest priority level) may be provided (generated). At this time, the update content included in the update condition table may be for changing the priority. For example, when the change condition indicating that an effect of improvement by the provision information is found (the index indicated by the health information is improved) is satisfied, the priority may be changed so as to be enhanced. Specifically, the priority level is set as "5" to "1" in order, respectively, from the highest priority level, and when the priority level for the provision information for introducing product A is "3", and the change condition indicating that an effect of improvement by product A is found, is satisfied, the priority level may be changed to "4" in the update condition table.

As described above, the provision condition may include a plurality of conditions (items) related to the health information. At this time, by the update content included in the update condition table, the item may be added or deleted, or weighting of the item may be changed.

(Variation Regarding Provision Condition)

In the above embodiment, an exemplary case is described in which, in addition to the provision condition (provision condition table) for determining the provision information, the additional provision condition (additional provision condition table) for determining the additional provision information is set. In other embodiments, the provision condition for determining the provision information may be merely set. At this time, the content of the provision condition may be automatically updated. Hereinafter, an exemplary case where the provision condition table is (merely) set and the provision condition is automatically updated, will be described as a variation of the above embodiment.

FIG. 20 illustrates an example of a provision condition table according to the variation of the above embodiment. As shown in FIG. 20, in the present variation, in the provision condition table, the provision condition, the provision content, and a subsequent provision time are associated with each other.

In the present variation, the provision condition includes a plurality of conditions containing the user condition and the health condition described above. Specifically, in FIG. 20, the provision condition includes the user condition related to the user's age, and three kinds of health conditions related to the health information (sleep index in the description herein). That is, the provision condition includes a condition related to an average in the total sleep hours for the latest one week, a condition related to an average in sleep efficiency for the latest one week, and a condition related to an average in the number of times of awakening during sleep for the latest one week. Depending on the provision content, all of these conditions need not be set. For example, depending on the provision content, as indicated in the provision condition associated with the provision content indicating "introduction of product C" shown in FIG. 20, some of the plurality of conditions may not be set. The conditions included in the provision condition are not limited to the above-described conditions. Another use condition and/or another health condition may be included, or another condition (for example, condition related to a history of purchasing of the product/service) different from the user condition and the health conditions, may be included. Thus, in another embodiment, the provision condition may include a plurality of user conditions or may merely include one health condition.

As in the above embodiment, the provision content indicates the content of the provision information that is generated (provided) when the provision condition associated therewith is satisfied.

The subsequent provision time represents a time when, in a case where the provision information having the provision content associated therewith is provided, the provision information is thereafter provided (again) (to be precise, a time when whether or not the provision information is to be provided is determined). In the present embodiment, similarly to the additional provision time (FIG. 14) described above, the subsequent provision time represents a time that elapses from purchase of the product/service. However, in another embodiment, the subsequent provision time may represent a time from a time when the immediately preceding provision information has been provided. When a time when the product has been actually used or a time when the service has been actually performed, is obtained by the portal server 341, the subsequent provision time may represent a time from this time.

In the present variation, instead of the provision condition table (FIG. 9) described in the above embodiment, the provision condition table shown in FIG. 20 is used. Also in the present variation, as in the above embodiment, determination process (steps S14 and S18) related to the provision information is executed. In the determination process, whether or not the provision information to be provided is determined, and the provision information to be provided is determined when the provision information is provided. Also in the present variation, as in the above embodiment, when each condition included in the provision condition is satisfied, the provision information having the provision content associated with the provision condition is provided. For example, the provision condition table shown in FIG. 20 indicates that, when a user is in his/her 40s, an average in the total sleep hours for the latest one week is less than six hours, an average in sleep efficiency for the latest one week is less than 80%, and an average in the number of times of awakening during sleep for the latest one week is greater than or equal to 3, the provision information for introducing product A is determined as the information to be provided.

In other embodiments, in a case where the provision condition includes a plurality of conditions, when a predetermined number of conditions among the plurality of conditions are satisfied, the portal server 41 may determine that the provision condition is satisfied. For example, in the example shown in FIG. 20, when two conditions among three heath conditions are satisfied (and the user condition is satisfied), it may be determined that the provision condition has been satisfied. In other embodiments, each condition included in the provision condition is subjected to weighting (provided with a point) by the portal server 41, and when a point of the condition that has been satisfied among the conditions is greater than or equal to a predetermined point, it may be determined that the provision condition has been satisfied.

There is no particular limitation on the method for determining whether or not the provision condition is satisfied (in other words, each condition included in the provision condition is satisfied). That is, as in the above embodiment, the portal server 41 may firstly perform determination as to the user condition and then perform determination as to the health condition associated with the user condition having been satisfied. The portal server 41 may perform determination as to the user condition and determination as to the health condition individually (in parallel).

Also in the present variation, as in the above embodiment, when the provision condition having been satisfied is present, the provision information having the content associated therewith is transmitted to the terminal system 1 (step S19).

In the present variation, when the product/service introduced by the provision information has been purchased (step S20), the portal server 41 specifies a time when the provision information is thereafter provided, on the basis of the subsequent provision time associated with the provision information. The method for specifying the time may be the same as the method for the process step (step S23) for specifying the additional provision time in the above embodiment. The specified time is stored as the subsequent provision time information. That is, in the present variation, the portal server 41 stores the subsequent provision time information, instead of the "additional provision time information" in the user provision history information (FIG. 12).

In the present variation, the portal server 41 periodically determines whether or not the subsequent provision time has come, by periodically referring to the user provision history information of each user. When it is determined that the subsequent provision time has come, the portal server 41 determines whether or not the provision information is to be provided and determines the provision information to be provided, by using the provision condition table. That is, when it is determined that the subsequent provision time has come, the portal server 41 executes the determination process (S14 and S18) related to the provision information. That is, in the present variation, in addition to when a user performs log-in, also when the subsequent provision time has come, the determination process related to the provision information is executed. The provision condition table used when the subsequent provision time has come, is the same as the provision condition table used when the user performs log-in, and the additional provision condition table is not used in the present variation.

When, as a result of execution of the determination process related to the provision information according to the subsequent provision time having come, the provision information to be provided is generated (determined), the portal server 41 transmits a message that the provision information is present, to the terminal system 1, by push notification. The method for the push notification is similar to the method for step S29 in the above embodiment. In other embodiments, the provision information itself may be transmitted to the terminal system 1 by push notification. Thus, in the present variation, when the provision information is provided according to the subsequent provision time having come, notification of the provision information (or the provision information itself) is transmitted to the terminal system 1 by push notification. Thus, a notification that the provision information has been generated, can be provided to a user at an appropriate time.

As in the present variation, the information processing system may not use the additional provision condition table. Even if the additional provision time is not set, when the subsequent provision time is set, the service server 3 can provide a user with the provision information at a predetermined time after the product/service has been purchased.

Also in the present variation, as in the above embodiment, the provision condition is updated on the basis of (a result of analysis of) the health information of the user. Also in the present variation, as in the above embodiment, the condition update table (FIG. 18) is used for updating. In the present variation, the provision condition includes a plurality of conditions (health conditions). Therefore, the change condition included in the condition update table may represent conditions related to the plurality of conditions. For example, when the provision condition table shown in FIG. 20 is used, the change condition may be as follows.

(a) Among users for whom the total sleep hours or the sleep efficiency have improved after purchase of the product, a rate of users for whom the sleep efficiency has been 70% to 80% before purchase of the product is less than or equal to 30%, and a rate of users for whom the sleep efficiency has been less than or equal to 70% before purchase of the product is greater than or equal to 60%.

(b) Among users for whom the total sleep hours or the sleep efficiency have been reduced after purchase of the product, a rate of users for whom the condition of the number of times of awakening during sleep has been satisfied before purchase of the product has been greater than or equal to 80%.

(c) Among users for whom the total sleep hours or the sleep efficiency have improved after purchase of the product, a rate of users for whom WASO has been longer than or equal to one hour before purchase of the product is greater than or equal to 80%.

As in the above (c), the change condition may include a condition related to the health information (information of WASO in the example of the above (c)) different form the health information included in the provision condition table.

When the provision condition includes a plurality of conditions (health conditions), the update content in the condition update table may be such that some (or all) of the plurality of conditions are updated. For example, when the provision condition table shown in FIG. 20 is used, the change content may be "the threshold value for the sleep efficiency is decreased by 5". For example, the change content may be associated with the change condition in the above (a).

The change content may indicate that a new condition is added in the provision condition table. For example, when the provision condition table shown in FIG. 20 is used, the change content may indicate that a condition related to a new health information is added such as "the health condition that "WASO is longer than or equal to one hour" is added". For example, the change content may be associated with the change condition in the above (c).

When each condition in the provision condition table is subjected to weighting, the change content may indicate that the weighting is changed. For example, the change content may be "weighting of a condition related to the number of times of awakening during sleep is reduced." For example, the change content may be associated with the change condition in the above (b). As described above, when priority is assigned to the provision information, the change content may indicate that the priority is changed.

The number-of-pieces-of-data condition, which is included in the update condition, may be a condition which is satisfied repeatedly when the number of pieces of data is increased. The number-of-pieces-of-data condition may be a condition that is satisfied each time a predetermined number of pieces of the effect information (for 100 persons) is obtained, for example, each time "the number of pieces of the effect information is increased by an amount corresponding to 100 persons". In this case, the service server 3 may perform determination as to the change condition on the basis of the increased predetermined number of pieces of data (corresponding to 100 persons).

As described above, the service server 3 may repeatedly determine whether or not the condition is to be updated, according to the condition (the number-of-pieces-of-data condition) related to the number of analysis results, having been satisfied. Thus, by repeated update, the content of the provision condition (or the additional provision condition) can be repeatedly improved. As a result, an accuracy of the provision condition can be enhanced.

As described above, in the present variation, at least one of the following processes is performed as a process of updating the provision condition.

(a) Change of priority set for the provision condition (b) Change of a parameter (for example, the threshold value defined for the health condition) defined in the health condition (c) Change of a parameter set for the health condition (for example, weighting for the health condition)

(d) Addition and/or deletion of the health condition included in the provision condition The provision condition is updated according to the above (a) to (d), whereby an accuracy of the provision condition can be enhanced.

(Variation Regarding Change Information)

The service server 3 (portal server 41) may store change information indicating the health information before and after purchase, for the purchased product service. At this time, the change information may be used as a part of the above-described effect information, or may be used for calculating the effect information. Hereinafter, an exemplary case where the change information is used will be described as the variation of the above embodiment.

FIG. 21 illustrates an example of the change information. In FIG. 21, the change information is information indicating sets in each of which the purchase information, the user information, the health information before purchase, and the health information after purchase are associated with each other. The purchase information represents information indicating the product/service purchased by a user. The purchase information is stored additionally each time the product/service is purchased. Therefore, as shown in FIG. 21, the change information may include a plurality of kinds of the above sets for a single product. The user information represents information related to a user who has purchased the product/service. In the present variation, information representing an age and gender of a user is stored as the user information.

The health information before purchase is the health information, of a user (who has purchased product), obtained before purchase of the product. In the present variation, for the health information such as the total sleep hours, the sleep efficiency, and the sleep onset latency, information indicating an average value of the health information in one week immediately before purchase is stored as the health information before purchase. The health information stored as the health information before purchase is not limited to the above described information and may be optionally set. For example, for various kinds of the health information stored in the data server 2, the health information before purchase (and the health information after purchase) may be stored.

The health information after purchase represents the health information, of a user, obtained after purchase of the product. The health information after purchase is the same kind of health information as the health information, before purchase, associated therewith. That is, in the example shown in FIG. 21, information related to the health information such as the total sleep hours, the sleep efficiency, and the sleep onset latency is stored as the health information after purchase. In the present embodiment, for the health information, information indicating an average value in one week immediately after the purchase is stored as the health information after purchase.

The content of the health information before purchase and the content of the health information after purchase may represent information related to the health information of which the kind is different for each product indicated by the purchase information. For example, for product A and product B, information (average value) related to three kinds of the health information such as the total sleep hours, the sleep efficiency, and the sleep onset latency is stored as the health information before purchase and the health information after purchase. Meanwhile, for product C, information related to the total sleep hours and the fatigue level may be stored as the health information before purchase and the health information after purchase.

Each of the content of the health information before purchase and the content of the health information after purchase may be different for each product indicated by the purchase information. For example, for product A and product B, an average value in one week immediately before purchase and an average value in one week immediately after purchase are stored as the health information before purchase and the health information after purchase. Meanwhile, for product C, an average value in one month immediately before purchase and an average value in one month immediately after purchase may be stored as the health information before purchase and the health information after purchase.

In other embodiments, the change information may be of any form when the change information indicates change of the health state of a user. For example, the change information may include information indicating change in the health information between before purchase and after purchase, instead of the health information before purchase and the health information after purchase. The change information may include information indicating that, for example, "the total sleep hours have increased by 0.5 hours" or "the sleep efficiency has improved".

The change information may be stored for each provision information (product/service or the like), or may be stored for each user information (age and gender, or the like).

When the product has been purchased (S20), the portal server 41 stores the purchase information, the user information, and the health information before purchase among the change information. The health information before purchase is calculated by information used for the calculation being obtained from the data server 2. The portal server 41 may calculate the change information not only when the product/service introduced by the provision information has been purchased but also when the product/service which is not introduced by the provision information has been purchased via the portal site 41. Thus, the service server 3 can collect an increased amount of data for determining an effect of the product/service, whereby the effect can be accurately determined.

When a predetermined period has elapsed after purchase of the product, the portal server 41 obtains and stores the health information after purchase. The predetermined period may be a previously determined period (one week in the example shown in FIG. 21). As described above, the predetermined period may be different for each product. The predetermined period may be set as a period for the additional provision time corresponding to the product or a period for the subsequent provision time corresponding to the product. Thus, the portal server 41 can perform the process of calculating the change information and the determination process related to the additional provision information (or the provision information) at the same timing, whereby the process can be efficiently performed. For example, in the above two processes, the process of obtaining the information from the data server 2 and the process of calculating a statistic based on the obtained information can be performed in common, whereby the process can be efficiently performed.

Similarly to the calculation of the health information before purchase, the portal server 41 obtains the information used for calculation from the data server 2, and calculates the health information after purchase by using the obtained information. When information indicating a change in the health information between before purchase and after purchase is calculated, the portal server 41 calculates the information indicating the change on the basis of the health information before purchase and the health information after purchase.

The change information having been calculated as described above may be, for example, used as (a part of) the effect information described above, or may be used for calculating the effect information. When the provision information is generated by using a result of the analysis of the health information related to another user (details thereof will be described below), the change information may be used as (a part of) the result of the analysis, or may be used for calculating the result of the analysis.

As described above, the server system stores the change information in which the provision information provided to a user is associated with change, in the health information of the user, obtained before and after a predetermined reference time based on the provision information having been provided to the user. The server system updates the provision condition (or the additional provision condition) on the basis of the change information (by using the change information as the result of the analysis or on the basis of the result of the analysis obtained by using the change information). Thus, the change information is stored, whereby the result of the analysis related to the health information, is easily calculated and updating can be facilitated.

(Variation Regarding Generation of Provision Information)

In other embodiments, the server system may generate the provision information on the basis of the result of the analysis related to one or more other users different from a user to whom the provision information is provided. For example, the server system may select, for example, the following user as the other users.

Another user who has purchased the same product as the user to which the provision information is provided.

Another user who has the user information (such as age, generation, and/or gender) similar to the user information of a user to whom the provision information is provided.

Another user who has the health information close to the health information of a user to whom the provision information is provided.

As described above, the server system may select another user on the basis of the information related to a user to whom the provision information is provided, and determine the content of the provision information on the basis of the result of the analysis related to the health information of the selected user. Thus, the useful provision information is likely to be provided to a user.

(Variation Regarding Content of Provision Information)

In the above embodiment, the provision information is information (recommendation information) for introducing the product/service. In the above embodiment and variation, the provision information may be any information for improving an index related to user's health and/or body. For example, the provision information may be advice information indicating advice for improving the index. The advice information may be, for example, (a) advice for recommending an exercise to a user for whom the health information indicating that sleep is light during sleeping has been calculated, (b) advice for recommending reconsideration of nutritional balance in meals to a user for whom the health information indicating that fatigue has been accumulated has been calculated, and (c) advice for recommending improvement of lifestyle to a user for whom the health information indicating that the sleep hours or a bedtime are irregular has been calculated. As in the above embodiment, when the provision information (advice information or the like) is repeatedly provided, the provision information is further provided on the basis of the health information, of the user, obtained after a certain piece of provision information has been provided. Thus, since the provision information such as the advice information is repeatedly (continuously) provided to a user, the user is effectively promoted to improve his/her health.

When the provision information is the advice information, the service server 3 compares the health information obtained before providing of the advice information to a user with the health information obtained after providing of the advice information to the user, and may provide additional advice information as the above-described additional provision information on the basis of the result of the comparison. That is, the service server 3 may provide the advice information such that the advice information is different between when the user's health is determined to have improved and when the user's health is determined to have not improved, as a result of the comparison.

The service server 3 may update the provision condition of the advice information. That is, the service server 3 compares the health information obtained before providing of the advice information to the user with the health information obtained after providing of the advice information to the user. When the service server 3 determines, as a result of the comparison, that the user's health has improved after providing of the advice information as compared to before providing thereof, the service server 3 may update the provision condition of the advice information such that the advice information is likely to be provided. Also when the provision information is the advice information, the update condition may be automatically updated by using, for example, the condition update table as in the variation described in "(Variation in which provision condition is automatically updated)". For example, the service server 3 may set a condition related to change in the health information of the user between before providing of the advice information and after providing of the advice information, as an update condition in the condition update table.

The provision information may be data (for example, data of music for inducing sleep onset or wake-up of a user as described above) of the product/service itself for improving the index. That is, the provision information may be information for introducing the information (information for introducing the product/service, or the advice information) to a user, may be advice itself to be provided to the user, or may be data itself of the product/service. The provision information may be information (information for introducing the product/service or information including data of the product/service (itself)) related to the product/service, or may be the advice information (which is not related to the product/service).

In the above embodiment and variation, the provision information is for introducing the product/service, and the information processing system thus uses, as the reference time, a time at which the product/service is purchased (or a time at which the product/service is used), to perform various processes. For example, in the above embodiment, a period is designated such that a time of purchase is used as the reference time for the use information (FIG. 9) described above, or a time of the purchase is used as the reference time for the additional provision time (FIG. 14) or the subsequent provision time. In the above variation, a time of the purchase is used as the reference time for the change information (FIG. 21) (the change information represents change in the health information between before the reference time and after the reference time). Meanwhile, when the provision information itself, such as the advice information or data of the product/service, is used, a time when the provision information is provided may be used as a reference.

(Variation Regarding Content of Health Information)

In the above embodiment, the health information is information that indicates an index related to user's sleep and/or fatigue. Therefore, in the present embodiment, the provision information according to user's sleep and/or fatigue can be provided. In other embodiments, the health information may be information indicating, in addition to (or instead of) an index related to sleep and/or fatigue, an index related to fatness (for example, a body weight, a body fat rate, or a basal metabolic rate), or an index related to skin condition (for example, index indicating a moisture content of skin or a state of a spot).

(Variation Regarding Configuration of Service Server)

In the above embodiment, the service server 3 includes the portal server 41 and the service providing server 42, and the shopping site through which the product/service is purchased, is managed by the portal server 41. The service server 3 may have any configuration, and the functions (roles) of the portal server 41 and the service providing server 42 are not limited to the above embodiment. For example, in another embodiment, one or more service providing servers manage the shopping sites, respectively, and the provision information can be provided and the health information can be viewed on the portal site managed by the portal server. At this time, the provision information included in a page of the portal site may include link information for access to the shopping sites. When the product/service has been purchased on the shopping site, a notification of the purchase may be transmitted from the service providing server 42 to the portal server 41 in order to manage the purchasing (purchase history) by the portal server 41. In other embodiments, the function of the portal server 41 and the function of the service providing server 42 may be provided by one server.

(Variation Regarding Product/Service)

In other embodiments, the product/service provided by the service server 3 may be an application to be provided to the terminal system 1. At this time, the application may use the information (health information or the like) stored in the data server 2. The application described above, may be, for example, an application for performing a watching service in which the biological information obtained by the terminal system 1 is used to confirm that a user is alive and make a notification thereof to another user.

In other embodiments, by the server, a game may be provided. The server that provides the game may be the same server as the service server 3 or may be a dedicated server (game server). For example, a game application may be provided to a user on the portal site managed by the portal server 41. The game application may be such an application as to operate on a browser for viewing of the portal site, or may be such an application as to be downloaded and installed from the server to the terminal system 1.

The game application may be obtained by the terminal system 1 in any method as well as the game application is provided from the server to the terminal system 1. For example, a storage medium having the game application stored therein is connected (or mounted) to the main terminal device 10, whereby the game application may be executed by the main terminal device 10.

The game application may be executed by the main terminal device 10 or may be executed by another user terminal (a mobile terminal, a personal computer, a game device, or the like) of a user.

As described above, when the game application is executed by a user terminal (the main terminal device 10 and/or the other user terminal described above), a result of evaluation of the health information of the user may be reflected in the game. Specifically, the service server 3 evaluates the health information, of the user, stored in the data server 2. That is, the service server 3 determines whether or not the health information satisfies a predetermined condition. The predetermined condition is, for example, a condition that a state where the fatigue level indicated by the health information is higher than or equal to a reference value and has a good value, has continued for a predetermined period, or a condition that the fatigue level has improved by a predetermine reference value or more. When the condition is satisfied, the service server 3 gives a privilege in the game to the user. For example, the service server 3 may provide the user with a content such as an item used in the game, or advance a story in the game. By giving such a privilege, the user can have a motivation for continuing calculation of the health information.

In the above configuration, the information processing system that includes the terminal system and the server system executes the game process based on the game application. The information processing system refers to the health information stored in the server system when executing the game process. A predetermined process during the game process is executed on the basis of the health information having been referred to (according to a result of the referring). The predetermined process is, for example, a process for providing the above-described item, or a process for advancing a story in the game. Specifically, the information processing system performs a process of adding or updating the game data used in the game application. That is, for example, the game data of an item to be provided is added or a flag in the game is updated so as to allow a new story to be played.

The game process may be executed by the information processing device (for example, the game server or the service server) on the server side. Alternatively, the game process may be executed by the information processing device (for example, the main terminal device 10 or the other user terminal described above) on the terminal side. The game process may be executed by the information processing device on the server side and the information processing device on the terminal side cooperating with each other. That is, one part of the game process may be executed on the server side, and the other part of the game process may be executed on the terminal side. For example, when the game application operates on a browser for viewing of the portal site, the game process is executed on the server side, or executed by cooperation on both the server side and the terminal side. When the game application is installed in the information processing device on the terminal side, or when the game application stored in a storage medium connected to the information processing device is executed, the game process is executed on the terminal side or executed by cooperation on both the server side and the terminal side.

Adding or updating of the game data may be executed on the server side or may be executed on the terminal side. That is, the information processing device on the server side performs adding or updating of the game data stored in the storage section on the server side or the terminal side, whereby the process of adding or updating the game data may be executed. Alternatively, the information processing device on the terminal side performs adding or updating of the game data stored in the storage section on the terminal side, whereby the process of adding or updating the game data may be executed.

As described above, in the game application, when the health information is used (referred to), the health information related to a user of the game application is referred to. For example, when the game application is used in a state where the user logs in the portal site, the server can specify the user by the user identification information that is inputted at the log-in. That is, the server stores the user identification information that is inputted at the log-in, and when the health information is referred to in the game process, the health information of the user specified by the stored user identification information is referred to.

When the game application is used in a state where a user does not log in the portal site (or when the game application is used with the use of a terminal different from a terminal that performs log-in), the server identifies the user who uses the game application before or during the game process. Specifically, the user terminal that uses the game application receives the user identification information inputted from the user before or during the game process, and transmits the inputted user identification information to the server. The server specifies the health information to be referred to, by using the user identification information received from the user terminal. When adding or updating of the game data is executed on the server side, the server executes a predetermined process (addition or change of the game data) in the game process, by referring to the specified health information, on the basis of the health information having been referred to. Meanwhile, when adding or updating of the game data is executed on the terminal side, the server transmits the specified health information to the user terminal. The user terminal executes the predetermined process in the game process, by referring to the received health information (that is, referring to the health information stored on the server side), on the basis of the health information having been referred to.

In the above configuration, the user identification information may double as a user's account at the portal site and an account in a service for providing the game application. In this case, the user's account is made common among a plurality of network services (including the service for providing the provision information, and the service for providing the game application), whereby the user can use the plurality of network services in different user terminals (which may be terminals having different platforms) in common, thereby improving usability.

Second Embodiment

Next, an information processing system, an information processing device, an information processing program and an information processing method according to the second embodiment will be described. The "(Variation in which provision condition is automatically updated)" of the first embodiment described above is directed to an example in which the provision condition is updated for all the users. The second embodiment is directed to an example in which the provision condition is updated for each user. In the second embodiment, the provision condition is customized for each user, and it is therefore possible to provide information suitable for the user. The details of the second embodiment will now be described.

[1. Configuration of Information Processing System]

In the configuration of the second embodiment, the information processing system includes a terminal system 100 to be described later, instead of the terminal system 1 of the first embodiment. Note however that also in the second embodiment, as in the first embodiment, the terminal system may be of any configuration. For example, the information processing system may include both of the terminal system 1 of the first embodiment and the terminal system 100 of the second embodiment. That is, the information processing system may include different terminal systems.

Figure 22:
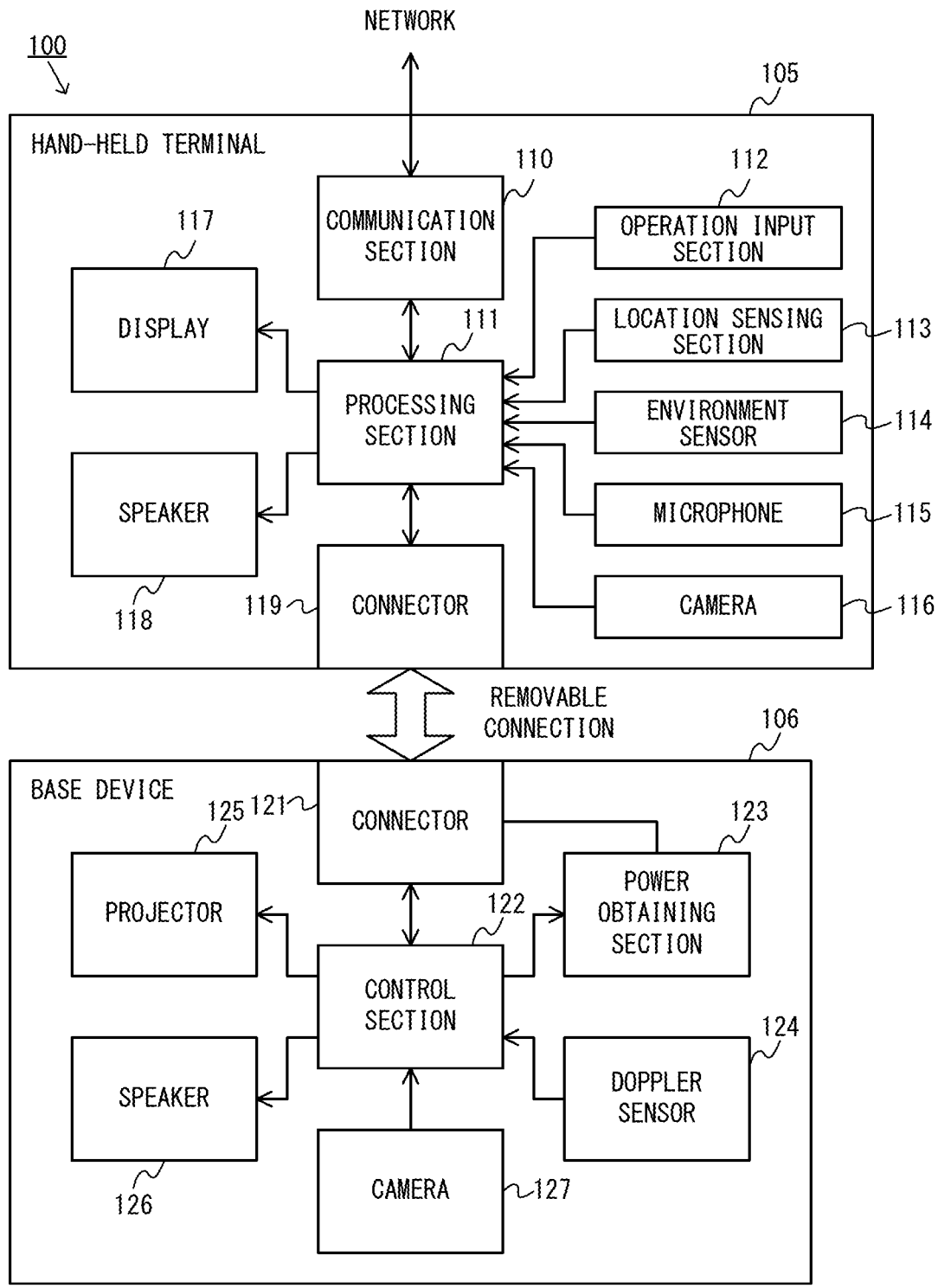
FIG. 22 illustrates an example detailed configuration of the terminal system according to the second embodiment.
Figure 23:
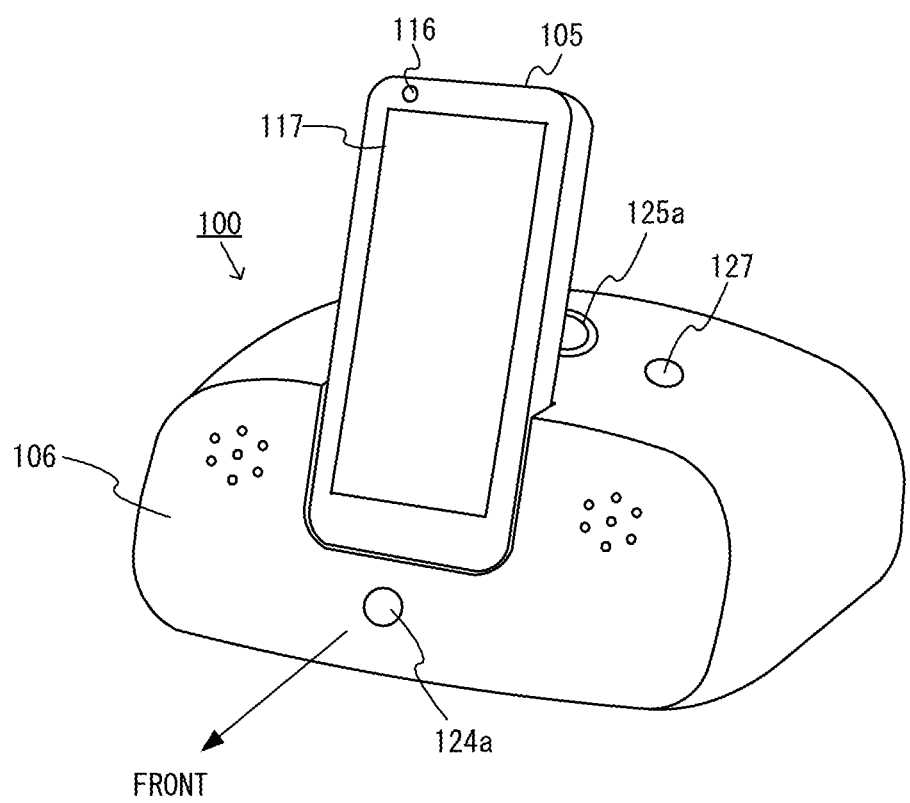
FIG. 23 illustrates an example external appearance of the terminal system according to the second embodiment.

Next, one example of the configuration of the terminal system 100 will be described. FIG. 22 shows one example of the detailed configuration of the terminal system 100. FIG. 23 shows one example of the external appearance of the terminal system 100. As shown in FIGS. 22 to 23, the terminal system 100 includes the hand-held terminal 105 and the base device 106. The hand-held terminal 105 is carried by the user. The base device 106 is placed in the house of the user, for example.

In the present embodiment, the hand-held terminal 105 is a hand-held type information processing device, and the base device 106 is a cradle that is connectable to the hand-held terminal 105. As shown in FIG. 23, the hand-held terminal 105 can connect to the base device 106 in a detachable/reattachable manner. In addition, the base device 106 has a function of performing charging with regard to the hand-held terminal 105, and, when the hand-held terminal 105 and the base device 106 are connected, charging of the hand-held terminal 105 by the base device 106 becomes possible. In other embodiments, a configuration in which the hand-held terminal 105 and the base device 106 are detachably/reattachably connected via a cable may be used.

There is no particular limitation on the communication method between the hand-held terminal 105 and the base device 106, and it may be wired communication via a cable or wireless communication such as radio wave communication and infrared communication. The communication between the hand-held terminal 105 and the base device 106 may be performed by a communication method in which communication is made directly therebetween or may be performed by a communication method in which communication is made via a network such as a LAN or the Internet.

First, the configuration of the hand-held terminal 105 in the present embodiment will be described. The hand-held terminal 105 is a hand-held type information processing device, and, in the present embodiment, is a multifunctional device such as, for example, a mobile phone, a smart phone, or a tablet terminal. Thus, the hand-held terminal 105 has some of the various types of functions (e.g., input function, output (display) function, information processing function, network communication function, telephone call function, camera function, etc.) included in a general multifunctional device. The network communication function is a communication function realized through the Internet and/or a communication function realized through a mobile communication network. The hand-held terminal 105 may be attained by installing predetermined functions on an off-the-shelf multifunctional device. In the present embodiment, the hand-held terminal 105 is used for, in addition to being used as the multifunctional device described above, calculating the health information described above or executing the game process described above. Furthermore, the hand-held terminal 105 may be an information processing device that can be worn by the user such as, for example, a wrist watch-type or goggle-type terminal (i.e., a wearable terminal).

As shown in FIG. 22, the hand-held terminal 105 includes a communication section 110. The communication section 110 connects to the network 4 to perform communication with the server (i.e., the data server 2 and/or the service server 3). In the present embodiment, the communication section 110 is a communication module having the function of connecting to a mobile communication network (in other words, mobile phone communication network) to perform communication. For example, the communication section 110 performs communication with a communication method in compliance with telecommunications standards of 3G or telecommunications standards of 4G (including LTE (Long Term Evolution)). It should be noted that there is no particular limitation on the method with which the hand-held terminal 105 communicates with the server, e.g., a method with which a communication module with Wi-Fi authentication performs communication through a wireless LAN. In addition, the hand-held terminal 105 may have a function of communicating with the server through the mobile communication network and a function of performing communication with the server through the wireless LAN.

The hand-held terminal 105 includes a processing section 111. The processing section 111 executes various types of information processing to be executed by the hand-held terminal 105. The processing section 111 is connected to the various sections 110, and 112 to 119 of the hand-held terminal 105. The processing section 111 has a CPU (Central Processing Unit) and a memory. In the hand-held terminal 105, the various types of information processing described above are executed as a result of the CPU using the memory and executing an information processing program stored in the hand-held terminal 105. In the present embodiment, the processing section 111 executes, as the information process, a process for calculating the health information described above, a game process, and a process for providing the user with the information (e.g., the service information) received from the server, etc. When the hand-held terminal 105 operates as a multifunctional device, the processing section 111 executes information processes for achieving various functions.

The hand-held terminal 105 includes an input/output interface, and functions as an information processing device (in other words, input/output terminal) for allowing the user to input and browse information. Specifically, the hand-held terminal 105 includes an operation input section 112, a display 117, and a speaker 118. The operation input section 112 is an input device of any type for accepting an operation input by the user. In the present embodiment, the operation input section 112 includes buttons and a touch panel provided on the display 117. In other embodiments, the hand-held terminal 105 may include, as the operation input section 112, a sensor (acceleration sensor, gyro sensor) for sensing the operation of moving the hand-held terminal 105.

The display 117, which is one example of the output device, displays various types of images generated on the hand-held terminal 105 in response to an input on the operation input section 112, and displays various types of images (e.g., images relating to the network service) based on data received from the server. The speaker 118, which is one example of the output device, outputs various types of sounds generated by the hand-held terminal 105 in response to an input on the operation input section 112, and outputs various types of sounds (e.g., music and audio relating to the network service) based on the data received from the server.

The hand-held terminal 105 includes a sensor for sensing information for calculating the health information. In the present embodiment, the hand-held terminal 105 includes a location sensing section 113 and an environment sensor 114.

The location sensing section 113 senses the location of the hand-held terminal 105. In the present embodiment, the location sensing section 113 senses the location by using the GNSS (Global Navigation Satellite System). The location sensing section 113 is, for example, a GPS (Global Positioning System) sensor (e.g., GPS module). It should be noted that there is no particular limitation on the location sensing method by the location sensing section 113, and the location sensing section 113 may sense the location by using, for example, a beacon. Furthermore, for example, the location sensing section 113 may calculate information (e.g., information indicating at which floor of the building one is located) indicating the altitude of the user by calculating the change in altitude based on a sensing result from an atmospheric pressure sensor.

The environment sensor 114 senses the environment surrounding the hand-held terminal 105. In the present embodiment, the environment sensor 114 includes a temperature sensor and a humidity sensor. In other embodiments, an atmospheric pressure sensor, an luminous intensity sensor, a noise sensor, a smell sensor, or the like may be included in the environment sensor 114. More specifically, the environment sensor 114 may be one that senses at least one of temperature, humidity, illumination intensity, atmospheric pressure, sound, and smell. Furthermore, in another embodiment, the microphone 115 may be used as an environment sensor for sensing noise in the surrounding area.

The hand-held terminal 105 also includes the microphone 115. The microphone 115 senses sound in the surrounding area of the hand-held terminal 105. The microphone 115 may be used for calculating the health information. For example, the hand-held terminal 105 may sense the sound of snoring of the user by means of the microphone 115, and calculate sleep-related information based on the sensing result. The microphone 115 may be used for accepting an audio input on the hand-held terminal 105.

The hand-held terminal 105 includes a camera 116. The camera 116 is, for example, disposed on the same side (e.g., inner side) where the display 117 is disposed on the hand-held terminal 105 (see FIG. 23). Thus, the camera 116 is disposed at a position enabling capturing an image of the user who is operating the hand-held terminal 105. Note that the hand-held terminal 105 may determine the facial expression of the user based on the image captured by the camera 116 to calculate the fatigue level based on the facial expression of the user.

The hand-held terminal 105 includes a connector 119 for forming an electrical connection with the base device 106. In the present embodiment, when the hand-held terminal 105 is mounted on the base device 106 (see FIG. 23), the connector 119 makes contact with a connector 121 of the base device 106. With this, communication between the hand-held terminal 105 and the base device 106 becomes possible.

It should be noted that the hand-held terminal 105 includes a battery that is not diagrammatically represented, and each section of the hand-held terminal 105 operates by the power supplied from the battery. Although details will be described later, in the present embodiment, the battery of the hand-held terminal 105 can be charged by the base device 106.

Next, the configuration of the base device 106 in the present embodiment will be described. In the present embodiment, the base device 106 is disposed, for example, at the bedroom of the user, and is used for sensing biological information relating to sleep of the user while the user is in bed. Here, the biological information is information sensed from the body of the user. In the present embodiment, breathing, pulse, and body movements are sensed as the biological information. Note that in other embodiments, any information may be sensed as biological information, and any one or two of breathing, pulse and body movements may be sensed, or information other than these three information may be sensed. In addition, the base device 106 is used for providing the user in bed with a content item (e.g., a content item that induces the user to fall asleep) and information (e.g., information of evaluation results relating to sleep).

The base device 106 includes a support section for detachably/reattachably supporting the hand-held terminal 105. Specifically, as shown in FIG. 23, a recessed portion in accordance with the shape of one portion of the hand-held terminal 105 is formed on a casing (specifically, support section) of the base device 106. When the hand-held terminal 105 is inserted in this recessed portion, the hand-held terminal 105 becomes mounted on the base device 106. Note that any mechanism may be used, with which the hand-held terminal 105 is supported on the base device 106.

As shown in FIG. 22, the base device 106 includes the connector 121. When the hand-held terminal 105 is inserted in the recessed portion, the connector 119 of the hand-held terminal 105 and a connector 121 of the base device 106 are connected. As a result, communication between the hand-held terminal 105 and the base device 106 becomes possible, and charging of the hand-held terminal 105 by the base device 106 becomes possible.

The base device 106 includes a Doppler sensor 124 which is one example of the sensor for sensing the biological information. The Doppler sensor 124, by discharging microwaves and receiving reflected waves of the discharged microwaves, senses a moving object based on a difference between the frequency of the discharged microwaves and the frequency of the received microwaves. In the present embodiment, the Doppler sensor 124 (more specifically, an emission section 124*a*) emits radio waves in the forward direction of the base device 106 (see FIG. 23). In the present embodiment, the subject to be sensed by the Doppler sensor 124 is the user, and body movements of the user are sensed by the Doppler sensor 124. Although details will be described later, analysis such as frequency analysis performed on the sensed biological information (in other words, output waveforms of the Doppler sensor 124) allows further calculation of biological information other than body movements such as breathing and pulse.

The base device 106 includes a power obtaining section 123 for obtaining power from an external power supply. In the present embodiment, the base device 106 is (may be detachably/reattachably) connected to a power plug and an AC adapter via a power cord that is not diagrammatically represented. When the power plug is connected to an electrical outlet which is an external power supply, power is supplied to the power obtaining section 123 of the base device 106. The base device 106 operates by the power from the external power supply obtained by the power obtaining section 123. In addition, the power obtaining section 123 performs charging of the hand-held terminal 105 by transmitting the supplied power to the hand-held terminal 105 through the connector 121. In other embodiments, the base device 106 may include a battery, and power charged in the battery may be transmitted to the hand-held terminal 105. Furthermore, in the present embodiment, although charging is performed in a mode in which power is supplied through the connector, in other embodiments, power may be supplied through non-contact charging.

The base device 106 includes a projector 125 for projecting an image on a screen or a wall surface (including the ceiling). The projector 125 may be any display device that displays an image on a surface (may be uneven) away from the base device 106 by projecting the image on the surface. In the present embodiment, as shown in FIG. 23, a projector 125 is formed on the base device 106 such that a light projection section (specifically, lens) 125*a* faces upward, i.e., such that the image is projected upward. More specifically, in the present embodiment, the projector 125 projects the image on the ceiling. In the present embodiment, for example, the projector 125 may display an image that induces the user to fall asleep or wake up (e.g., a sleep-inducing content item to be described later, etc.), and displays an image showing an evaluation result of sleep when the user awakens in the morning.

In the present embodiment, the base device 106 corrects the image to be projected on the ceiling by using, if necessary, a technology of so-called projection mapping. More specifically, the base device 106 corrects the image such that an image in accordance with the unevenness and/or the color of the projection plane (i.e., the ceiling) of the projector 125 is displayed. Note that conventional methods may be used as the method for correcting the image. The base device 106 includes a camera 127 for correcting the image. As shown in FIG. 23, the camera 127 is formed on the base device 106 in a direction that includes an image capturing range of the location where the image is to be projected by the projector 125. Thus, the camera 127 is provided so as to face the same direction (i.e., upward) as the projector 125.

The base device 106 includes a speaker 126. The speaker 126 is used for, for example, outputting a sound that induces the user to fall asleep or wake up (e.g., a sleep-inducing content item, etc., to be described later).

The base device 106 includes a control section 122 that controls the various sections 123 to 127 of the base device 106. The control section 122 is connected to each of the sections 121 and 123 to 127 of the base device 106. The control section 122 executes various types of control processes executed by the base device 106. The control section 122 has a memory and a CPU. In the base device 106, the various types of control processes are executed when the CPU uses the memory and executes information processing programs stored in the base device 106. For example, a control section 122 controls charging operation of the hand-held terminal 105 by controlling the power obtaining section 123. In addition, the control section 122 causes the projector 125 and/or the speaker 126 to reproduce information and a content item to be provided to the user on the base device. Furthermore, the control section 122 transmits information sensed by the Doppler sensor 124 to the hand-held terminal 105.

It should be noted that the base device 106 may include other elements in addition to or instead of those shown in FIG. 22. For example, the base device 106 may include an environment sensor, a display, a nondirectional speaker, a light source (e.g., illumination), and/or a smell generation device, etc. Note that when the base device 106 includes an environment sensor, the hand-held terminal 105 may not include an environment sensor. The hand-held terminal 105 and the base device 106 may include environment sensors of the same type (i.e., environment sensors that sense the same information) or may include environment sensors of different types.

Note that the configuration of the data server 2 and the service server 3 of the second embodiment (which may be referred to simply as "the server" in the description of the present embodiment) is similar to that of the first embodiment. Therefore, also in the second embodiment, as in the first embodiment, the terminal system 100 transmits the health information to the server, and the server generates the provision information based on the health information to transmit the provision information to the terminal system 100. Note however that in the second embodiment, the terminal system 100 itself also executes the process of deciding the provision information to be provided to the user. Therefore, in the second embodiment, the server does not need to execute the process of transmitting the provision information to the terminal system 100.

[2. Operation of Terminal System]

(2-1: Outline of Operation of Terminal System)

Next, the outline of the operation of the terminal system 100 according to the second embodiment will be described. The following description is directed to an example in which a tune to be reproduced as a sleep-inducing content item is provided as the provision information to be provided to the user. Note that a sleep-inducing content item is a piece of music and/or an image (which may be a still image or a video) that induces the user to fall asleep. That is, in the present embodiment, a tune for inducing the user to fall asleep is reproduced when the user gets in bed. The terminal system 100 first presents, to the user, information representing candidate tunes to be reproduced (referred to as candidate tunes), and reproduces a tune selected by the user from among the candidate tunes. Therefore, in the present embodiment, the information of candidate tunes can be said to be the provision information, or a tune that is actually reproduced can be said to be the provision information.

The terminal system 100 has a decision rule for deciding candidate tunes pre-stored, and decides candidate tunes in accordance with the decision rule. Note that the decision rule is a condition for deciding information of a candidate tune (or a tune that is actually reproduced), which is the provision information, and it can therefore be said that the decision rule is a provision condition described above. In the present embodiment, the decision rule is updated for each user. That is, in the present embodiment, the provision condition is set for each user, and is customized for each user. The outline of the flow of the process of the terminal system 100 will now be described with reference to FIG. 24.

Figure 24:
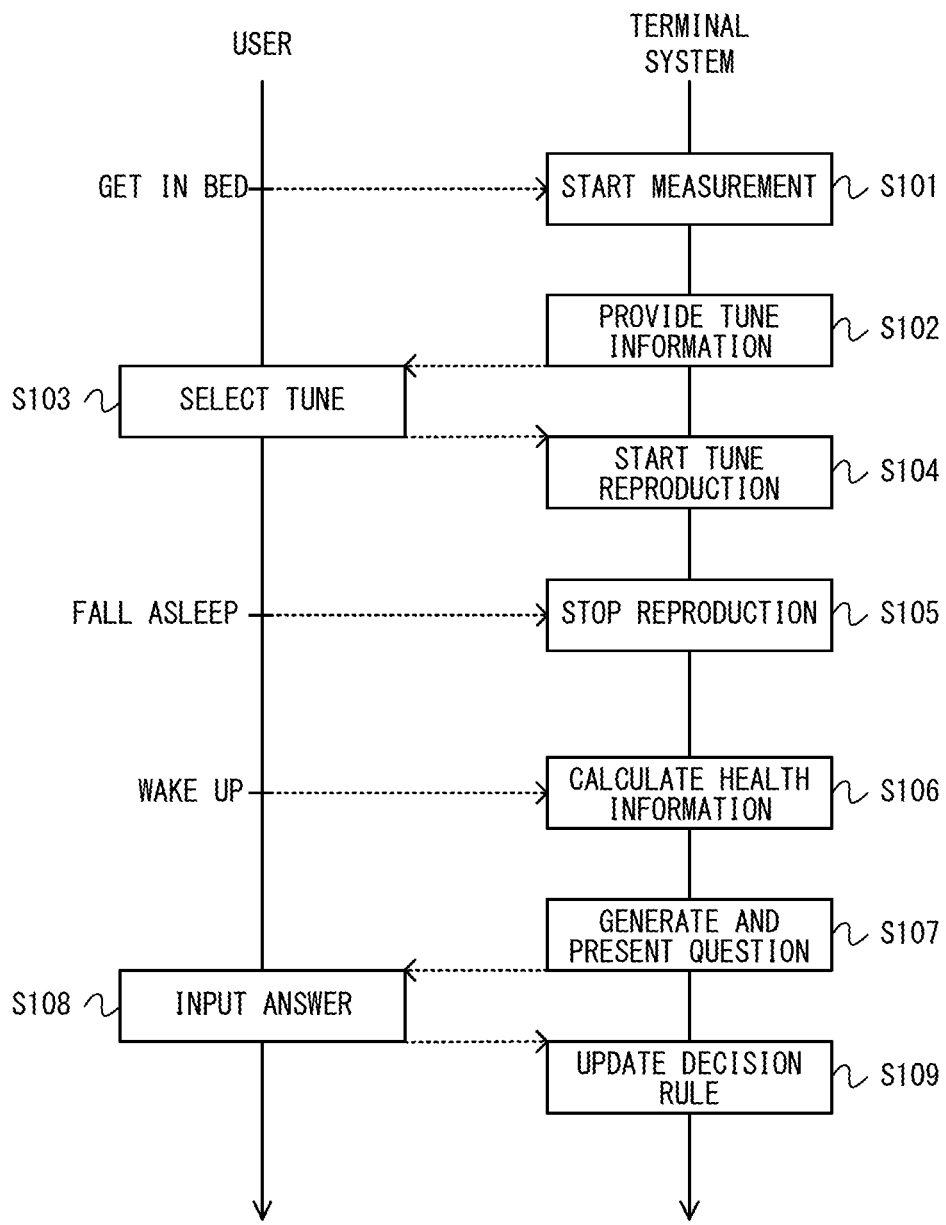
FIG. 24 illustrates an example flow of a process performed by the terminal system according to the second embodiment.

FIG. 24 illustrates an example flow of the process performed by the terminal system 100 according to the second embodiment. FIG. 24 shows the process to be executed by the terminal system 100 during the period from when the user gets in bed until after the user wakes up.

Also in the second embodiment, as in the first embodiment, the terminal system 100 starts measuring the biological information when the user gets in bed (step S101). Specifically, the user docks the hand-held terminal 105 onto the base device 106 when getting in bed. As the hand-held terminal 105 is docked onto the base device 106, the terminal system 100 determines that the user has gotten in bed (i.e., senses the user getting in bed). In response to sensing the user getting in bed, the terminal system 100 starts the measurement for calculating the health information of the user.

The method for calculating the health information in the second embodiment is similar to that of the first embodiment, and the health information including the sleep indices and the fatigue index is calculated. Note that it is assumed in the second embodiment that the hand-held terminal 105 has the functions of the various sections shown in FIG. 4. That is, in the second embodiment, the biological information is transmitted from the base device 106 to the hand-held terminal 105, and the hand-held terminal 105 calculates the health information based on the biological information. Note that in other embodiments, the functions of the various sections shown in FIG. 4 may be provided in the hand-held terminal 105 or may be provided in the base device 106.

Note that there is no particular limitation on the condition for starting the measurement. For example, in other embodiments, in which the hand-held terminal 105 and the base device 106 capable of wireless communication with each other, the base device 106 may start the measurement in response to an instruction for starting the measurement being transmitted from the hand-held terminal 105 to the base device 106. The base device 106 may determine, at intervals of a predetermined amount of time, whether or not the user is around the base device 106 by using the Doppler sensor 124, for example, and start the measurement in response to determining that the user is around.

Next, the terminal system 100 executes the process of providing the user with the information representing candidate tunes described above (step S102). In the present embodiment, the hand-held terminal 105 decides candidate tunes based on the health information that has been calculated so far (i.e., health information that has been calculated based on the biological information obtained in past sleep periods). The hand-held terminal 105 identifies the tendency of sleep for the past one week to decide candidate tunes in accordance with the tendency, the details of which will be described later. For example, when it is identified that the user tends to have trouble falling asleep (have long sleep latencies), tunes that are thought to be effective in helping the user fall asleep are decided as candidate tunes. The hand-held terminal 105 provides the user with information representing the decided candidate tunes (e.g., the titles of the tunes) as the provision information. Specifically, information representing the decided candidate tunes is displayed on the display 117 of the hand-held terminal 105.

Figure 25:
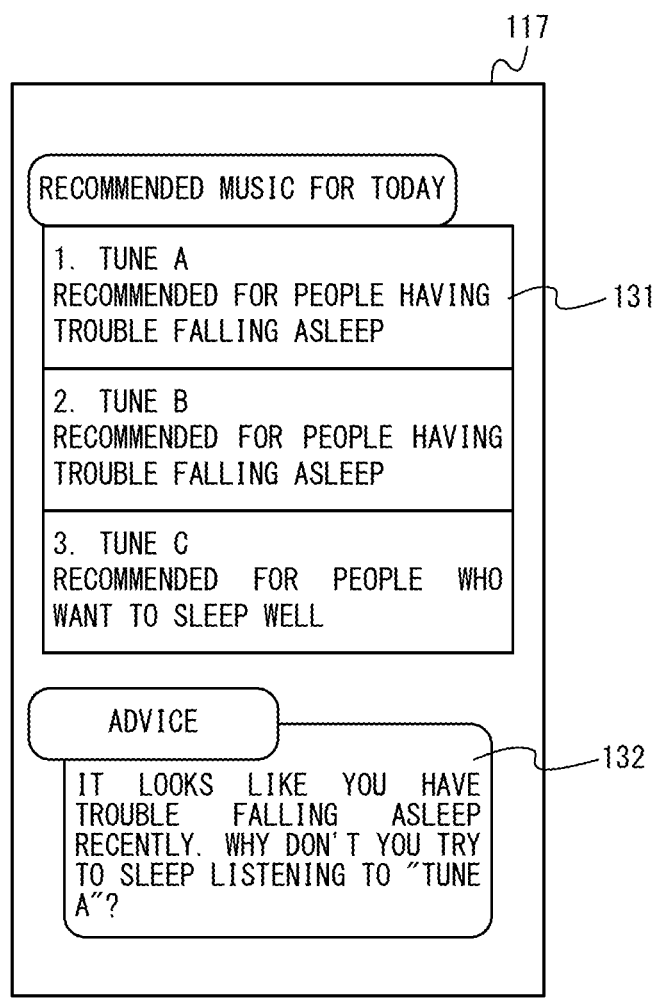
FIG. 25 illustrates an example image to be displayed on a hand-held terminal for providing information representing candidate tunes.

FIG. 25 illustrates an example image to be displayed on the hand-held terminal 105 for providing information representing candidate tunes. As shown in FIG. 25, a candidate tune image 131 representing the decided candidate tunes is displayed on the display 117 of the hand-held terminal 105. Note that the present embodiment is directed to an example in which three tunes (Tunes A to C in FIG. 25) are presented to the user as candidate tunes, but there may be any number of candidate tunes. In the present embodiment, an advice image 132 representing advice information for the user is displayed, together with the candidate tune image 131. The advice image 132 will be described later.

As the tune information image 131 is displayed on the display 117, the user selects a tune of interest from among the candidate tune (step S103). The selection of a tune is done, for example, by the operation of touching on the tune of interest from among the candidate tunes displayed on the display 117. In response to this operation, the hand-held terminal 105 starts reproducing the selected tune (step S104). Specifically, the hand-held terminal 105 transmits the sound data of the tune to the base device 106, and the base device 106, having received the sound data, outputs the tune from the speaker 126. Note that in other embodiments, the tune may be reproduced from a speaker 118 of the hand-held terminal 105, in addition to (or instead of) from the speaker 126 of the base device 106.

Note that a list of tunes that can be reproduced by the hand-held terminal 105 (in other words, a list of tunes from which candidate tunes are selected) may be stored in the hand-held terminal 105 or may be stored in the server. When the list is stored in the server, the hand-held terminal 105 obtains the list from the server at an appropriate point in time (e.g., at a point in time when step S102 is executed). The sound data of the tunes included in the list may be stored in the hand-held terminal 105 or may be stored in the server. When the sound data of the tunes is stored in the server, the hand-held terminal 105 obtains the sound data of selected tunes from the server at a point in time when the tune to be reproduced is selected, for example.

In the present embodiment, in a period of time during which the user is asleep (referred to as a sleep period), the terminal system 100 determines the sleep state of the user based on the biological information (and the health information) during this period, and controls the operation of the hand-held terminal 105 in accordance with the sleep state. Specifically, the hand-held terminal 105 determines whether or not the user has fallen asleep based on the obtained biological information. Then, if it is determined that the user has fallen asleep, the hand-held terminal 105 stops the reproduction of the tune, which was started in step S104 described above (step S105). This is because it is not so needed to reproduce the tune because the user has fallen asleep. Note that in other embodiments, the hand-held terminal 105 may stop the reproduction of the tune after the passage of a predetermined amount of time from the point in time when the user falls asleep, or may stop the reproduction of the tune at a point in time when it is determined that the user is in a deep sleep (in the non-REM sleep state). In other embodiments, the tune does not need to be stopped depending on the sleep state of the user. For example, in other embodiments, the reproduction of a tune may be stopped after the passage of a predetermined amount of time from the start of the reproduction of the tune.

In other embodiments, the terminal system 100 may control operations other than controlling the reproduction of a tune. For example, in other embodiments, the terminal system 100 may perform a control of changing the state of the hand-held terminal 105 (e.g., turning the power OFF, switching to the stand-by state, switching to the manner mode, etc.) depending on the sleep state of the user.

When the user wakes up, the terminal system 100 calculates the health information for the current sleep period (step S106). As described above, the terminal system 100 calculates the health information based on the biological information obtained in the current sleep period by a method similar to the first embodiment. Note that it is possible to determine that the user has woken up based on the biological information.

Next, the hand-held terminal 105 generates a question for the user, and presents the generated question to the user (step S107). The question is generated based on the health information calculated in step S106, the details of which will be described later. For example, if it is determined, from the calculated health information, that the number of mid-sleep awakenings is greater than normal (i.e., there is a significant difference between the currently-calculated number of mid-sleep awakenings and the average value), the hand-held terminal 105 asks a question such as "Did you sleep well?". If the fatigue level of the user is higher than normal, for example, the hand-held terminal 105 asks a question such as "Did you recover from fatigue?".

Figure 26:
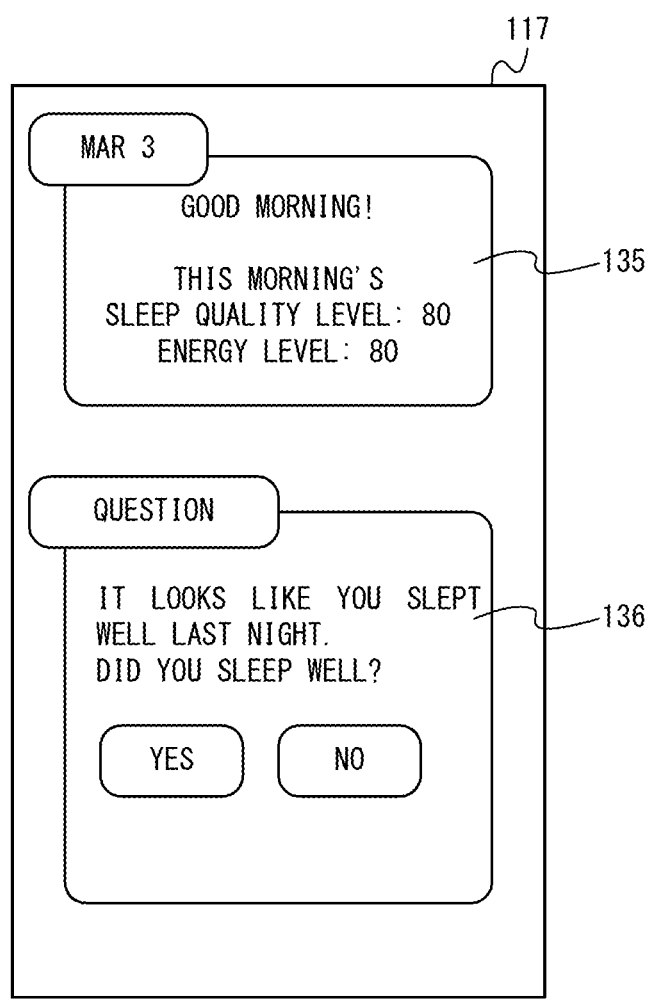
FIG. 26 illustrates an example image to be displayed on the hand-held terminal at the time of awakening.

FIG. 26 illustrates an example image to be displayed on the hand-held terminal 105 at the time of awakening. As shown in FIG. 26, when the user wakes up, an evaluation result image 135 and a question image 136 are displayed on the display 117.

The evaluation result image 135 represents the evaluation result relating to sleep and fatigue for the current sleep period. Specifically, the evaluation result image 135 represents the sleep quality level and the energy level, which are the evaluation result calculated based on the biological information (and the health information). The sleep quality level is an index (specifically, a numerical value) representing how good the sleep is (which can also be called the quality of sleep). While there is no particular limitation on the method for calculating the sleep quality level, the sleep quality level is calculated based on the sleep indices described above so that a higher numerical value represents a better state, for example. The energy level is a numerical value calculated for the purpose of representing the user's health state (the state of sleep and fatigue level in the present embodiment) in an easy-to-understand manner for the user. The energy level is calculated based on the fatigue level described above, for example, and a higher numerical value represents a better state (in other words, a lower fatigue level). The energy level may be calculated by any method, and the energy level may be calculated by, for example, subtracting the fatigue level from 100. Thus, in the present embodiment, the sleep quality level and the energy level are calculated as the evaluation result relating to the health information. Note that the sleep quality level and the energy level as described above are also types of health information. In the present embodiment, the evaluation result relating to the health information is presented to the user when the user wakes up, and the user can therefore know the evaluation result immediately after waking up.

The question image 136 represents the question generated in step S107. In FIG. 26, the question image 136 representing the question "Did you sleep well?" is generated and displayed. In the present embodiment, the question image 136 includes button images (specifically, button images representing "Yes" and "No") used by the user to answer. Note that the answer of the user may be given in any form, e.g., a form in which the user selects an answer from among two or more choices, or a form in which the user inputs a numerical value.

When the question image 136 is displayed on the display 117, the user inputs an answer to the question (step S108). In the present embodiment, the user gives an answer by making an input of specifying (specifically, an input of touching) a button image included in the question image 136.

In response to the answer being input, the hand-held terminal 105 updates the decision rule (step S109). The decision rule is updated based on the health information calculated in step S106 and the answer of the user input in step S108, the details of which will be described later. For example, when the health information indicates that the health state is good or when the user input is an answer indicating that the health state is good, it can be determined that the tune, as a sleep-inducing content item, reproduced when falling asleep was effective (or the effectiveness was significant) for the user. Therefore, in such a case, the decision rule is updated so that this tune will more likely be selected. On the other hand, when the health information indicates a poor state or when the user input is an answer indicating that the health state is poor, it can be determined that the tune, as a sleep-inducing content item, reproduced when falling asleep was not effective (or the effectiveness was insignificant) for the user. Therefore, in such a case, the decision rule is updated so that this tune will less likely be selected.

As described above, in the second embodiment, the terminal system 100 can provide the user with information of candidate tunes that are decided based on the health information (step S102). Thus, the terminal system 100 can recommend suitable tunes, as sleep-inducing content items, to the user based on the health information.

Moreover, in the second embodiment, the terminal system 100 determines the effectiveness (specifically, the presence/absence and the degree of effectiveness) of the tune provided when the user awakens out of sleep (step S106, S107). The decision rule for deciding the tune is updated based on the determination result. Since the decision rule is updated based on the user health information of each individual user and the answer of each individual user, the decision rule becomes customized for each user. Thus, the terminal system 100 can provide provision information suitable for each user, and it is possible to provide information that is useful for each individual user.

(2-2: Tune Providing Process)

Next, a specific example of the tune provision process (steps S102 to S104 described above) to be executed on the terminal system 100 will be described. As described above, the tune provision process is a process of providing a tune (and candidate tunes) to be reproduced when the user falls asleep.

Figure 27:
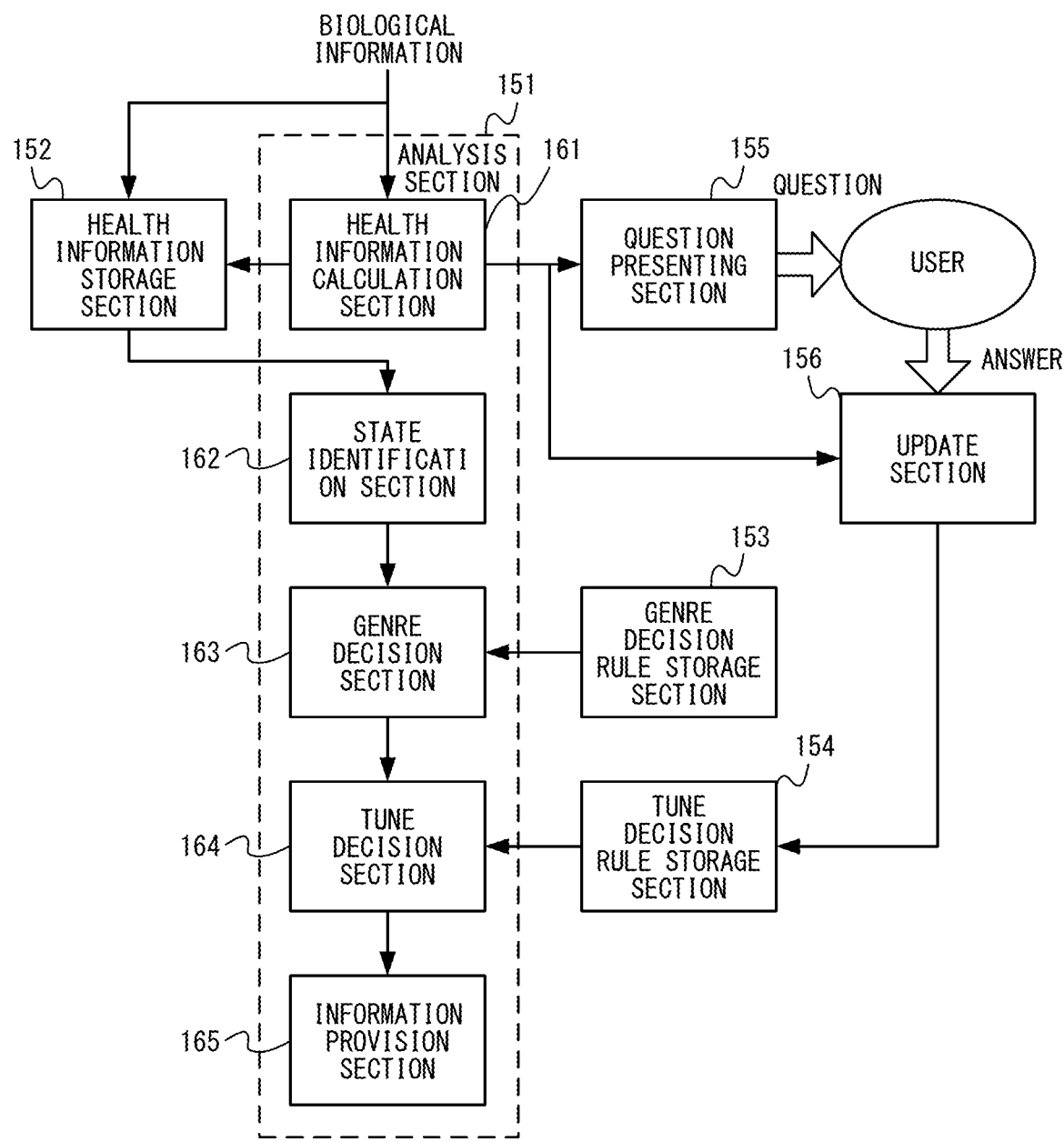
FIG. 27 is a functional block diagram illustrating an example functional configuration of the terminal system.

FIG. 27 is a functional block diagram showing an example functional configuration of the terminal system 100. In the present embodiment, as elements for executing the tune provision process, the terminal system 100 includes an analysis section 151, a health information storage section 152, a genre decision rule storage section 153, and a tune decision rule storage section 154 (a question presenting section 155 and an update section 156 will be described later). In the present embodiment, the various sections 151 to 154 are implemented by the processing section 111 and/or the storage section (not shown) of the hand-held terminal 105. Specifically, the analysis section 151 is implemented by the processing section 111 executing a predetermined information processing program. The various storage sections 152 to 154 are implemented by the predetermined storage section described above. The predetermined storage section is any storage medium that can be accessed by the processing section first portion 1, and it may be a storage medium built in the hand-held terminal 105 or may be an external storage medium that can be attached to/detached from the hand-held terminal 105.

The analysis section 151 performs an analysis relating to the health of a user based on the biological information of the user, and provides the user with information based on the analysis result (information of candidate tunes and a tune to be reproduced). As shown in FIG. 27, the analysis section 151 includes a health information calculation section 161, a state identification section 162, a genre decision section 163, a tune decision section 164, and an information provision section 165.

The health information calculation section 161 obtains the biological information sensed by the base device 106, and calculates the health information based on the obtained biological information. The method for calculating the health information is similar to that of the first embodiment. The calculated health information is output to the health information storage section 152.

The health information storage section 152 stores the biological information sensed by the base device 106 and the health information calculated by the health information calculation section 161. The health information storage section 152 stores the latest biological information and health information and those obtained in the past over a predetermined storage period (e.g., three months). Therefore, when the biological information and the health information are obtained, the health information storage section 152 updates the information so that information for the storage period is stored. Note that in the present embodiment, the health information storage section 152 does not need to store all types of sensed biological information and calculated health information, but may store those of the sensed biological information and the calculated health information that are used for deciding candidate tunes.

Based on the health information of a user, the state identification section 162 identifies (or "estimates") the health state of the user. In the present embodiment, as the health state of the user, the state identification section 162 calculates the sleep tendency for a predetermined period of time (e.g., the past one week). Specifically, the state identification section 162 obtains the health information from the health information storage section 152, and calculates at least the average sleep latency and the average number of mid-sleep awakenings for the past one week based on the obtained health information. Note that there is no particular limitation on the information to be calculated as the health state. The state identification section 162 may calculate a state relating to a sleep index other than the sleep latency and the number of mid-sleep awakenings, or may calculate a state relating to fatigue, for example. The information to be calculated as the health state may be calculated based on the latest health information of the user (e.g., the health information calculated based on the latest sleep episode) and past health information as in the present embodiment, or may be calculated based on the latest health information of the user in other embodiments. The information calculated as the health state may be calculated based on health information of the user and health information of other users. For example, in other embodiments, the state identification section 162 may calculate, as the health state, information based on a comparison between the health information of the user (e.g., the sleep latency) and health information of other users (e.g., the average value of the sleep latency for the other users) (e.g., the difference between the sleep latency of the user and the average value). Note that the terminal system 100 may obtain the health information of other users from the server at an appropriate point in time.

The genre decision section 163 decides a genre of candidate tunes to be provided to the user based on the health state identified by the state identification section 162. In the present embodiment, tunes that can be reproduced by the hand-held terminal 105 described above are each assigned a genre. That is, in the list of tunes that can be reproduced, the identification information of each tune is associated with information representing the genre of the tune. The genre decision section 163 decides a predetermined number (herein, one) of genres from among a plurality of different genres assigned to different tunes.

The decision of a genre is made by using a genre decision rule. The genre decision rule storage section 153 stores the genre decision rule. FIG. 28 illustrates an example genre decision rule. In the present embodiment, as shown in FIG. 28, the genre decision rule is information that associates the condition relating to sleep tendency (the sleep condition) with the weight set for each genre. Note that although not shown in the figure, the genre decision rule includes information that associates each genre with a reference weight value predetermined for that genre.

The genre decision section 163 determines, for each sleep condition, whether the identified health information satisfies the sleep condition included in the genre decision rule, and identifies the setting associated with the satisfied sleep condition. The genre decision section 163 changes the weight value assigned to each genre in accordance with the identified setting. For example, in the example shown in FIG. 28, if the identified health information indicates that the sleep latency is 15 minutes or less and that the number of mid-sleep awakenings is one to three, there are identified a setting of increasing the weight value for genre A by 0.5 and a setting of increasing the weight value for genre D by 0.5. As a result, the weight values for genre A and genre D are each increased by 0.5.

As described above, in the present embodiment, changes are made to the predetermined reference weight values by using the genre decision rule. The genre decision section 163 decides the genre based on the weight values to which changes have been made. There is no particular limitation on the method for deciding the genre based on the weight values. For example, the genre decision section 163 may select a genre for which the weight value is largest. For example, the genre decision section 163 may decide the genre by using a random number so that each genre is selected with a probability based on the weight value. Then, randomness can be introduced to the genre decision, and it is possible to increase the possibility that many different genres are selected. That is, the hand-held terminal 105 can present tunes of many different genres to the user.

The tune decision section 164 decides candidate tunes from among tunes that are included in the genre decided by the genre decision section 163. The candidate tunes are decided by using the tune decision rule. The tune decision rule storage section 154 stores the tune decision rule. The tune decision rule includes a table in which each of the tunes that can be reproduced by the hand-held terminal 105 is associated with the weight assigned to the tune. FIG. 29 illustrates an example table included in the tune decision rule. In the present embodiment, as shown in FIG. 29, each tune is associated with the weight value in the table. Each tune is associated with a genre.

The tune decision section 164 selects candidate tunes (three candidate tunes in the present embodiment) from among the various tunes included in the decided genre based on the weight values assigned to the tunes. There is no particular limitation on the method for selecting candidate tunes based on the weight value. For example, the tune decision section 164 may select, as candidate tunes, a predetermined number (herein, three) of tunes, of all the tunes included in the decided genre in the descending order of the weight value. For example, the tune decision section 164 may select a predetermined number tunes by using a random number so that each tune is selected in accordance with its weight value from among the various tunes included in the decided genre. Then, randomness can be introduced to the tune decision, and it is possible to increase the possibility that many different tunes are selected. That is, the hand-held terminal 105 can present many different tunes to the user.

The information provision section 165 provides, to the user, information of each of the candidate tunes (e.g., the title of the tune) decided by the tune decision section 164. Specifically, the tune decision section 164 displays the candidate tune image 131 (see FIG. 25) on the display 117. Note that in the present embodiment, the candidate tune image 131 includes recommendation information such as "recommended for those who have trouble falling asleep", for example, in addition to the title of the candidate tune (see FIG. 25). The advice image 132 representing advice information is displayed, in addition to the candidate tune image 131 (see FIG. 25). The content of these recommendation information and advice information is determined based on the health state identified by the state identification section 162, for example. For example, a table in which the condition relating to the health state and the content of the recommendation information and advice information to be presented is pre-stored in the hand-held terminal 105, and the content of these information is identified using this table. That is, the hand-held terminal 105 identifies the content of the recommendation information and advice information associated with a condition, of all the conditions included in the table, that is satisfied by the health state. The content of information thus identified is displayed on the display 117 as the recommendation information and the advice information.

Moreover, the information provision section 165 accepts a user input of selecting one of the candidate tunes, and decides the tune selected by the user as a tune to be reproduced as a sleep-inducing content item. Then, the information provision section 165 obtains the sound data of the decided tune, and reproduces the tune by using the speaker 118. Thus, the tune is presented to the user as a sleep-inducing content item.

(2-3: Process of Updating Decision Rule)

Next, referring to FIG. 27, a specific example of the decision rule updating process to be executed on the terminal system 100 will be described. The decision rule updating process is a process of determining the effectiveness of the tune as a sleep-inducing content item (specifically, the effectiveness in improving the health state of the user) and updating the decision rule depending on the determination result. In the present embodiment, as elements for executing the decision rule updating process, the terminal system 100 includes the health information calculation section 161 described above, the question presenting section 155, and the update section 156. In the present embodiment, the sections 155 and 156 are implemented by the processing section 111 of the hand-held terminal 105 executing a predetermined information processing program.

As described above, when the user awakens, the health information calculation section 161 calculates the health information based on the biological information obtained during the current sleep period (i.e., the sleep period preceding the present awakening; in other words, the sleep period the end of which is the present awakening) (step S106 shown in FIG. 24).

The question presenting section 155 presents a question for the user based on the health information calculated by the health information calculation section 161 (step S107 shown in FIG. 24). In the present embodiment, based on the health information, the question presenting section 155 selects one of a plurality of questions that are prepared in advance. While there is no particular limitation on the method for deciding the question to be presented, the present embodiment uses a table in which conditions relating to the health information are associated with questions.

FIG. 30 illustrates an example table used for deciding a question to be presented to the user. As shown in FIG. 30, the table associates each of the conditions relating to the health information with a question to be presented when the condition is satisfied. The question presenting section 155 identifies a condition that is satisfied by the calculated health information from among the conditions included in the table, and selects a question that is associated with the identified condition. In the example shown in FIG. 30, if there is a difference of one or more between the number of mid-sleep awakenings for the current sleep period and the average value (e.g., the average value for the past one week), for example, a question "Did you sleep well?" is selected.

Note that the method for deciding a question may be a method based on the latest health information and the past health information for the user as in the present embodiment, or may be a method based on the latest health information for the user in other embodiments. The question may be decided based on the health information of the user and the health information of other users. For example, in other embodiments, the question presenting section 155 may decide a question based on information that is based on a comparison between the health information of the user (e.g., the number of mid-sleep awakenings) and information obtained from health information of other users (e.g., the average value of the number of mid-sleep awakenings for other users) (e.g., the difference between the number of mid-sleep awakenings of the user and the average value).

The question presenting section 155 generates the question image 136 representing the selected question and displays the question image 136 on the display 117. Note that when there are a plurality of questions selected, only a predetermined number (e.g., one) of questions thereof may be presented to the user, or all of the selected questions may be presented. As a question is presented as described above, the user inputs an answer to the question (step S108 shown in FIG. 24).

The update section 156 obtains the answer input by the user for the question. The update section 156 also obtains the health information calculated by the health information calculation section 161. The update section 156 updates the tune decision rule, of all the decision rules, based on the health information and the answer of the user. In the present embodiment, the tune decision rule is updated by using a rule update table, which is an example of the condition update table described above. The rule update table is stored in the tune decision rule storage section 154, for example.

FIG. 31 illustrates an example rule update table used for deciding the update content. As shown in FIG. 31, the rule update table is for associating each condition relating to the health information or the user's answer with the content of an update to be implemented when the condition is satisfied. The update section 156 identifies a condition that is satisfied by the health information or the user's answer, of all the conditions included in the rule update table, and identifies the content of the update that is associated with the identified condition. In the example shown in FIG. 31, if the sleep time is greater than or equal to the average value (e.g., the average sleep time for the past one week), for example, update content indicating an increase of the weight value by 0.1 is identified. Note that if there are a plurality of conditions satisfied, the update section 156 identifies update content that is associated with each of the plurality of conditions.

Note that the method for deciding the update content may be a method based on the latest health information and the past health information for the user as in the present embodiment, or may be a method based on the latest health information for the user in other embodiments. The update content may be decided based on the health information of the user and the health information of other users. For example, in other embodiments, the update section 156 may decide the update content based on information that is based on a comparison between the health information of the user (e.g., the sleep time) and information obtained from the health information of other users (e.g., the average value of the sleep time for other users) (e.g., the difference between the sleep time of the user and the average value).

The update section 156 updates the tune decision rule stored in the tune decision rule storage section 154 in accordance with the identified update content. Specifically, in the table included in the tune decision rule described above (see FIG. 29), the weight value associated with a tune to be updated is increased or decreased in accordance with the identified update content. Note that the "tune to be updated" is a tune that is reproduced as a sleep-inducing content item in the current sleep period.

Note that in the rule update table, a condition indicating that the health information is good or a condition such that the answer of the user indicates that the health state is good is associated with such update content that the weight value is increased (i.e., the tune to be updated will more likely be selected) (see FIG. 31). In the rule update table, a condition indicating that the health information is poor or a condition such that the answer of the user indicates that the health state is poor is associated with such update content that the weight value is decreased (i.e., the tune to be updated will less likely be selected). Therefore, in the present embodiment, when it is estimated that the tune reproduced as a sleep-inducing content item is effective in improving the sleep of the user, the tune will more likely be provided as a candidate tune in the future. On the other hand, when it is estimated that the tune reproduced as a sleep-inducing content item is not effective in improving the sleep of the user, the tune will less likely be provided as a candidate tune in the future.

Note that in other embodiments, the update of the decision rule may be done based on the health information calculated in the past, in addition to the health information for the current sleep period (i.e., new health information). For example, based on new health information and past health information, the hand-held terminal 105 may determine whether or not the health state of the user has improved and decide the update content in accordance with the determination result. Specifically, when it is determined that the health state of the user has improved, the hand-held terminal 105 may increase the weight value of the tune to be updated, and when it is determined that the health state of the user has not improved, the hand-held terminal 105 may decrease the weight value of the tune to be updated.

While the update section 156 updates the decision rule based on the calculated health information and the answer of the user in the present embodiment, it may update the decision rule based on one of the health information and the answer of the user in other embodiments. In other embodiments, the update section 156 may update the genre decision rule together with (or instead of) the tune decision rule.

There is no particular limitation on the method for updating the decision rule. In other embodiments, the update section 156 may update the condition included in the decision rule instead of (or in addition to) changing the update content (specifically, the weight value) included in the decision rule. For example, the update section 156 may change the threshold value included in the condition (e.g., the threshold value of the sleep condition included in the genre decision rule shown in FIG. 28). For example, consider a situation in which the condition "the sleep time is 6 hours or less" is set as a sleep condition in the sleep condition described above for determining if the user is having sufficient sleep. In this situation, if the calculated health information (or the answer input by the user) indicates that the health state is good even though the actual sleep time is 6 hours or less, the update section 156 may change "6 hours or less", which is the threshold value of the condition that "the sleep time is 6 hours or less", to "5 hours 50 minutes", for example.

As described above, the present embodiment is directed to an example using a table shown in FIG. 28 to FIG. 31 as a means for deciding the content of the provision information or updating the provision rule. There is no particular limitation on the means for deciding the content of the provision information or updating the provision rule. For example, the content of the provision information may be decided by an analysis engine. The analysis engine uses a predetermined algorithm to (1) analyze sleep/fatigue based on the health information, (2) evaluate characteristic portions (problems and good points) based on the analysis, (3) estimate the cause of each characteristic portion, and (4) provide a solution to the cause. Then, the update of the provision rule may be done by updating the program (in other words, updating the algorithm) of the analysis engine.

[3. Specific Example Process of Terminal System]

Figure 32:
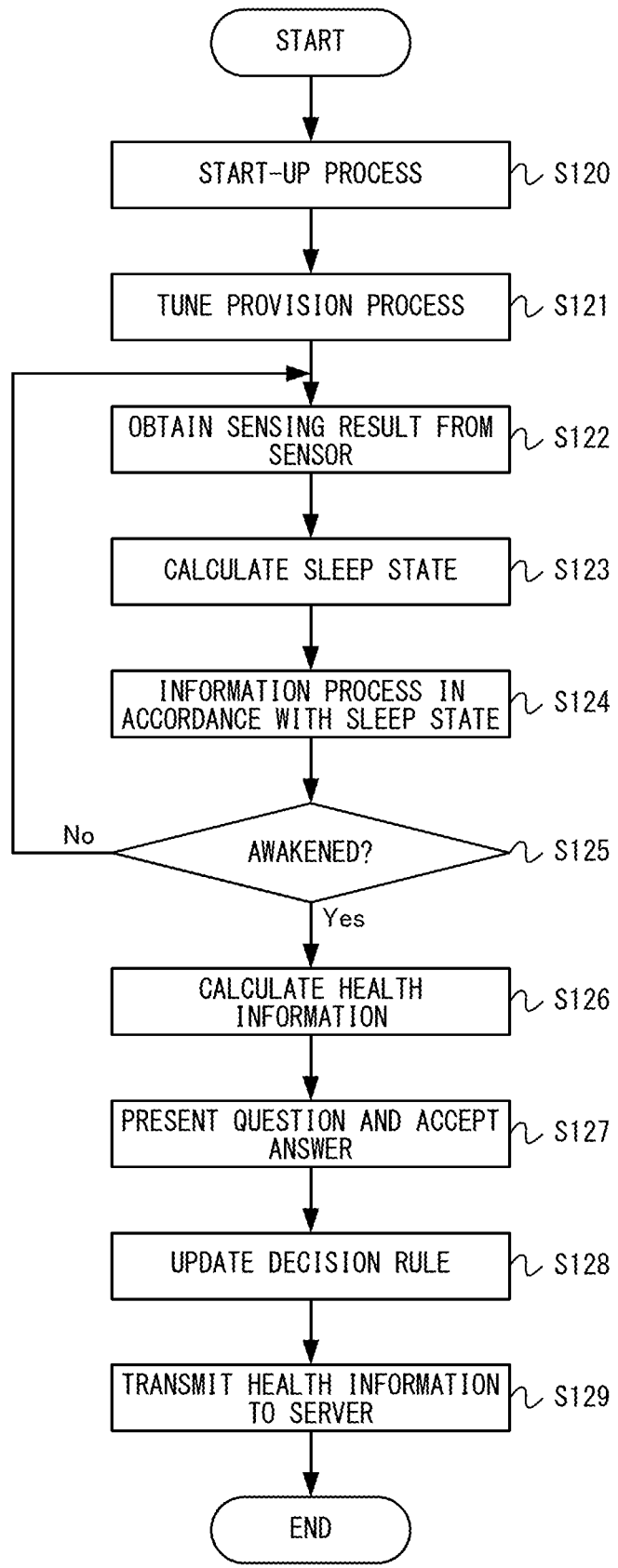
FIG. 32 is a flow chart showing an example flow of a process executed on the hand-held terminal.

Next, a specific example of the process to be executed on the terminal system according to the second embodiment will be described. FIG. 32 is a flow chart showing an example flow of a process to be executed on the hand-held terminal 105. In the present embodiment, the series of processes shown in FIG. 32 is started in response to sensing the user getting in bed, i.e., in response to the hand-held terminal 105 being docked onto the base device 106. Note that in other embodiments, the series of processes may be started in response to the start of communication between the hand-held terminal 105 and the base device 106 or in response to the user performing a predetermined start operation on the hand-held terminal 105 or the base device 106.

First, in step S120, the hand-held terminal 105 executes a start-up process. The start-up process is a process that is executed in response to the start of the series of processes shown in FIG. 32 (in response to the hand-held terminal 105 being docked onto the base device 106 in the present embodiment). Specifically, the terminal system 100 starts sensing by the sensor (i.e., the Doppler sensor 124) for sensing the biological information for calculating the health information (step S151). That is, the processing section 111 of the hand-held terminal 105 gives the base device 106 an instruction to start the sensing operation. In response to this instruction, the control section 122 of the base device 106 causes the Doppler sensor 124 to start the sensing operation.

When the start-up process of step S120 is executed (in other words, in response to the hand-held terminal 105 being docked onto the base device 106), the base device 106 executes a charge start process. In the charge start process, the base device 106 starts charging the hand-held terminal 105. Specifically, the control section 122 gives a power obtaining section 123 an instruction to start the charge. In response to this instruction, the power obtaining section 123 supplies power from an external power source to the hand-held terminal 105 via the connector 121. Note that it is assumed that the base device 106 is connected to an external power source (i.e., the power plug is connected to an outlet). Note that the base device 106 may check the remaining battery level of the hand-held terminal 105, and may start the charging operation on the condition that the remaining battery level is less than or equal to a predetermined amount. The charging operation is ended in response to the battery of the hand-held terminal 105 is fully charged.

In step S121, the hand-held terminal 105 executes the tune provision process described above (steps S102 to S104). This starts the reproduction of the tune as a sleep-inducing content item.

After the process of step S121, the process of steps S122 to S125 to be described later is executed repeatedly during the sleep period of the user. Note that in the present embodiment, the process loop of steps S122 to S125 is executed at the rate of once per a predetermined amount of time.

In step S122, the hand-held terminal 105 obtains the sensing result of the Doppler sensor 124 (i.e., the biological information). The Doppler sensor 124, which has started the sensing operation by the process of step S120 described above, outputs the sensing result (specifically, the output waveform) to the control section 122. The control section 122 transmits the sensing result to the hand-held terminal 105. Thus, the sensing result of the Doppler sensor 124 is obtained by the hand-held terminal 105. Note that the control section 122 may transmit the information of the sensing result of the Doppler sensor 124 as it is to the hand-held terminal 105, or may process the sensing result (e.g., the process of removing noise contained in the sensing result signal, the process of calculating the sleep indices, etc.) before transmitting it to the hand-held terminal 105.

In step S123, the hand-held terminal 105 calculates the sleep information (e.g., various sleep indices). That is, the processing section 111 calculates the various sleep indices based on the sensing result (i.e., the biological information) obtained in step S122. The calculation of the sleep indices is done by a method similar to that of the first embodiment. Note that in step S123, the processing section 111 may calculate the sleep information used for determining the sleep state of the user in steps S124 and S125 to be described later. In step S123, the processing section 111 may not calculate the sleep indices (e.g., the total sleep time), the fatigue information (in other words, the fatigue level) and the energy level, which can only be calculated at the end of the sleep period.

In step S124, the hand-held terminal 105 executes an information process in accordance with the sleep state of the user. That is, the processing section 111 determines whether or not the sleep state of the user has become a predetermined state. Then, when it is determined that it has become a predetermined state, the operation of the hand-held terminal 105 (and the base device 106), the operation mode and/or the settings are controlled. In the present embodiment, when it is determined that the user has fallen asleep, the processing section 111 stops the reproduction of the tune, which was started in step S121 described above (step S105 shown in FIG. 24).

In step S125, the hand-held terminal 105 determines whether or not the user has awakened. That is, the processing section 111 determines whether or not the user has awakened based on the biological information obtained in step S122 and/or the sleep indices calculated in step S123. When it is determined that the user has awakened, the series of processes of steps S126 to S129 is executed. On the other hand, if it is determined that the user has not awakened, the process of step S122 is executed again. That is, the series of processes of steps S122 to S125 is executed repeatedly until it is determined that the user has awakened.

In step S126, the hand-held terminal 105 calculates the health information based on the information obtained during the sleep period (step S106 shown in FIG. 24). The health information is calculated by a method similar to that of the first embodiment.

In step S127, the hand-held terminal 105 presents a question to the user based on the health information calculated in step S126 (step S107 shown in FIG. 24), and accepts an input of an answer to the question by the user (step S108 shown in FIG. 24). That is, the processing section 111 displays the question image 136 described above on the display 117, and obtains the input of the answer from the operation input section 112.

In step S128, the hand-held terminal 105 updates the decision rule based on the health information calculated in step S126 and the answer input by the user in step S127 (step S109 shown in FIG. 24).

In step S129, the hand-held terminal 105 transmits the health information calculated in step S126 to the server. That is, the processing section 111 transmits the calculated health information to the server by means of the communication section 110. Thus, the health information for one sleep period is transmitted to the server and stored in the server. Thus, in the present embodiment, the hand-held terminal 105 automatically transmits, to the server, information to be transmitted. That is, the information is uploaded to the server even without an instruction from the user.

After step S129 described above, the hand-held terminal 105 ends the series of processes shown in FIG. 32. The processing section 111 gives an instruction to stop the sensing operation to the base device 106. In response to this instruction, the control section 122 of the base device 106 stops the sensing operation of the Doppler sensor 124.

Note that in the present embodiment, if the hand-held terminal 105 is taken off the base device 106 for some reason (e.g., the user hitting the hand-held terminal 105 when rolling over) during the sleep period, the base device 106 cannot transmit the sensing result of the Doppler sensor 124 to the hand-held terminal 105. Then, the base device 106 stores, in its storage section (e.g., a memory, etc.), the data of the sensing result that has not been transmitted to the hand-held terminal 105. Then, in response to the hand-held terminal 105 being next docked onto the base device 106, the base device 106 transmits the data of the sensing result stored in the storage section to the hand-held terminal 105. The hand-held terminal 105, having received the data, calculates the sleep indices based on the sensing result (step S123). Note that the hand-held terminal 105 may not execute a control process based on the calculated sleep indices (step S124). This is because the calculated sleep indices are based on a past sensing result.

If it is determined that the user has awakened based on the calculated sleep indices (if the determination result of step S125 is affirmative), the hand-held terminal 105 executes the processes of steps S126 to S129 described above. Thus, even if the hand-held terminal 105 is taken off the base device 106 while the user is asleep, the decision rule is updated and the health information is transmitted to the server when the hand-held terminal 105 is next docked onto the base device 106. Therefore, when the user awakens and notices that the hand-held terminal 105 is off the base device 106, for example, the user can dock the hand-held terminal 105 onto the base device 106. Then, the terminal system 100 can update the decision rule and transmit the health information to the server.

Note that in other embodiments, when the hand-held terminal 105 and the base device 106 are capable of wireless communication with each other, the processes of steps S122 to S125 described above can be executed continuously even if the hand-held terminal 105 is taken off the base device 106.

Note that the hand-held terminal 105 may execute a process similar to the process to be executed by the main terminal device 10 in the normal mode of the first embodiment, in addition to the process shown in FIG. 32. That is, the hand-held terminal 105 may access the service server 3 to display the health information of the user on the display 16 and display the provision information provided from the service server 3 on the display 16.

[4. Variations of the Second Embodiment] (Variation in which Update is Done Based on Health Information of a Plurality of Users)

In the second embodiment, the decision rule, which is an update condition, is updated based on the personal health information of the user of the terminal system 100. In other embodiments, the decision rule may be updated based on health information of a plurality of users. In the second embodiment, the decision rule is updated for the user of the hand-held terminal 105. That is, the decision rule is one that is used only for the user himself/herself of the terminal system 100. In other embodiments, the decision rule may include a part that is common among a plurality of users. As a variation of the second embodiment, an example will now be described below in which a part of the decision rule is used commonly among a plurality of users and updated based on health information of a plurality of users.

Figure 33:
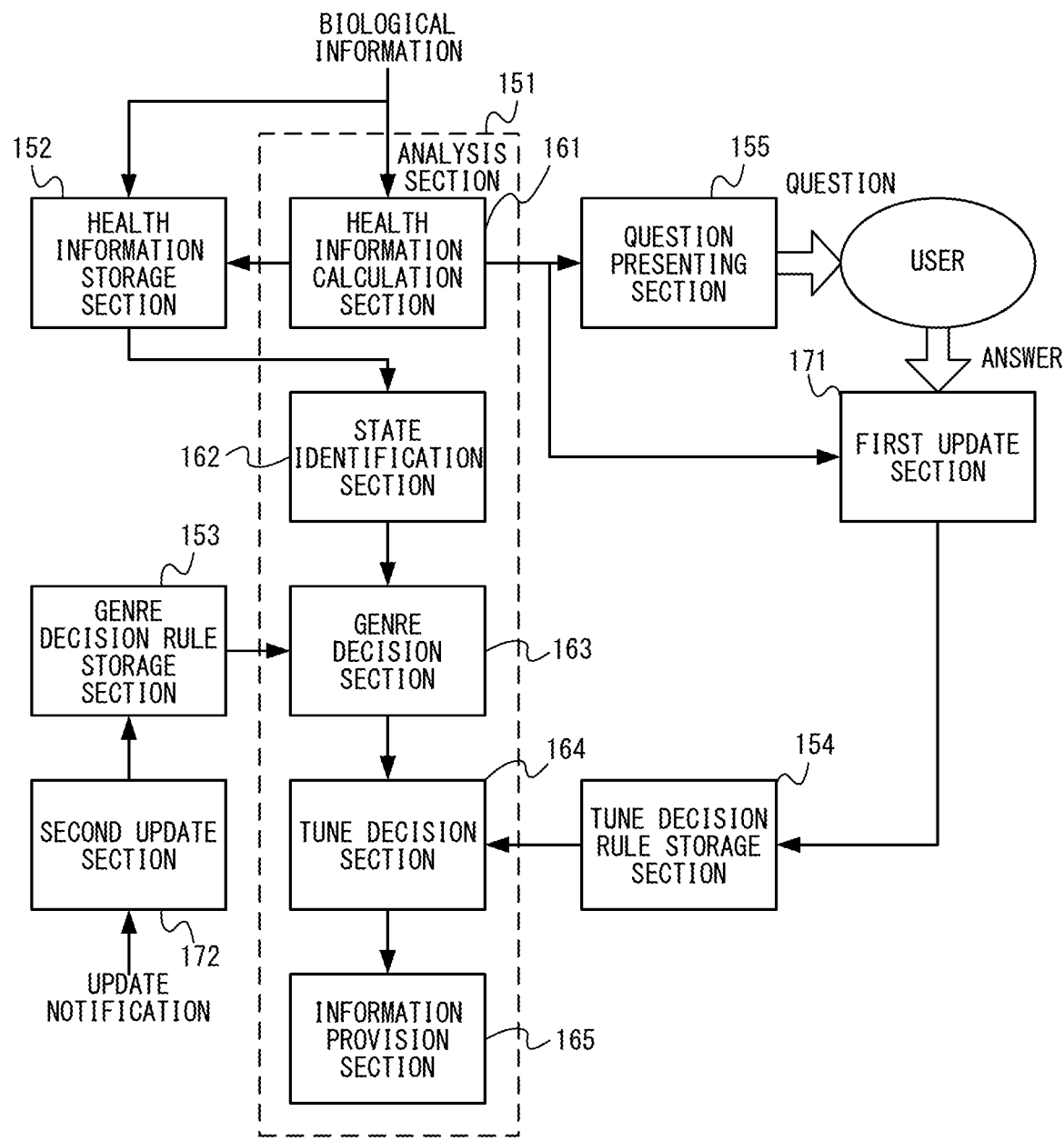
FIG. 33 is a functional block diagram illustrating an example functional configuration of a terminal system according to a variation of the second embodiment.

FIG. 33 is a functional block diagram showing an example functional configuration of the terminal system 100 according to a variation of the second embodiment. In FIG. 33, as elements for executing the decision rule updating process, the terminal system 100 includes the health information calculation section 161 described above, the question presenting section 155, a first update section 171, and a second update section 172. Note that those elements in FIG. 33 that are denoted by the same reference signs as those in FIG. 32 are the same elements as those of FIG. 32, and they will not be described below in detail.

The first update section 171 is the same as the update section 156 in the second embodiment. In this variation, the terminal system 100 includes the second update section 172 in addition to the first update section 171. In this variation, the sections 171 and 172 are implemented by the processing section 111 of the hand-held terminal 105 executing a predetermined information processing program.

The second update section 172 updates the genre decision rule, of all the decision rules. In this variation, the genre decision rule is updated based on health information of a plurality of users. Specifically, the server has a genre decision rule stored therein as a provision condition, and also stores the health information of each user received from his/her terminal system, as in the first embodiment. In addition to the health information, the server receives information representing a tune as a sleep-inducing content item from the terminal system and stores the information in association with the health information. At a predetermined point in time, the server updates the genre decision rule based on health information relating to a plurality of users.

There is no particular limitation on the predetermined point in time, and it may be a point in time that is determined by the administrator of the server (the administrator of the network service), for example. For example, the predetermined point in time may be one for which the data count condition and/or change condition set in the server, as described in "(Variation in which provision condition is automatically updated)" above. For example, the server may determine that the predetermined point in time is when a predetermined number of health information associated with tunes of a certain genre have been obtained.

There is no particular limitation on the content of update of the genre decision rule. In this variation, based on health information that is associated with tunes of a certain genre, the server determines the effectiveness of the tunes of that genre and updates the genre decision rule based on the effectiveness. For example, with an example genre decision rule shown in FIG. 28, when based on the health information associated with tunes of genre C, it is determined that the tunes are effective in shortening and improving the sleep latency, the server increases the increment ("+1" in FIG. 28) for the weight value of genre C. As described above, the server may calculate information representing whether or not the health state has improved, based on the history of health information (i.e., health information for a plurality of sleep periods), as the effectiveness of tunes as sleep-inducing content items.

When the genre decision rule is updated, server transmits, to the terminal systems, an update notification including information representing the update content. Each of the terminal systems updates the genre decision rule stored therein in accordance with the update notification. That is, when the update notification from the server is received by the terminal system 100, the second update section 172 updates the genre decision rule stored in the genre decision rule storage section 153 in accordance with the update content represented by the update notification. Thus, the content of the genre decision rule stored in the server can be synchronized with the content of the genre decision rule stored in the terminal system 100.

Note that the server may store genre decision rules that are applied to all the users of the network service, or may store genre decision rules each applied to some of the users of the network service that belong to a predetermined group. For example, depending on sex, age, address and/or hobby and preferences, etc., the users are divided into predetermined groups. The server stores a genre decision rule corresponding to each group, and when the genre decision rule is updated, the server transmits the update notification to terminal systems of the users belonging to the group. Thus, the update notification is not transmitted to terminal systems of the users not belonging to the group.

(Variation Regarding Rules)

In the variation described above, the tune decision rule is updated for each user based on health information of the user, and the genre decision rule is updated based on health information of a plurality of users. In other embodiments, the terminal system 100 may update the rules by any method that is based both on health information of each user and health information of a plurality of users. For example, in other embodiments, rules may be updated by the following method.

Figure 34:
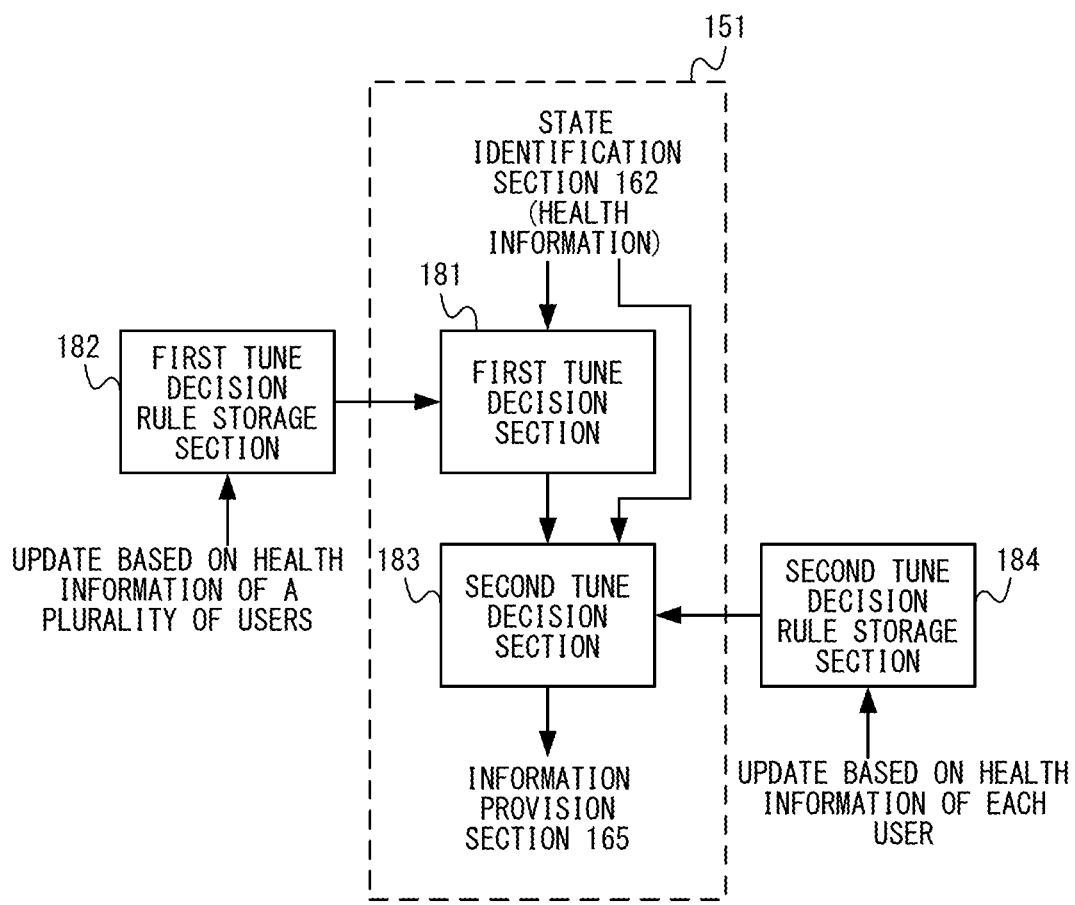
FIG. 34 is a functional block diagram illustrating an example functional configuration of a terminal system according to another variation of the second embodiment.

FIG. 34 is a functional block diagram illustrating an example functional configuration of a terminal system according to another variation of the second embodiment. Note that FIG. 34 shows only some of the functional elements of the terminal system, and the same elements as those of FIG. 27 or FIG. 33 are omitted. As shown in FIG. 34, in this variation, the analysis section 151 includes a first tune decision section 181 and a second tune decision section 183, instead of the genre decision section 163 and the tune decision section 164. The terminal system 100 includes a first tune decision rule storage section 182 and a second tune decision rule storage section 184, instead of the tune decision rule storage section 154 and the genre decision rule storage section 153.

In this variation, the first tune decision section 181 calculates the weight value of each tune that can be reproduced by the hand-held terminal 105, based on the health state identified by the state identification section 162. The weight value of the first tune decision section 181 is determined by using the first rule stored in the first tune decision rule storage section 182. There is no particular limitation on the method for deciding the weight value. For example, the weight value may be decided by using information that is obtained by changing a setting of the genre decision rule shown in FIG. 28 to a setting relating to the weight assigned to a tune. That is, a first rule may be information that associates a condition relating to the sleep tendency with a setting relating to the weight assigned to a tune. Then, the first tune decision section 181 determined, for each sleep condition included in the first rule, whether or not the health information identified by the state identification section 162 satisfies the sleep condition, and updates the weight value assigned to a tune in accordance with the setting associated with the satisfied sleep condition. Note that in this variation, the first rule is updated based on health information of a plurality of users (that is, the content of the first rule will be common among a plurality of users), the details of which will be described later.

The second tune decision section 183 correct the weight value of each tune calculated by the first tune decision section 181 based on the health state identified by the state identification section 162. The correction by the second tune decision section 183 is done by using a second rule stored in the second tune decision rule storage section 184. There is no particular limitation on the specific method of correction. For example, as a second rule, similar to the first rule, a correction may be done by using information that associates a condition relating to the sleep tendency and the correction to the weight assigned to a tune. Then, for each sleep condition, the second tune decision section 183 determines whether or not the health information identified by the state identification section 162 satisfies the sleep condition included in the second rule, and corrects the weight value assigned to a tune in accordance with a setting that is associated with the satisfied sleep condition. Note that in this variation, the second rule is updated based on the health information of each user (that is, customized for each user), the details of which will be described later.

Note that the information of the health state used by the first tune decision section 181 for calculating the weight value may be the same as, or different from, the information of the health state used by the second tune decision section 183 for correcting the weight value. For example, the first tune decision section 181 may use the health state identified by the state identification section 162 based on the latest health information of the user, while the second tune decision section 183 uses the health state identified by the state identification section 162 based on past health information of the user. For example, the first tune decision section 181 may use the health state of the first type (e.g., the sleep time), while the second tune decision section 183 uses the health state of the second type (e.g., the sleep latency).

The second tune decision section 183 selects candidate tunes as described above based on the corrected weight value. Then, the second tune decision section 183 outputs information representing the selected candidate tunes to the information provision section 165. Note that the method for selecting candidate tunes based on weight values may be similar to that of the second embodiment described above.

As described above, in this variation, the decision rules include the first rule and the second rule. In this variation, the first rule is updated based on health information of a plurality of users, and the second rule is updated based on health information of each user (see FIG. 34). Thus, also in this variation, as in the second embodiment described above, it is possible to update the provision condition for each user and to customize the provision condition for each user.

While there is no particular limitation on the method for updating the first rule, the first rule may be updated by a method similar to that for updating the genre decision rule described in the "(Variation in which update is done based on health information of a plurality of users)" above, for example. That is, although the first rule and the genre decision rule are different from each other in whether weight values are assigned to tunes or genres of tunes, a similar method can be used as the method for updating the weight value. For example, when it is determined that a certain tune is effective in improving sleep, the server updates the first rule so that the weight value of the tune is likely set to a great value. Then, the server transmits, to each terminal system, an update notification including information representing update content relating to the first rule. Each terminal system updates the first rule stored therein in accordance with the update notification.

While there is no particular limitation on the method for updating the second rule, the second rule may be updated by a method similar to that for updating the tune decision rule described in the embodiment above, for example. That is, the terminal system 100 may decide update content of the second rule in accordance with the rule update table at a point in time in response to awakening of the user. For example, when it is estimated that a tune that has been reproduced as a sleep-inducing content item is effective in improving the sleep of the user, the terminal system 100 updates the second rule so that the tune is more likely to be provided as a candidate tune in the future.

According to the variation described above, a result (the weight value) based on the first rule applied to a plurality of users is corrected based on the second rule, which is customized for each user, to decide the content of the provision information (i.e., a candidate tune) based on the corrected result. Then, the second rule allows the terminal system 100 to provide information that reflects the health state of each user, and it is possible to make a proposal suitable for each user, as in the second embodiment described above.

Note that in the variation described above, the terminal system 100 can decide a candidate tune without using the second rule (i.e., without making the correction based on the second rule) by using the weight value calculated based on the first rule. Therefore, in other embodiments, the terminal system 100 may decide a candidate tune using the weight value calculated based on the first rule, without using the second rule, under a predetermined condition. For example, the terminal system 100 may determine whether or not to use the second rule in accordance with a instruction from the user. For example, in the initial period of use of the terminal system 100, when the precision of the second rule is expected to be low (e.g., when the second rule has not been updated sufficiently), the second rule may not be used.

(Variation in which Provision Information Based on Environment Information is Provided)

In other embodiments, the terminal system 100 may provide provision information using the environment information sensed by the environment sensor 114. Specifically, the health information storage section 152 obtains and stores environment information during the sleep period of the user. The state identification section 162 calculates the tendency of sleep taking the environment information into consideration. Then, the genre decision section 163 and/or the tune decision section 164 decide the candidate tunes based on the tendency of sleep taking the environment information into consideration. For example, when the air temperature is used as the environment information, the state identification section 162 calculate the relationship between the sleep latency and the air temperature for the user of the terminal system 100. Then, if the user tends to have trouble falling asleep (i.e., have long sleep latencies) when the air temperature is low, and if it is determined that the air temperature is low based on the environment information obtained when the provision information is provided (after the user gets in bed), the genre decision section 163 may change the weight value so that a genre that is thought to be effective in helping the user fall asleep is more likely to be selected.

(Variation in which Update is Done Based on Environment Information)

In other embodiments, the terminal system 100 may update the decision rule by using the environment information sensed by the environment sensor 114. Specifically, the health information storage section 152 obtains and stores environment information during the sleep period of the user. The update section 156 decides update content of a decision rule between the health information calculated based on the biological information obtained during a sleep period and the environment information obtained during the sleep period. For example, when the weight value of a tune to be updated is changed based on the number of mid-sleep awakenings indicated by the health information, the update section 156 may decide the amount by which the weight value is changed based on the air temperature during the sleep period. That is, when the air temperature is too high or too low during the sleep period, the number of mid-sleep awakenings is believed to increase due to the air temperature. Therefore, in such a case, even if the number of mid-sleep awakenings is large, the update section 156 sets a relatively small amount as the amount by which the weight value is changed (specifically, decreased). On the other hand, when the air temperature is adequate during the sleep period (i.e., within a predetermined range), the number of mid-sleep awakenings is not believed to increase due to the air temperature. Therefore, in such a case, if the number of mid-sleep awakenings is large, the update section 156 sets a relatively large amount as the amount by which the weight value is changed (specifically, decreased).

(Variation in which Location Information is Used)

In other embodiments, the terminal system 100 may provide provision information and/or update a decision rule based on the location information sensed by the location sensing section 113. For example, the terminal system 100 may calculate activity information indicating the activities of the user for one day based on the location information. The activity information is information that is calculated from the history of location information for one day, and may be information representing the amount by which the user traveled (e.g., the number of steps) or information representing the activities of the user (e.g., worked at the workplace, went to the gym, etc.), for example. The terminal system 100 decides the content of the provision information based on the activity information. The terminal system 100 may calculate the fatigue level of the user from the activity information and select different genres depending on the fatigue level, for example.

The terminal system 100 may decide update content of a decision rule based on the activity information. For example, the terminal system 100 may calculate the fatigue level of the user from the activity information for one day, and may vary the update content depending on the fatigue level when updating the decision rule when the user wakes up the next day.

(Variation of Provision Information)

The second embodiment is directed to an example in which the provision information is a tune to be reproduced as a sleep-inducing content item and a tune (candidate tune) to be a candidate of that tune. There is no particular limitation on the content of the provision information, and the provision condition can be updated for any provision information for each user. For example, the provision information may be recommendation information introducing a product, or the like, to the user as in the first embodiment, and/or advice information for improving the health state of the user.

For example, when the hand-held terminal 105 can provide a plurality of different functions (applications), the hand-held terminal 105 may provide (or "introduce") a recommended function, from among the plurality of different functions, as the provision information to the user. Specifically, the hand-held terminal 105 may introduce the function of reproducing a sleep-inducing content item to a user who has been determined to have trouble falling asleep from the obtained health information, and may introduce the function of reproducing an awakening content item (a piece of music and/or an image that induces for inducing the user to awaken) before awakening, to a user who has been determined to have trouble waking up.

(Variation Regarding Base Device)

In other embodiments, the base device 106 may communicate with the server without using the hand-held terminal 105 therebetween. For example, the base device 106 may have the function of communicating with the server via the network 4, as does the hand-held terminal 105. Then, the base device 106 may transmit information sensed by the base device 106 directly to the server or may transmit the information both to the hand-held terminal 105 and to the server. The base device 106 may receive the provision information directly from the server. Then, the server may transmit the provision information both to the hand-held terminal 105 and to the base device 106 or may transmit the provision information to either one of them.

[5. Functions/Effects of Second Embodiment]

In the second embodiment and the variation thereof, the information processing system performs an analysis relating to the health of a user based on the biological information of the user, and provides information based on the analysis result to the user (steps S102 to S104 and S121, the analysis section 151). The information processing system updates, for each user, based on the biological information of the user, at least a part (specifically, the tune decision rule) of a rule (which can also be said to be a condition; specifically, a decision rule) for deciding the information to be provided based on the biological information (steps S109 and S128, the update section 156, the first update section 171). The information processing system decides the information to be provided to the user, by using a rule that is set for each user as a result of the update (i.e., a rule that gets to be customized for each user by being updated). Thus, it is possible to update the rule to one of content that is suitable for the user as an individual, and it is therefore possible to provide information that is useful for each user.

Updating a rule means to include the following processes, for example.

Update of information processing program for deciding information to be provided Update of table describing rules for deciding information to be provided Update of algorithm for deciding information to be provided Update of analysis engine for deciding information to be provided Note that the biological information for updating a rule may be biological information obtained at any point in time. The information processing system may update a rule (i.e., a rule before being updated) based on biological information that is obtained after the provision of the provision information, which is decided based on the rule before being updated. Then, a rule can be updated so as to reflect the effectiveness (that is, whether effective information has been provided) of the provision information based on the rule before being updated.

In the second embodiment and the variation thereof, the rule includes a first part to be updated for each user (specifically, the tune decision rule or the second rule), and a second part that is common among a plurality of users including the present user (specifically, the genre decision rule or the first rule). In other words, as the rule for deciding the information to be provided, the information processing system uses both the first rule common among a plurality of users and the second rule which is set individually for each of the plurality of users (e.g., the second rule is set to have different content for each user). Then, the first part makes it possible to provide information suitable for each user, while the rule can be made a common rule for those parts that are common among a plurality of users, thereby simplifying the rule updating process.

Note that the first part and the second part may be used for deciding the same provision information (i.e., information of candidate tunes) as in variations described in "(Variation in which update is done based on health information of a plurality of users) and "(Variation regarding rules)" above. The first part and the second part may be those that are used for deciding information of the same type (weight values of tunes in the variation described above), as are the first rule and the second rule described above. For example, the first part and the second part may be used for deciding different provision information. That is, the content of the first provision information may be decided based on the first part, the content of the second provision information may be decided based on the second part, and the first and second provision information may be provided to the user (as the provision information described above).

Note that in a variation of the second embodiment, the information processing system calculates the first information used for deciding the provision information (specifically, the weight value calculated by the first tune decision section 181) by using the biological information and the first rule. Moreover, the information processing system decides the provision information by using the calculated first information and the second rule. Then, it is possible to decide the provision information by processing (specifically, correcting) a result based on the first rule which is common among the users (i.e., the first information) in accordance with individual second rule of the user.

Moreover, in the variation described above, the information processing system calculates the second information (specifically, the correction of the weight value decided by the first tune decision section 181) by using the second rule and the biological information, and decides the provision information based on the first information and the second information (specifically, by correcting the first information by using the second information). Then, when the first information is a type of information with which the provision information can be decided without using the second rule, the terminal system 100 can operate both in the mode in which the provision information is decided by using the first information without using the second rule and in the mode in which the provision information is decided by using the second rule.

In a variation of the second embodiment, the information processing system obtains biological information for a plurality of users (i.e., each terminal system obtains biological information of the user of the terminal system, or the server obtains biological information of each user from the terminal system of the user). The information processing system updates the second part based on at least a plurality of biological information included in the biological information (i.e., the server transmits the update notification to the terminal system, or the terminal system updates the genre decision rule in accordance with the update notification). Then, the second part which is common among a plurality of users can be updated to suitable content taking into consideration the health state of the plurality of users. Note that "update based on biological information" means to include updating based on health information that is calculated based on biological information.

Note that as in the variation described above, the condition (in other words, the timing) for updating the first part may be different from the condition for updating the second part. The frequency with which the first part is updated may be higher than the frequency with which the second part is updated. Since the first part is updated based on health information of an individual user, the first part can be updated to suitable content for the user by updating it with a high frequency. In contrast, since the second part is updated based on health information of a plurality of users, the second part can be updated to suitable content for a plurality of users by updating it based on a certain number of health information.

In a variation of the second embodiment, the information processing system includes one or more user terminal (e.g., the terminal system 100) and a server system (e.g., the data server 2 and the service server 3) that is capable of communicating with the user terminal via a network. The user terminal has the function of analyzing the health of the user and updating the rule. Each user terminal updates the first part based on the biological information obtained by the user terminal. The server system obtains biological information of a plurality of users. The second part is updated based on a plurality of biological information obtained by the server. Then, it is possible to easily update the rule by obtaining a plurality of biological information by the server.

In the second embodiment and the variation thereof, the information processing system updates at least a part of the rule for each user based on the biological information of the user and an input by the user (step S108). Then, it is possible to update the rule taking into consideration the subjective element of the user (i.e., an input by the user). Note that there is no particular limitation on the input by the user, and it is not limited to the input of an answer to a question as in the embodiment described above. For example, the information processing system may perform an update based on an input that is voluntarily made by the user (e.g., an input of a search word on a search engine). The information processing system presents a question to the user (step S107, the question presenting section 155), and uses the answer to the question as an input by the user. This makes it easy for the user to make an input, and allows the information processing system to obtain useful user inputs.

Moreover, in the second embodiment and the variation thereof, the information processing system decides the content of a question based on the biological information of the user that is obtained after the provision of the information, and presents the question to the user. Then, the information processing system updates the rule based on the biological information of the user that is obtained after the provision of the information and the answer to the question. Then, the information processing system can present an appropriate question to the user, and obtain an input of an answer that is useful for updating the rule.

In a variation of the second embodiment, the information processing system obtains environment information relating to the environment around the user when sensing the biological information (e.g., during the sleep period of the user). The information processing system decides the information to be provided based on the biological information of the user and the environment information relating to the user. Then, it is possible to provide the user with information that is more useful by taking into consideration the environment around the user. The information processing system updates at least a part of the rule based on the biological information of the user and the environment information relating to the user. Then, it is possible to more appropriately update the rule by taking into consideration the environment around the user.

In a variation of the second embodiment, the information processing system presents to the user, as the provision information, information relating to the health of the user and/or information for improving the health of the user. A tune or a candidate tune as a sleep-inducing content item described above can be said to be "information relating to the health of the user" or "information for improving the health of the user". The advice information and the recommendation information in the first embodiment or information of the function (application) for improving the health as described in "(Variation of provision information)" above can also be said to be "information relating to the health of the user" or "information for improving the health of the user".

In a variation of the second embodiment, the information processing system repeatedly executes an analysis based on the biological information that is obtained repeatedly (specifically, the analysis is performed for each sleep episode of the user). The information processing system stores, in a predetermined storage section (specifically, the health information storage section 152), at least a part of the biological information obtained repeatedly and the information calculated in the repeatedly-executed analysis. The information processing system updates, for each user, at least a part of the rule based on the biological information for a plurality of iterations and/or the information calculated over a plurality of iterations of the analysis (specifically, the health information for the past one week), which are stored in the storage section. Then, the rule is updated by using the results of a plurality of measurements and/or analyses, and it is therefore possible to provide to the user information that is more useful. The information processing system repeatedly updates the rule, and it is therefore possible to gradually change the rule to one of content that is suitable for the user. Moreover, the information processing system updates the rule each time the analysis is performed. Then, since the rule is updated each time the analysis is performed, it is possible to update rule frequently.

<Other Variations>

(Variation Regarding Process Distribution Between Devices)

The process distribution between the terminal side and the server side, the process distribution between server devices and the process distribution between devices within the terminal system described above are illustrative, and there is no particular limitation on the manner in which the various processes on the information processing system are distributed. For example, while the decision rule is stored on the terminal side in the second embodiment, a part (e.g., the genre decision rule) or the whole of the decision rule may be stored on the server side in other embodiments. Then, the process of deciding the content of the provision information and the process of updating the decision rule may be executed on the server side.

As described above, the embodiment described above can be used as an information processing system, an information processing server, and the like, with the aim of providing useful information, etc.

While certain example systems, methods, devices and apparatuses have been described herein, it is to be understood that the appended claims are not to be limited to the systems, methods, devices and apparatuses disclosed, but on the contrary, are intended to cover various modifications and equivalent arrangements included within the spirit and scope of the appended claims.

The invention claimed is:

1. An information processing system, comprising:
at least one processor; and
a memory storing computer readable instructions that, when executed by the at least one processor, cause the information processing system to:
use a rule that has been set for each user to decide content to be reproduced for aiding sleep of the user;
reproduce the content decided based on the rule;
perform an analysis relating to health of the user based on biological information of the user detected under an environment where the content is being reproduced; and
update the rule so that the content is more likely to be reproduced when a result of the analysis indicates an improved health state of the user, the improved health state determined based on, at least, history of health information related to the sleep of the user, wherein
the rule for selecting the content includes a first rule for deciding a specific content to be reproduced and a second rule for deciding a specific genre of the content to be reproduced, and
the second rule for deciding the specific genre of the content to be reproduced is updated based on biological information of a plurality of users, and the first rule for deciding the specific content to be reproduced is updated for each user based on the biological information of the respective user and/or the second rule for deciding the specific genre of the content to be reproduced.

2. The information processing system according to claim 1, the processor further configured to:
obtain biological information of each of the plurality of users; and
update the second rule based on at least a plurality of biological information included in the biological information of each of the plurality of users.

3. The information processing system according to claim 2,
the information processing system including one or more user terminals, and a server system that is configured to communicate with the one or more user terminals via a network;
the one or more user terminals are configured to execute the analysis and the update of the rule;
the one or more user terminals further configured to update the first rule based on the obtained biological information;
the server system configured to obtain biological information of each of the plurality of users; and
the information processing system configured to update the second rule based on the plurality of biological information obtained by the server.

4. The information processing system according to claim 1, the processor further configured to update, for each user, at least a part of the rule based on the biological information of the user and an input by the user.

5. The information processing system according to claim 4, the processor further configured to:
present a question to the user; and
use an answer to the question as the input by the user.

6. The information processing system according to claim 5, the processor further configured to:
decide content of the question based on the biological information of the user so as to present the question to the user; and
update, for each user, at least a part of a rule based on the biological information of the user and the answer to the question.

7. The information processing system according to claim 1, the processor further configured to:
obtain environment information relating to an environment around the user when sensing the biological information of the user; and
decide the content to be reproduced based on the biological information of the user and the environment information relating to the user.

8. The information processing system according to claim 1, the processor further configured to:
obtain environment information relating to an environment around the user when sensing the biological information of the user; and
update at least a part of a rule based on the biological information of the user and the environment information relating to the user.

9. The information processing system according to claim 1, the processor further configured to provide, to the user, information for improving the health of the user.

10. The information processing system according to claim 1,
the at least one processor of the information processing system configured to repeatedly execute the analysis based on biological information that is obtained repeatedly;
the information processing system further comprising a storage medium configured to store at least a part of the biological information obtained repeatedly and information calculated in the repeatedly-executed analysis; and
the at least one processor of the information processing system further configured to update, for each user, at least a part of the rule based on the biological information for a plurality of iterations and/or the information calculated over a plurality of iterations of the analysis, which are stored in the storage medium.

11. The information processing system according to claim 10, the processor further configured to repeatedly update the rule.

12. The information processing system according to claim 11, the processor further configured to update the rule each time the analysis is performed.

13. The information processing system according to claim 1, wherein the biological information of the user is obtained from a sensor configured to sense at least one of pulse, breathing and body movements of the user.

14. The information processing system according to claim 1, wherein the content is a composition or a movie for aiding sleep of the user.

15. The information processing system according to claim 14, wherein the content is songs of a specific genre.

16. The information processing system according to claim 1, wherein the result of the analysis indicates the improved health state when a time for the user to fall asleep after reproducing the content is short.

17. The information processing system according to claim 1, wherein a weight value associated with the content is increased when the result of the analysis is positive.

18. The information processing system according to claim 1, wherein the improved health state is determined based on health information for a plurality of sleep periods associated with the user.

19. The information processing system according to claim 1, wherein the rule is updated based on detected health states of the plurality of users that are in a group associated with the user.

20. The information processing system according to claim 19, wherein the group associated with the user, and including the plurality of users, is determined based on demographic information associated with the plurality of users.

21. The information processing system according to claim 1, wherein a weight is assigned to the specific content based on the first rule, and the weight assigned to the specific content is corrected based on the second rule.

22. The information processing system according to claim 1, wherein
 a weight is assigned to the specific content based on the first rule, and the weight is updatable using the second rule, and
 the system is configured to select the specific content using the first rule and without using the second rule in accordance with a user instruction.

23. The information processing system according to claim 1, wherein the first rule is updated based on sleep time of the user, and the second rule is updated based on sleep latency of each user in the plurality of users.

24. A non-transitory storage medium storing an information processing program to be executed by a computer of an information processing device, the information processing program causing the computer to provide execution comprising:
 using a rule that has been set for each user to decide content to be reproduced for aiding sleep of the user;
 reproducing the content decided based on the rule;
 performing an analysis relating to health of the user based on biological information of the user detected under an environment where the content is being reproduced; and
 updating the rule so that the content is more likely to be reproduced when a result of the analysis indicates an improved health state of the user, the improved health state determined based on, at least, history of health information related to the sleep of the user, wherein
 the rule for selecting the content includes a first rule for deciding a specific content to be reproduced and a second rule for deciding a specific genre of the content to be reproduced, and
 the second rule for deciding the specific genre of the content to be reproduced is updated based on biological information of a plurality of users, and the first rule for deciding the specific content to be reproduced is updated for each user based on the biological information of the respective user and/or the second rule for deciding the specific genre of the content to be reproduced.

25. An information provision method to be executed by an information processing system, the information provision method comprising:
 using a rule that has been set for each user to decide content to be reproduced for aiding sleep of the user;
 reproducing the content decided based on the rule;
 performing an analysis relating to health of the user based on biological information of the user detected under an environment where the content is being reproduced; and
 updating the rule so that the content is more likely to be reproduced when a result of the analysis indicates an improved health state of the user, the improved health state determined based on, at least, history of health information related to the sleep of the user, wherein
 the rule for selecting the content includes a first rule for deciding a specific content to be reproduced and a second rule for deciding a specific genre of the content to be reproduced, and
 the second rule for deciding the specific genre of the content to be reproduced is updated based on biological information of a plurality of users, and the first rule for deciding the specific content to be reproduced is updated for each user based on the biological information of the respective user and/or the second rule for deciding the specific genre of the content to be reproduced.

* * * * *